US006692916B2

(12) United States Patent
Bevilacqua et al.

(10) Patent No.: US 6,692,916 B2
(45) Date of Patent: Feb. 17, 2004

(54) SYSTEMS AND METHODS FOR CHARACTERIZING A BIOLOGICAL CONDITION OR AGENT USING PRECISION GENE EXPRESSION PROFILES

(75) Inventors: Michael P. Bevilacqua, Boulder, CO (US); Danute M. Bankaitis-Davis, Longmont, CO (US); John C. Cheronis, Conifer, CO (US); Victor Tryon, Loveland, CO (US)

(73) Assignee: Source Precision Medicine, Inc., Boulder, CO (US)

( * ) Notice: Subject to any disclaimer, the term of this patent is extended or adjusted under 35 U.S.C. 154(b) by 0 days.

(21) Appl. No.: 09/821,850

(22) Filed: Mar. 29, 2001

(65) Prior Publication Data

US 2003/0229455 A1 Dec. 11, 2003

Related U.S. Application Data

(63) Continuation-in-part of application No. 09/605,581, filed on Jun. 28, 2000, now abandoned.
(60) Provisional application No. 60/195,522, filed on Apr. 7, 2000, and provisional application No. 60/141,542, filed on Jun. 28, 1999.

(51) Int. Cl.[7] .................................................. C12Q 1/68
(52) U.S. Cl. .................. 435/6; 702/19; 702/20
(58) Field of Search .............................. 435/6; 702/19, 702/20

(56) References Cited

U.S. PATENT DOCUMENTS

| 5,643,765 | A | 7/1997 | Willey ........................ 435/91.2 |
| 5,811,231 | A | 9/1998 | Farr et al. ...................... 435/6 |
| 5,846,720 | A | 12/1998 | Foulkes et al. ................. 435/6 |
| 5,866,330 | A | 2/1999 | Kinzier et al. .................. 435/6 |
| 5,955,269 | A | 9/1999 | Ghai et al. ...................... 435/6 |
| 5,968,784 | A | 10/1999 | Spinella et al. ............ 435/91.1 |
| 5,994,076 | A | 11/1999 | Chenchik et al. ............... 435/6 |
| 6,132,969 | A | 10/2000 | Stoughton et al. .............. 435/6 |
| 6,146,828 | A | 11/2000 | Lapidus et al. ................. 435/6 |
| 6,150,169 | A | 11/2000 | Smith et al. ................. 435/455 |
| 6,165,709 | A | 12/2000 | Friend et al. .................... 435/4 |
| 6,185,561 | B1 | 2/2001 | Balaban et al. ................. 707/6 |
| 6,203,987 | B1 | 3/2001 | Friend et al. .................... 435/6 |
| 6,203,988 | B1 | 3/2001 | Kambara et al. ............... 435/6 |
| 6,218,122 | B1 | 4/2001 | Friend et al. .................... 435/6 |
| 6,222,093 | B1 | 4/2001 | Marton et al. ................... 800/3 |
| 6,232,065 | B1 | 5/2001 | Robinson et al. ............... 435/6 |
| 6,245,517 | B1 | 6/2001 | Chen et al. ...................... 435/6 |
| 2001/0029028 | A1 | 10/2001 | Danenberg et al. ............. 435/6 |
| 2001/0051344 | A1 | 12/2001 | Shalon et al. ................... 435/6 |
| 2002/0012932 | A1 | 1/2002 | Wang ............................. 435/6 |
| 2002/0045197 | A1 | 4/2002 | Friend et al. ............... 435/7.21 |

FOREIGN PATENT DOCUMENTS

| JP | 10-261029 | 9/1998 | |
| WO | WO 94/23023 | 10/1994 | ........... C12N/15/00 |
| WO | WO 97/41261 | 11/1997 | ........... C12Q/1/68 |
| WO | WO 98/24935 | 6/1998 | ........... C12Q/1/68 |
| WO | WO 99/04251 | 1/1999 | ........... G01N/27/26 |
| WO | WO 99/11822 | 3/1999 | ........... C12Q/1/68 |
| WO | WO 99/44063 | 9/1999 | ........... G01N/33/50 |
| WO | WO 99/46403 | 9/1999 | ........... C12Q/1/68 |
| WO | WO 99/54510 A2 | 10/1999 | ........... C12Q/1/68 |
| WO | WO 99/54510 A3 | 10/1999 | ........... C12Q/1/68 |
| WO | WO 99/57130 | 11/1999 | ........... C07H/21/04 |
| WO | WO 99/58720 | 11/1999 | ........... C12Q/1/68 |
| WO | WO 00/11208 | 3/2000 | ........... C12Q/1/68 |
| WO | WO 00/22172 | 4/2000 | ........... C12Q/1/68 |
| WO | WO 00/28092 | 5/2000 | ........... C12Q/1/68 |
| WO | WO 01/32928 | 5/2001 | |

OTHER PUBLICATIONS

Rodrigues–Antona et al., Archieves of Biochemistry and Biophysics, vol. 376, No. 1, Apr. 1, pp. 109–116, 2000.*

Meijers–Heijboer, M.D., et al., "Breast Cancer after Prophylactic Bilateral Mastectomy in Women with a BRCA1 or BRCA2 Mutation", The New England Journal of Medicine, vol. 345:159–164, Jul. 19, 2001, No. 3 (online abstract only).

Rosenwald, M.D., et al., "The Use of Molecular Profiling to Predict Survival after Chemotherapy for Diffuse Large–B–Cell Lymphoma", The New England Journal of Medicine, vol. 346:1937–1947, Jun. 20, 2002, No. 25 (online abstract only).

Teague, et al., "Activation changes the spectrum but not the diversity of genes expressed by T cells", Proc. Natl. Acad. Sci. USA, vol. 96, Issue 22, 12691–12696, Oct. 26, 1999.

Zhang, et al., "Recursive partitioning for tumor classification with gene expression microarray data", Proc. Natl. Acad. Sci, USA, vol. 98, Issue 12, 6730–6735, Jun. 5, 2001.

Takahashi, et al., "Gene expression profiling of clear cell renal cell carcinoma: Gene identification and prognostic classification", Proc. Natl. Acad. Sci. USA, vol. 98, Issue 17, 9754–9759, Aug. 14, 2001.

Staunton, et al., "Chemosensitivity predication by transcriptional profiling", Proc. Natl. Acad. Sci. USA, vol. 98, Issue 19, 10787–10792, Sep. 11, 2001.

Rafalski, et al., "New experimental and computational approaches to the analysis of gene expression", Acta Biochimica Polonica, vol. 45, No. 4/1998, 929–934.

Zajchowski, et al., "Identification of Gene Expression Profiles That Predict the Aggressive Behavior of Breast Cancer Cells", Canceer Research 6, 5168–5178, Jul. 1, 2001.

(List continued on next page.)

Primary Examiner—Marianne P. Allen
(74) Attorney, Agent, or Firm—Bromberg & Sunstein LLP

(57) ABSTRACT

Methods are provided for evaluating a biological condition of a subject using a calibrated profile data set derived from a data set having a plurality of members, each member being a quantitative measure of the amount of a subject's RNA or protein as distinct constituents in a panel of constituents. The biological condition may be a naturally occurring physiological state or may be responsive to treatment of the subject with one or more agents. Calibrated profile data sets may be used as a descriptive record for an agent.

17 Claims, 49 Drawing Sheets

OTHER PUBLICATIONS

Korenberg, "Prediction of Treatment Response Using Gene Expression Profiles", Journal of Proteome Research 2002, 1, 55–61.

Kim, et al., "Strong Feature Sets from Small Samples", Journal of Computational Biology, vol. 9, No. 1, 2002, Mary Ann Liebert, Inc. pp. 1127–1146.

Zhan, et al., "Global Gene Expression Profiles Can be Used to Accurately Predict Chromosome 13 Deletion in Multiple Myeloma", Abstract #1553, Poster Board #–Session: 658–II.

Cole, et al., "The genetics of cancer–a 3D model", Nature Genetics Supplement, vol. 21, Jan. 1999.

Van 't Veer, et al., "Gene expression profiling predicts clinical outcome of breast cancer", Nature, vol. 415, Jan. 31, 2002.

Mangalam, et al., "GeneX: An open source gene expression database and integrated tool set", IBM Systems Journal, (2001), 40 (2), 552–569, 79 refs. ISSN: 0018–8670.

Coenen, et al. "A quantitative PCR measurement of messenger RNA expression of IGF–I, IGF–II and IGFBP–5 in human skeletal muscle", *Growth Hormone & IGF Research* 1999, 9, 179–186 Article No.ghir.1999.0104.

Guan–Chiun Lee, et al. Analysis of the Gene Family kEncoding Lipases in candid rugosa by Competitive Reverse Transcription–PCR, *Applied and Environmental Microbiology*, Sep. 1999, pp. 3888–3895.

Jensen, et al. "Competitive reverse transcriptin polymerase chain reaction for quantifying pre–MRNA and mRNA of major acute phase proteins", *Journal of Immunological Methods*, 215 (1998), pp. 45–58.

Loitsch, et al. "Reverse Transcription–Competitive Multiplex PCR Improves Quantification of mRNA in Clinical Samples—Application to the Low Abundance CFTR mRNA", *Clinical Chemistry* 45:5, (1999), pp. 619–624.

Zhang, et al. "A Novel Highly Reproducible Quantitative Competitive RT PCR System", *J. Mol. Biol* (1997) 274, pp. 338–352.

Vukmirovic et al. "Exploring genome space" Nature, vol. 405:820–822 Jun. 15, 2000.

Eisenberg et al. "Protein function in the post–genomic era" Nature, vol. 405:823–826 Jun. 15, 2000.

Lockhart et al. "Genomics, gene expression and DNA arrays" Nature, vol. 405:827–836 Jun. 15, 2000.

Pandey et al. "Proteomics to study genes and genomes" Nature, vol. 405:837–846 Jun. 15, 2000.

Risch "Searching for genetic determinants in the new millennium" Nature, vol. 405:847–856 Jun. 15, 2000.

Roses "Pharmacogenetics and the practice of medicine" Nature, vol. 405: 857–865 Jun. 15, 2000.

* cited by examiner

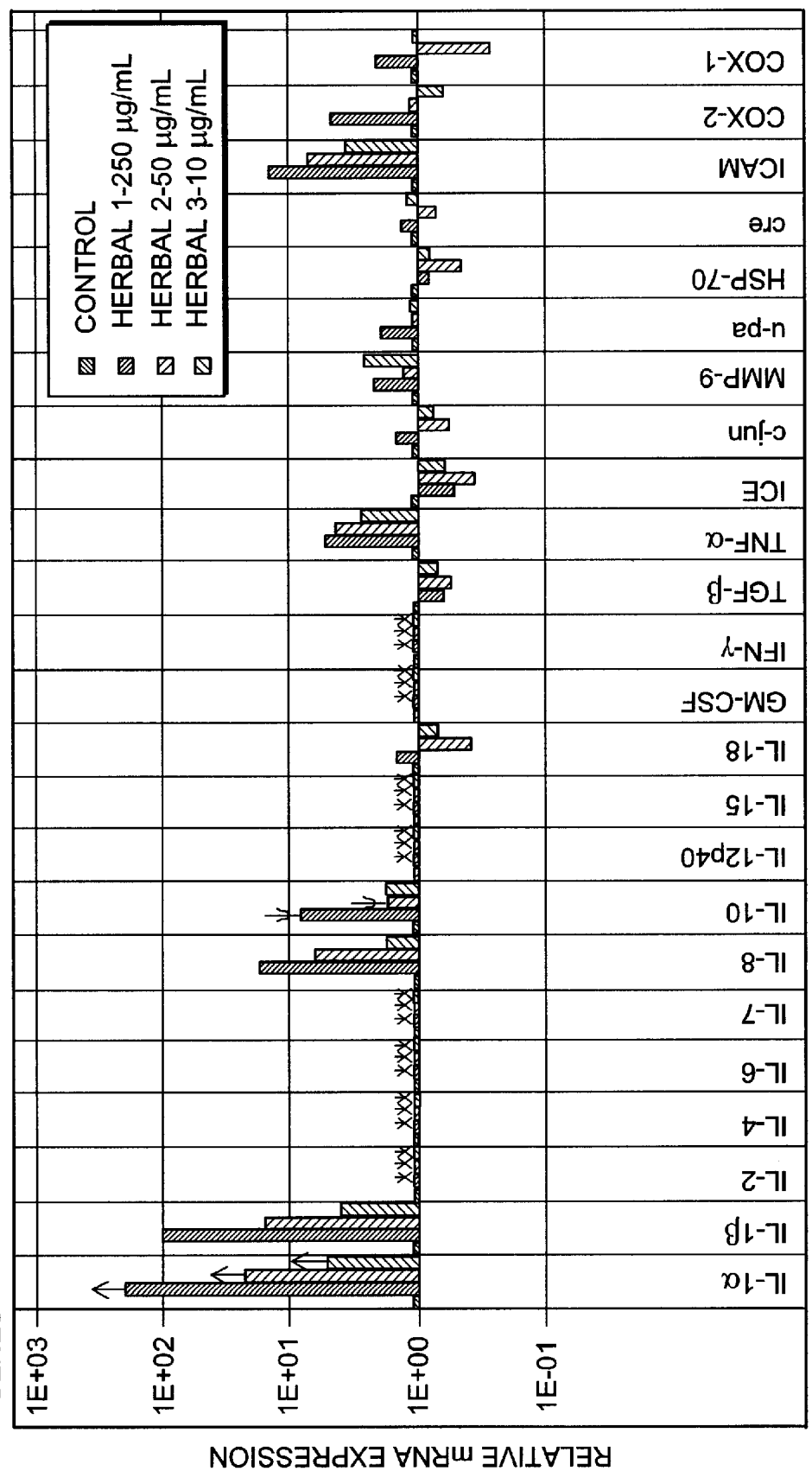

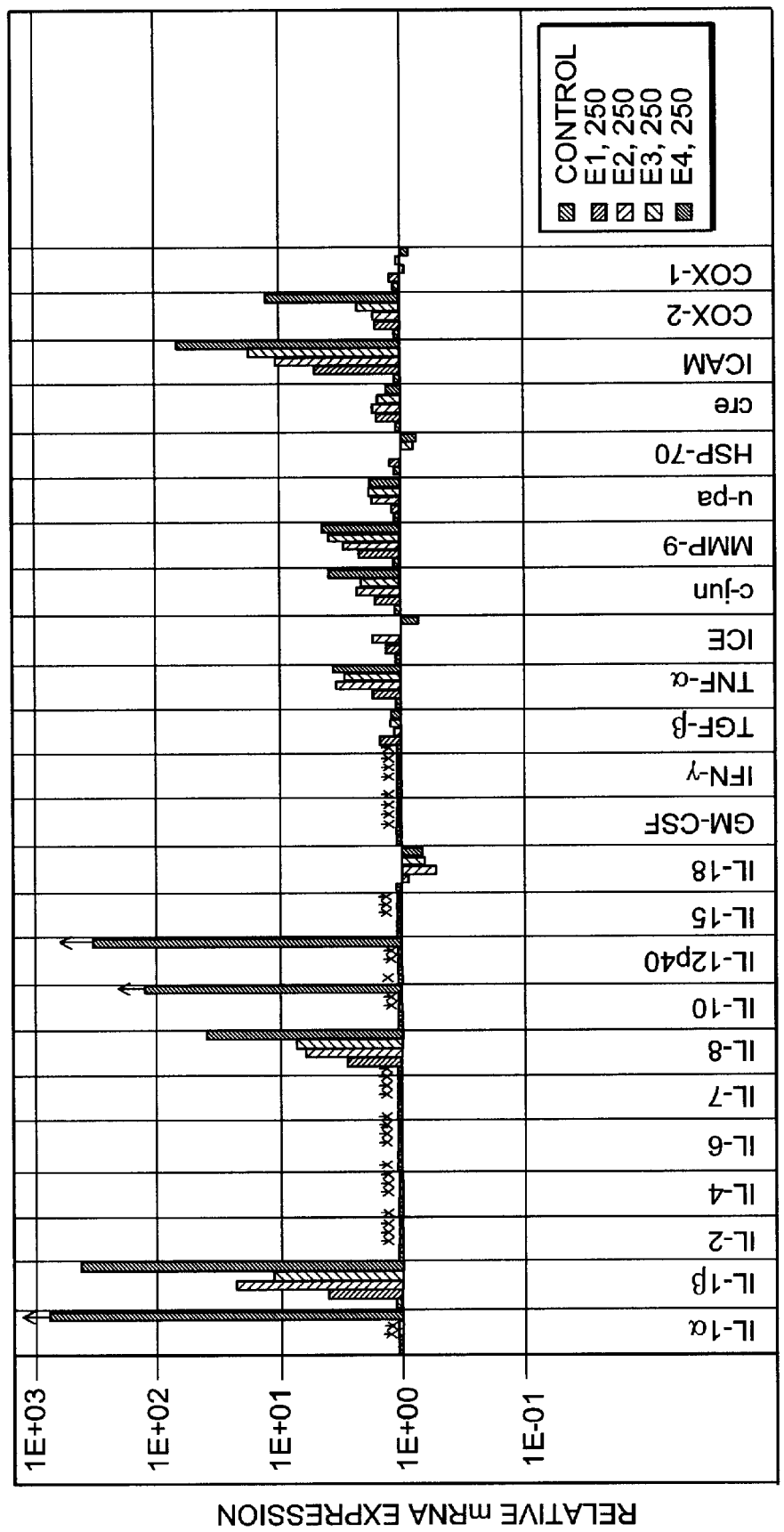

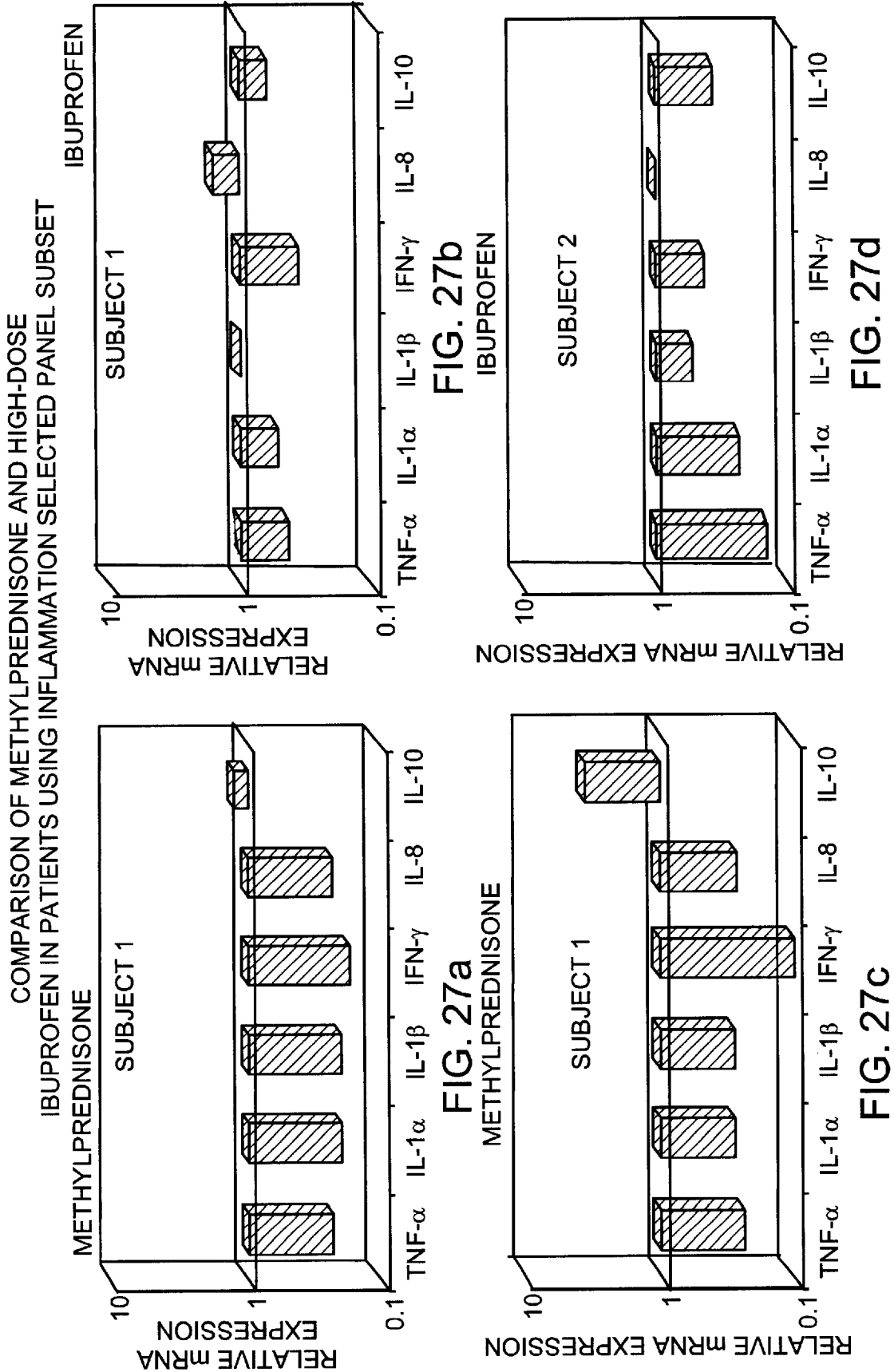

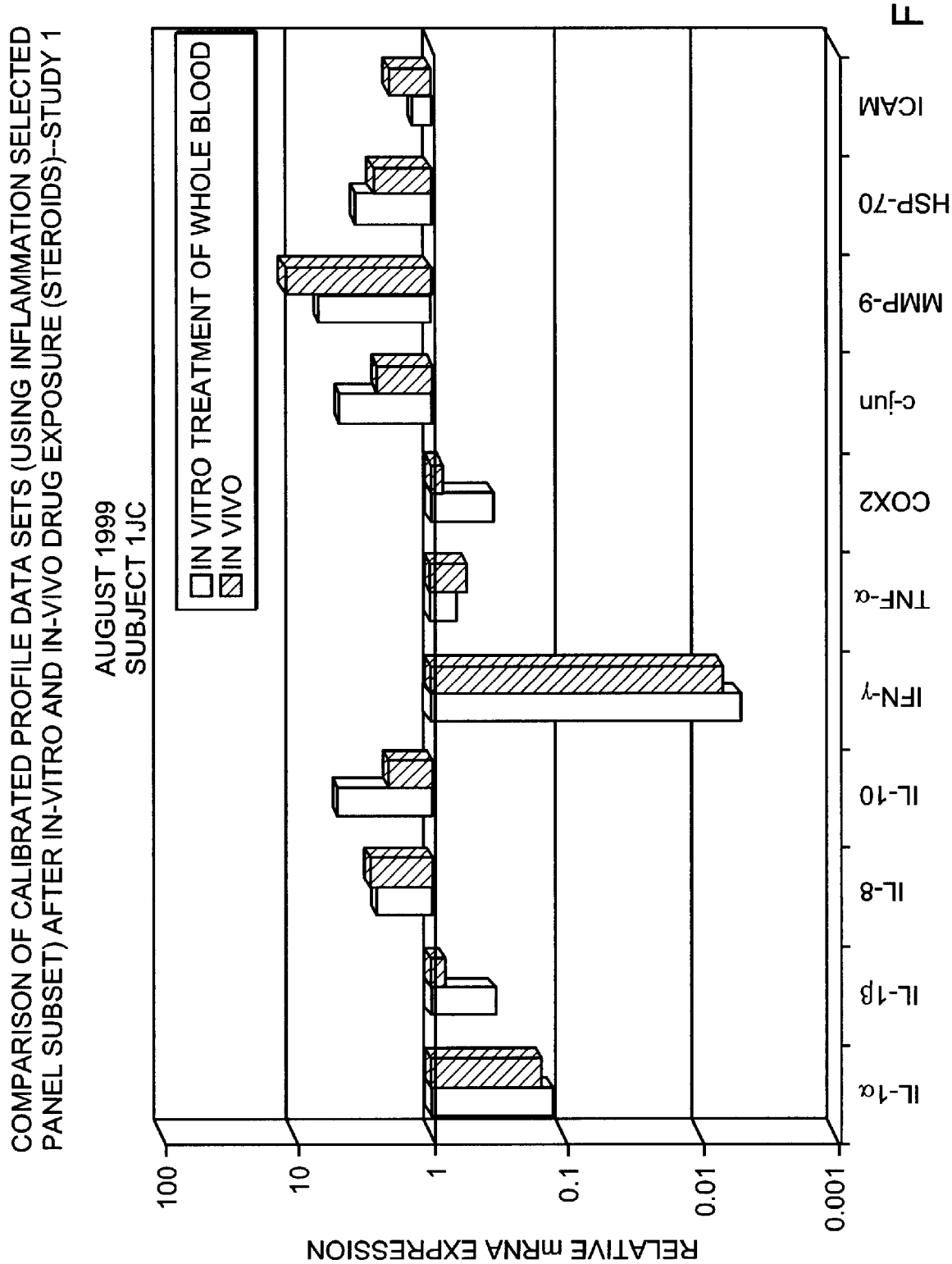

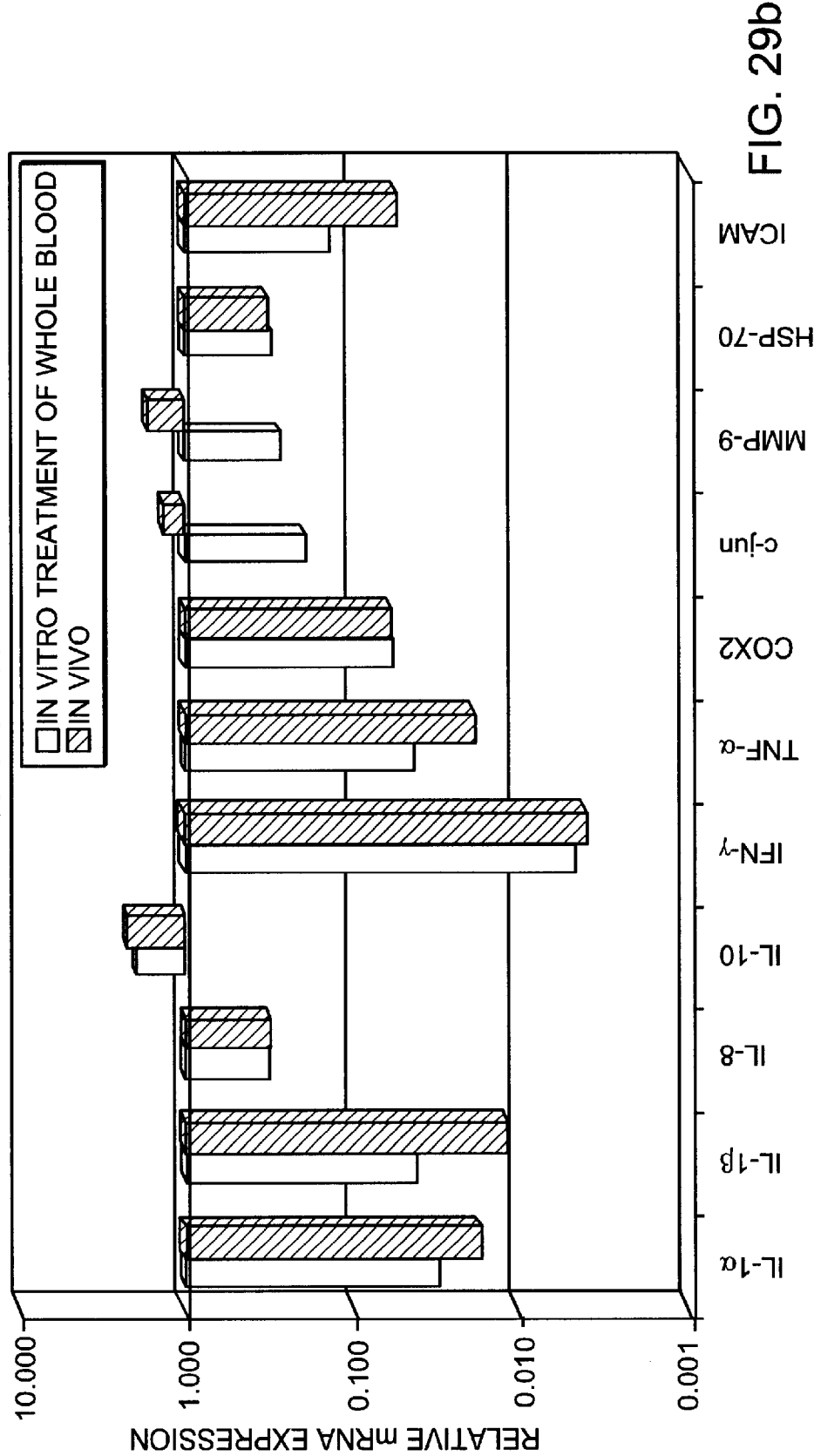

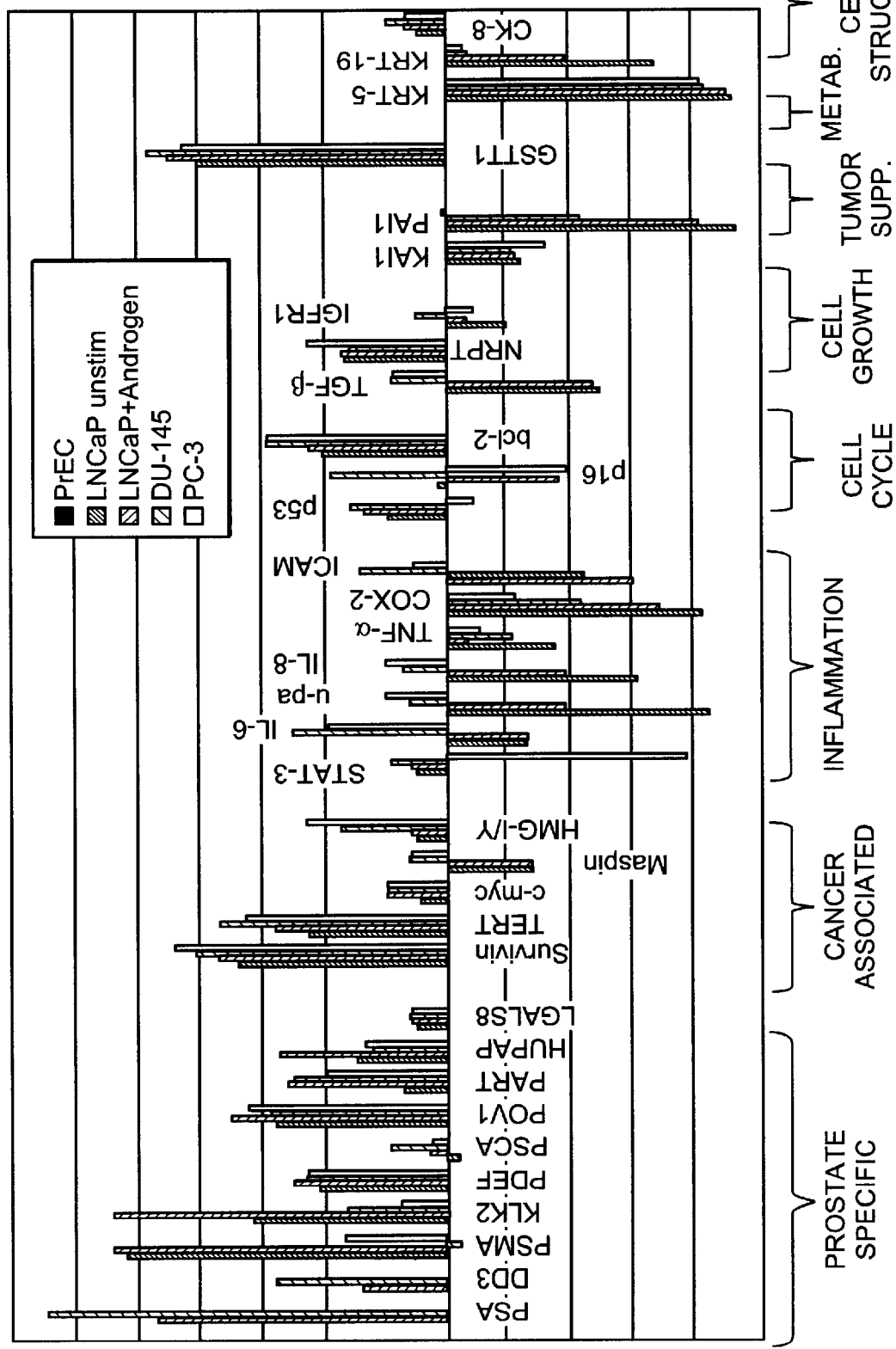
FIG. 30 EFFECT OF DIFFERENT AGENTS EVALUATED USING A SUBSET OF THE SELECTED PROSTATE PANEL, AND SHOWING BROAD FUNCTIONS OF PANEL CONSTITUENTS

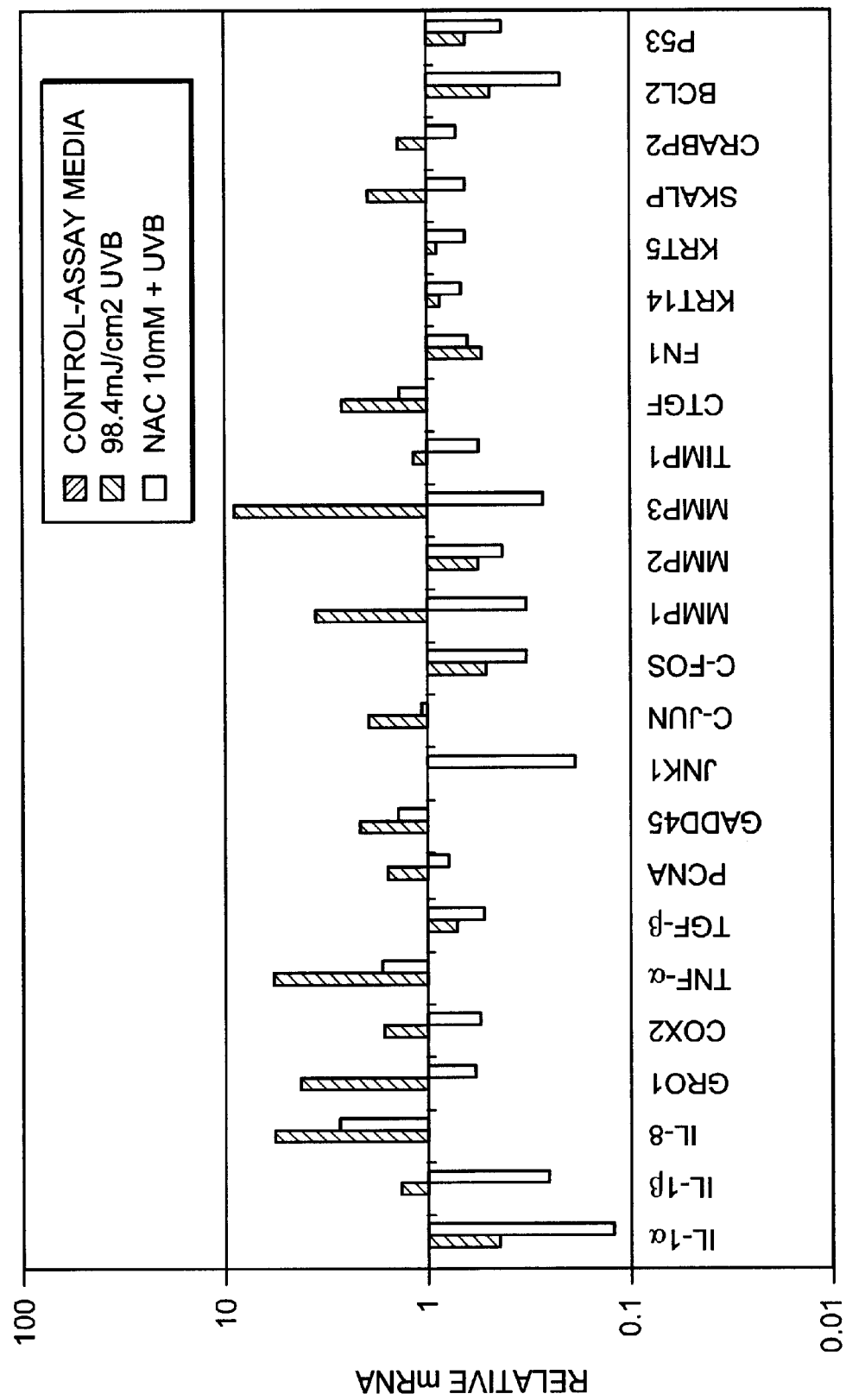

SYSTEMS AND METHODS FOR CHARACTERIZING A BIOLOGICAL CONDITION OR AGENT USING PRECISION GENE EXPRESSION PROFILES

RELATED APPLICATION

This application is a continuation in of U.S. application Ser. No. 09/605,581, filed Jun. 28, 2000, now abandon by the same inventors herein, which application claims priority from provisional application serial No. 60/141,542, filed Jun. 28, 1999 and provisional application serial No. 60/195,522 filed Apr. 7, 2000. These related applications are hereby incorporated herein by reference.

Technical Field

Embodiments of the recent invention provide systems and methods for utilizing gene expression analysis for characterizing a biological condition or agent.

BACKGROUND ART

There has been substantial discussion including congressional hearings concerning medical errors. One source of medical errors include errors with medications. Upwards of 98,000 hospitalized patients annually have been documented to be victims of medication errors (Statement of the American Pharmaceutical Association to the Senate Appropriations Committee Labor, health and Human Services Education Subcommittee Hearing on Medical Errors Dec. 13, 1999). These errors include problems arising from drug interactions for a particular patient taking more than one drug, problems concerning the response of an individual to a particular drug and incorrect medication for a particular condition. Medical errors further arise as a result of misdiagnosis. This may occur as a result of insensitive diagnostic techniques or a wide range of interpersonal variability in the manner in which a clinical state is manifest. At present, there are few tools available for optimizing prognosis, diagnosis and treatment of a medical condition taking into account the particular phenotype and genotype of an individual.

There has been increasing interest in herbal drugs or nutraceuticals. These compounds are grown and collected from around the world, and consequently the compounds are subject to regional and temporal differences in collection and preparation that are difficult to control. It is frequently the case that one batch of a nutraceutical may be effective, there is no assurance that a second batch will be effective. Moreover. analysis of nutraceuticals is problematic because these drugs are complex mixtures in which little is known with respect to the active agent.

All new therapeutic agents require some form of clinical trials. It is known that a drug for treating tumor that is tested in a clinical trial using standard recruiting techniques for patients, may in fact show only limited efficacy. If the beneficial effect observed in a clinical population is too small, the drug will not receive approval by the Food and Drug Administration for use in the population at large. However, the small beneficial effect observed may in fact be an artifact of the clinical trial design or the clinical endpoint in the population of patients. It would be desirable to have criteria for screening patients as they enter a clinical trial to ensure that the beneficial effect of a drug if it exists may be detected and quantified.

SUMMARY OF THE INVENTION

In a first embodiment of the invention there is provided a method, for evaluating a biological condition of a subject, that includes: obtaining from the subject a sample having at least one of RNAs and proteins; deriving from the sample a first profile data set, the first profile data set including a plurality of members, each member being a quantitative measure of the amount of a distinct RNA or protein constituent in a panel of constituents selected so that measurement of the constituents enables measurement of the biological condition; and producing a calibrated profile data set for the panel, wherein each member of the calibrated profile data set is a function of a corresponding member of the first profile data set and a corresponding member of a baseline profile data set for the panel, the calibrated profile data set providing a measure of the biological condition of the subject.

In another embodiment, a method is provided for evaluating a biological condition of a subject, that includes obtaining from the subject a first sample having at least one of fluid, cells and active agents; applying the first sample or a portion thereof to a defined population of indicator cells; obtaining from the indicator cells a second sample containing at least one of RNAs or proteins; deriving from the second sample a first profile data set, the first profile data set including a plurality of members, each member being a quantitative measure of the amount of a distinct RNA or protein constituent in a panel of constituents selected so that measurement of the constituents enables measurement of the biological condition; and producing a calibrated profile data set for the panel, wherein each member of the calibrated profile data set is a function of a corresponding member of the first profile data set and a corresponding member of a baseline profile data set for the panel, the calibrated profile data set providing a measure of the biological condition of the subject.

In a another embodiment, a method is provided for evaluating a biological condition affected by an agent, the method including: obtaining, from a target population of cells to which the agent has been administered, a sample having at least one of RNAs and proteins; deriving from the sample a first profile data set, the first profile data set including a plurality of members, each member being a quantitative measure of the amount of a distinct RNA or protein constituent in a panel of constituents selected so that measurement of the constituents enables measurement of the biological condition; and producing a calibrated profile data set for the panel, wherein each member of the calibrated profile data set is a function of a corresponding member of the first profile data set and a corresponding member of a baseline profile data set for the panel, the calibrated profile data set providing a measure of the biological condition as affected by the agent.

In a another embodiment, a method is provided for evaluating the effect on a biological condition by a first agent in relation to the effect by a second agent, including: obtaining, from first and second target populations of cells to which the first and second agents have been respectively administered, first and second samples respectively, each sample having at least one of RNAs and proteins; deriving from the first sample a first profile data set and from the second sample a second profile data set, the profile data sets each including a plurality of members, each member being a quantitative measure of the amount of a distinct RNA or protein constituent in a panel of constituents selected so that measurement of the constituents enables measurement of the biological condition; and producing for the panel a first calibrated profile data set and a second profile data set, wherein (i) each member of the first calibrated profile data set is a function of a corresponding member of the first profile data set and a corresponding member of a first baseline profile data set for the panel, and (ii) each member of the second calibrated profile data set is a function of a corresponding member of the second profile data set and a corresponding member of a second baseline profile data set for the panel, the calibrated profile data sets providing a measure of the effect by the first agent on the biological condition in relation to the effect by the second agent.

In a further embodiment, a method of conducting a clinical trial of an agent, is provided, including: causing the blind administration of a selected one of a placebo and the agent to each candidate of a pool of subjects; and using quantitative gene expression to monitor an effect of such administration.

In another embodiment, a digital storage medium is provided on which is stored a computer readable calibrated profile data set, wherein: the calibrated profile data set relates to a sample having at least one of RNAs and proteins derived from a target cell population to which an agent has been administered; the calibrated profile data set includes a first plurality of members, each member being a quantitative measure of a change in an amount of a distinct RNA or protein constituent in a panel of constituents selected so that measurement of the constituents enables measurement of a biological condition as affected by administration of the agent.

In another embodiment, a digital storage medium is provided on which is stored a plurality of records $R_i$ relating to a population of subjects, each record $R_i$ corresponding to a distinct instance $P_i$ of a computer readable profile data set P wherein: each instance $P_i$ of the profile data set P relates to a distinct sample derived from a subject, the sample having at least one of RNAs and proteins; the profile data P set includes a plurality of members $M_j$, each member $M_j$ being a quantitative measure of the amount of a distinct RNA or protein constituent in a panel of constituents selected so that measurement of the constituents enables measurement of a biological condition; each record $R_i$ includes, for each member $M_{ij}$ of a corresponding distinct instance $P_i$ of the profile data set P, a value corresponding to the value of the member $M_{ij}$; and each record $R_i$ also includes a reference to a characteristic of the subject relative to the record, the characteristic being at least one of age group, gender, ethnicity, geographic location, diet, medical disorder, clinical indicator, medication, physical activity, body mass, and environmental exposure.

In a further embodiment, a digital storage medium is provided on which is stored a large number of computer readable profile data sets, wherein each profile data set relates to a sample derived from a target cell population to which has been administered an agent, the sample having at least one of RNAs and proteins; each profile data set includes a plurality of members, each member being a quantitative measure of the amount of a distinct RNA or protein constituent in a panel of constituents selected so that measurement of the constituents enables measurement of a biological condition; and the panel is the same for all profile data sets.

In a another embodiment of the invention, a method is provided for evaluating a biological condition of a subject, based on a sample from the subject, the sample having at least one of RNAs and proteins, the method including: deriving from the sample a first instance of a profile data set, the profile data set including a plurality of members, each member being a quantitative measure of the amount of a distinct RNA or protein constituent in a panel of constituents selected so that measurement of the constituents enables measurement of the biological condition; and producing a first instance of a calibrated profile data set for the panel, wherein each member of an instance of the calibrated profile data set is a function of a corresponding member of an instance of the profile data set and a corresponding member of an instance of a baseline profile data set for the panel, the calibrated profile data set providing a measure of the biological condition of the subject; accessing data in a condition database, the condition database having a plurality of records relating to a population of subjects, each record corresponding to a distinct instance of the calibrated profile data set; and evaluating the first instance of the calibrated profile data set in relation to data in the condition database.

In another embodiment of the invention, a method is provided of displaying quantitative gene expression analysis data associated with measurement of a biological condition, the method including: identifying a first profile data set pertinent to the gene expression analysis data, the first profile data set including a plurality of members, each member being a quantitative measure of the amount of a distinct RNA or protein constituent in a panel of constituents selected so that measurement of the constituents enables measurement of the biological condition; producing a calibrated profile data set for the panel, wherein each member of the calibrated profile data set is a function of a corresponding member of the first profile data set and a corresponding member of a baseline profile data set for the panel, the calibrated profile data set providing a measure of the biological condition of the subject; and displaying the calibrated profile data set in a graphical format.

Another embodiment is directed to a descriptive record of a change in a biological condition, that includes: a first set of numerical gene expression values for a panel of gene loci, each value in the set corresponding to a single gene locus in a panel of gene loci, the set of values forming a profile data set for a population of cells subjected to a first biological condition; a second set of numerical gene expression values for the panel of gene loci, each value in the set corresponding to a single gene locus, the set of values forming a baseline profile data set for a second population of cells subjected to a second biological condition, the second set of values optionally being an average for multiple gene expression values from multiple populations of cells for each locus in the panel: and a third set of numbers corresponding to the ratio of the first set of values and the second set of values with respect to each gene locus in the panel, the third set being a calibrated profile data set; the profile data set and the calibrated profile data set being descriptive of the first biological condition with respect to the second biological condition.

In another embodiment, a method for diagnosing a biological condition of a subject is provided that includes: obtaining a sample from a subject; subjecting a population of cells to the sample and determining the presence of a first biological condition with respect to a second biological condition according to any of the above claims.

In another embodiment, a method is provided for diagnosing a susceptibility for a biological condition in a subject, that includes obtaining a sample from the subject; creating a descriptive record, according to the above, wherein the baseline set of values is an average of second values contained in a library of descriptive records for the second biological condition; the library containing a plurality of descriptive records grouped according to a predetermined biological condition; comparing the calibrated profile data set of the subject with the library of calibrated profile data sets and diagnosing the susceptibility of the subject.

In another embodiment, a method is provided for monitoring the progress of a biological condition, including: creating a plurality of descriptive records, according to the above; wherein each set of first values is determined at preselected time intervals with respect to the first record; comparing each calibrated profile data set with a library of calibrated profile data sets, the plurality of calibrated profile data sets being grouped according to a predetermined biological condition; and determining the progress of the biological condition with respect to gene expression.

In another embodiment, a method is provided for establishing the biological activity of a composition, including: selecting a population of cells; subjecting the cells to the composition; and determining the record according to the above description using a standardized baseline profile data set for the biological condition.

In another embodiment, a method is provided for determining which therapeutic agent from a choice of a plurality of therapeutic agents to administer to a subject so as to change a biological condition in a subject from a first biological condition to a second biological condition; including: subjecting a sample from the subject to each of a plurality of therapeutic agents; determining a descriptive record for each of the samples according to any of the above described methods, comparing each of the calibrated profile data sets to a library of calibrated profile data sets, the library of calibrated data sets being grouped according to a predetermined biological condition; and determining which of the therapeutic agents is capable of changing the first biological condition in the subject to the second biological condition in the subject.

In another embodiment, a method is provided for characterizing the biological effectiveness of a single batch of a composition produced by a manufacturing process, comprising: providing a fingerprint or signature profile according to any of the above methods; and labeling the batch of the composition by placing the fingerprint (signature profile) on each container in the batch.

In another embodiment, a method is provided for accessing biological information on a digital storage medium as described above, including: making the information available to a user.

In another embodiment, a method is provided for consumer evaluation of a product, wherein the consumer evaluation is dependent on a signature profile, including: identifying the product using the signature profile.

In another embodiment, a computer program product is provided for evaluating a biological condition of a subject or for evaluating a biological condition resulting from the use of an agent, including a computer usable medium having computer readable program code thereon, the computer program code; including: a program code for classifying a sample from the subject or the agent for an identifiable record; a program code for deriving a first data set, the first profile data set including a plurality of members, each member being a quantitative measure of the amount of a distinct RNA or protein constituent in a panel of constituents selected so that measurement of the constituents enables measurement of the biological condition; the profile data set being stored in the record; and a program code for optionally producing a calibrated profile data set for the panel, for storage in the record, each member of the calibrated profile data set being a function of a corresponding member of the first profile data set and a corresponding member of a baseline profile data set for the panel, the calibrated profile data set providing a measure of the biological condition of the subject.

In another embodiment of the invention, a computer system for evaluating a biological condition of a subject or for evaluating a biological condition resulting from the use of an agent is provided, the computer system, including: a classification module for classifying a sample from the subject or the agent in an identifiable record; a derivative module for deriving a first data set, the first profile data set including a plurality of members, each member being a quantitative measure of the amount of a distinct RNA or protein constituent in a panel of constituents selected so that measurement of the constituents enables measurement of the biological condition; and a production module for producing a calibrated profile data set for the panel, wherein each member of the calibrated profile data set is a function of a corresponding member of the first profile data set and a corresponding member of a baseline profile data set for the panel, the calibrated profile data set providing a measure of the biological condition of the subject.

In another embodiment, a method is provided for analyzing a patient for a biological condition at a remote site, including: providing a kit for measuring a profile data base for evaluating a biological condition, the kit including reagents for quantitative analysis of RNA or protein for a panel of gene loci; accessing a centralized database containing baseline profile data sets corresponding to the panel; determining the calibrated profile data set for the patient; and analyzing the biological condition of the patient.

Further embodiments of the invention include the use of calibrated profile data bases for determining the biological condition at one site in a subject from a sample taken from a second remote site. The biological condition may include disease, therapeutic interventions, aging, health conditioning and exercise, exposure to toxins, status of infection and health status. For example, calibrated precision profiles may be used to measure a biological condition(s) in one site (for example, the liver) by sampling cells from the same subject, but at a different site not generally considered a target for the biological condition, for example, peripheral blood cells in the case of liver disease.

Further embodiments of the invention include the use of calibrated profile data bases for determining the biological condition of the subject that includes placing a cell or fluid sample on indicator cells to assess the biological condition, the biological condition including disease, therapeutic interventions, aging, health conditioning and exercise, exposure to toxins, status of infection and health status.

Further embodiments of the invention include the use of calibrated profile data bases and profiles to assess, compare and contrast the bioactivities of therapeutic agents and therapeutic agent candidates including comparison of two agents having unknown properties; comparison of agents that are complex mixtures against those that are simple mixtures and comparisons of a single agent against a class of agents.

Further embodiments of the invention include the use of calibrated profile databases derived from in vitro dosing of an agent in indicator cells, or fluids or cells ex vivo to predict in vivo activities, activities including efficacy and toxicity and further permitting data on short term in vivo dosing of agent to predict long-term activities as described herein.

Another embodiment of the invention is at least one databases and its uses, the databases containing at least one of calibrated profile data sets and baseline profile data sets for discrete populations identified according to factors including diseases, geography, ethnicity, age and state of health.

A further embodiment of the invention is a database corresponding to an individual over time, the uses including managing a personalized health care program.

Additional embodiments include methods of running a clinical trial using calibrated profile data and databases containing calibrated profile data from in vitro and in vivo studies of the effect of the agent on populations of cells and methods of building a to clinical research network that uses calibrated profile data and traditional medical data.

Another embodiment of the invention provides a method, for evaluating a biological condition of a subject. This method includes:

a. obtaining from the subject a sample having at least one of RNAs and proteins;

b. deriving from the sample a first profile data set, the first profile dataset including a plurality of members, each member being a quantitative measure of the amount of a distinct RNA or protein constituent in a panel of constituents selected so that measurement of the constituents enables measurement of the biological condition; and c. producing a calibrated profile data set for the panel, wherein each member of the calibrated profile data set is a function of a corresponding member of the first profile data set and a corresponding member of a baseline profile data set for the panel, the calibrated profile data set providing a measure of the biological condition of the subject.

In this embodiment, the biological condition relates to inflammation and the panel includes at least half, and, optionally, at least eighty percent of the constituents of the Inflammation Selected Panel of Table 1. In a related embodiment, the biological condition relates to cell growth and differentiation and the panel includes at least half, and optionally at least eighty percent, of the constituents of the Cell Growth and Differentiation Selected Panel of Table 2. In other related embodiments, the biological condition relates to metabolism and toxicity and the panel includes at least half, and optionally at least eighty percent, of the constituents of the Liver Metabolism and Toxicity Selected Panel of Tables 3 or 7. In another related embodiment, the biological condition relates to skin response and the panel includes at least half, and optionally at least eighty percent, of the constituents of the Skin Response Selected Panel of Table 4. In another related embodiment, the biological condition relates to the vascular system and the panel includes at least half, and optionally, at least eighty percent, of the constituents of the Vascular Selected Panel of Table 6. In a further related embodiment, the biological condition relates to the prostate health and disease and the panel includes at least half, and optionally at least eighty percent of the constituents of the Prostate Selected Panel of Table 5.

Another embodiment of the invention provides a method, for evaluating a biological condition of a subject, that includes: obtaining from the subject a sample having at least one of RNAs and proteins; deriving from the sample a profile data set, the profile data set including a plurality of members, each member being a quantitative measure of the amount of a distinct RNA or protein constituent in a panel of constituents selected so that measurement of the constituents enables measurement of the biological condition; wherein such measurement is performed for each constituent under conditions wherein efficiencies of amplification for all constituents are substantially similar, the profile data set providing a measure of the biological condition of the subject.

Another embodiment of the invention provides a method, for evaluating a biological condition of a subject, that includes: obtaining from the subject a first sample having at least one of fluid, cells and active agents; applying the first sample or a portion thereof to a defined population of indicator cells; obtaining from the indicator cells a second sample containing at least one of RNAs or proteins; deriving from the second sample a profile data set, the profile data set including a plurality of members, each member being a quantitative measure of the amount of a distinct RNA or protein constituent in a panel of constituents selected so that measurement of the constituents enables measurement of the biological condition; wherein such measure is performed for each constituent under conditions wherein efficiencies of amplification for all constituents are substantially similar, the profile data set providing a measure of the biological condition of the subject.

Another embodiment of the invention provides method for evaluating a biological condition affected by an agent, the method that includes obtaining, from a target population of cells to which the agent has been administered, a sample having at least one of RNAs and proteins; deriving from the sample a profile data set, the profile data set including a plurality of members, each member being a quantitative measure of the amount of a distinct RNA or protein constituent in a panel of constituents selected so that measurement of the constituents enables measurement of the biological condition; wherein such measure is performed for each constituent under conditions wherein efficiencies of amplification for all constituents are substantially similar, the profile data set providing a measure of the biological condition as affected by the agent.

Efficiencies of amplification of all constituents may differ by less than approximately 2%. The efficiencies of amplification may differ by less than approximately 1%. Moreover, in any of the embodiments of the invention described above which refers to a panel, the panel may include at least four constituents selected from any one of Tables 1 through 7. For example, at least four constituents may be selected from the group consisting of expression products of TNF-α, IL-1-α, IL-β, IFN-γ, IL-8, and IL-10.

In another embodiment of the invention, a kit is provided having primer-probe combinations for measuring expression products of at least four constituents selected from any one of Tables 1 through 7. The kit may further include a primer probe combination constructed so as to hybridize only to at least one of cDNA and mRNA at a biologically relevant locus. Moreover, in each combination, a reverse primer may be selected which is complementary to a coding DNA strand located across an intron-exon junction, with not more than three bases of a three-prime end of the reverse primer being complementary to a proximal exon.

BRIEF DESCRIPTION OF THE DRAWINGS

The foregoing features of the invention will be more readily understood by reference to the following detailed description, taken with reference to the accompanying drawings, in which:

FIGS. 27(a) through 27(d) illustrate calibrated profile data sets, using a subset of the Inflammation Selected Panel, providing a comparison of the effects of administration of methylprednisolone and Ibuprofen.

FIGS. 29(a) and 29(b) provide illustrations in which evaluations of the effects of drug exposure performed in vitro correspond closely with evaluations performed in vivo, employing in each case calibrated profile data sets, using a subset of the Inflammation Selected Panel.

FIG. 30 illustrates the effect of different agents evaluated using a subset of the Selected Prostate Panel, and shows broad functions of constituents of the panel.

FIG. 36 illustrates the protective effect of the antioxidant n-acetylcysteine (NAC) on human keratinocytes in culture after exposure the UVB energy. The dark bars indicate the effect of UVB exposure only. Cells that were treated with NAC followed by exposure to the same UVB energy show a decreased induction of expression at most of the gene loci covered by the skin selected panel. The baseline corresponds to cells exposed to assay media only.

DETAILED DESCRIPTION OF SPECIFIC EMBODIMENTS

Figure 1:
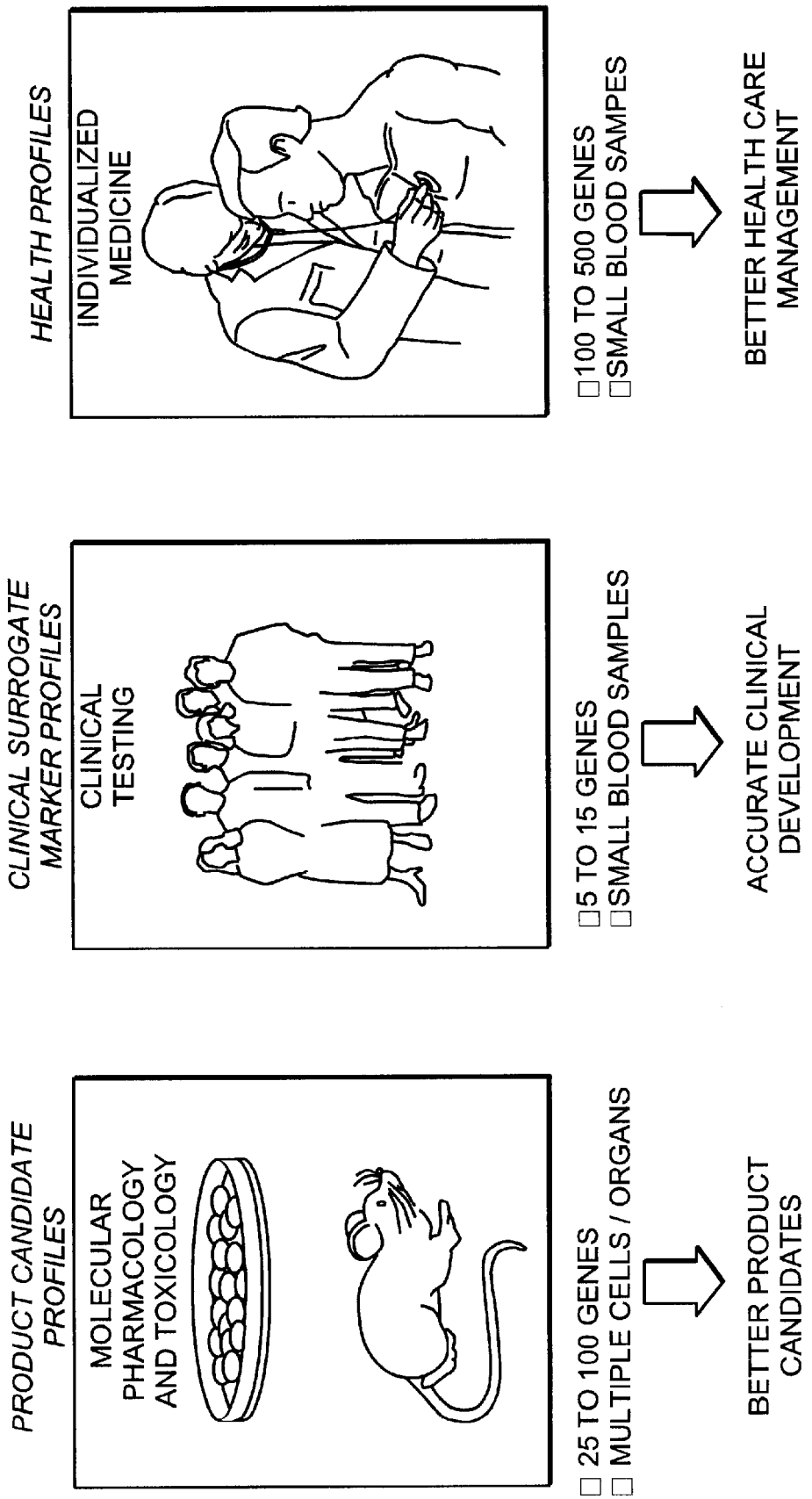
FIG. 1 is a diagram showing the flow of information from data acquired in molecular pharmacology and toxicology, clinical testing, and use of the data for the application to individualized medicine.

As used in this description and the accompanying claims, the following terms shall have the meanings indicated, unless the context otherwise requires:

A "collection of cells" is a set of cells, wherein the set has at least one constituent.

A "population of cells" includes one or more cells. A population of cells may refer to cells in vivo or to in vitro cultures. In vitro cultures may include organ cultures or cell cultures where cell cultures may be primary or continuous cell cultures of eukaryotic or prokaryotic cells. Cell lines can be primary cultures or cell samples, e.g. from a tumor, from blood or a blood fraction, or biopsy explants from an organ, or can be established cell lines or microbial strains.

A "region of the subject" from which proteins are obtained may (but is not required to be) the same part of the subject from which has been obtained a collection of cells or a population of cells. The cells and the proteins may both be obtained from blood of the subject, for example. Alternatively, for example, the cells may be obtained from blood and the proteins may be obtained from a scraping of tissue or vice versa. Similarly, the proteins may be obtained from urine of the subject, for example, whereas the cells may obtained elsewhere, as, for example, from blood.

A "panel" of genes is a set of genes including at least two constituents.

A "normative" condition of a subject to whom a composition is to be administered means the condition of a subject before administration, even if the subject happens to be suffering from a disease.

An "expression" of a gene includes the gene product whether RNA or protein resulting from translation of the messenger RNA.

A "large number" of data sets based on a common panel of genes is a number of data sets sufficiently large to permit a statistically significant conclusion to be drawn with respect to an instance of a data set based on the same panel.

A "biological condition" of a subject is the condition of the subject in a pertinent realm that is under observation, and such realm may include any aspect of the subject capable of being monitored for change in condition, such as health, disease including cancer; trauma; aging; infection; tissue degeneration; developmental steps; physical fitness; obesity, or mood. As can be seen, the conditions may be chronic or acute or simply transient. Moreover, a targeted biological condition may be manifest throughout the organism or population of cells or may be restricted to a specific organ (such as skin, heart, eye or blood). The term "biological condition" includes a "physiological condition".

The "blind administration" of a selected one of a composition or placebo to a subject in a clinical trial involves administering the composition or placebo to the subject in accordance with a protocol pursuant to which the subject lacks knowledge whether the substance administered is the composition or a placebo.

An "organism" is any living cell including microorganisms, animals and plants. An animal is commonly in this context a mammal, but may be a vertebrate non-mammal, as e.g., a zebra fish, or an invertebrate, as, e.g. *Caenorhabditis elegans*.

An "agent" is a composition or a stimulus. A "stimulus" may include, for example ultraviolet A or B, or light therapy for seasonal affective disorder, or treatment of psoriasis with psoralen or treatment of melanoma with embedded radioactive seeds, other radiation exposure, etc. A "composition" includes a chemical compound, a nutraceutical, a combination of compounds, or a complex mixture.

A "clinical indicator" is any physiological datum used alone or in conjunction with other data in evaluating the physiological condition of a collection of cells or of an organism. This term includes pre-clinical indicators.

A "selected panel" is an experimentally verified set of constituents, each constituent being a distinct expressed product of a gene, whether RNA or protein, wherein constituents of the set are selected so that their measurement provides a measurement of a targeted biological condition A "selected profile" is a set of values associated with constituents of a selected panel resulting from evaluation of a biological sample (or population of samples).

A "signature profile" is an experimentally verified subset of a selected profile selected to discriminate a biological condition, agent or physiological mechanism of action. A "signature panel" is a subset of a selected panel, the constituents of which are selected to permit discrimination of a biological condition, agent or physiological mechanism of action.

"Distinct RNA or protein constituent" in a panel of constituents is a distinct expressed product of a gene, whether RNA or protein.

An embodiment of the invention includes the formation of calibrated data sets that describe a biological condition or an effect of an agent on a biological condition. A calibrated data set represents a set of values that correspond to variations in gene expression where the variations are informative. This approach does not require comprehensive analysis of all gene expression in target cells associated with a particular condition. Nor is any one single gene locus necessarily of particular significance. Rather a pattern of variation (a profile) is sought that correlates, in a reproducible manner, with a particular condition. There may be no a priori knowledge of a correlation but rather a correlation may be established by evaluating a panel of constituents of reasonable size (for example up to 100 constituents) and iteratively testing the gene expression profiles for different subjects or for the same subject from which the most informative loci for a particular condition may be selected. An informative subgroup of constituents in a panel may be selected that consistently vary for a particular condition and this subgroup may then become the signature panel, the signature panel giving rise to a signature profile.

In further embodiments of the invention, any calibrated data set for an individual that has more members than reflective of a single signature panel may be mined for calibrated profiles that correspond to additional signature panels, thereby potentially providing new insights into mechanisms of action of a biological condition on sets of genes. Measurement of changes in transcribed RNA in a cell as a result of an environmental change or aging is an exquisitely sensitive measure of the response of a cell. Techniques available today to quantify transcribed RNA in a cell add to the sensitivity of the approach. Embodiments of the invention that are directed to patterns of change in amounts of transcribed RNA provide a means to focus and interpret this rich information.

In contrast to the above approach, much attention in the prior art has been directed to the sequencing of the human genome and the identification of all the genes encoded therein. Accompanying the growing amount of sequence data, microarrays provide a means to survey many hundreds to thousands of gene sequences. Microarrays are being used to provide DNA profiles that identify mutations in an individual and those mutations will be associated with predictions concerning development of disease in those individuals.

Transcriptomics and proteomics are now the focus of increasing attention. These studies are directed to analyzing the entire body of RNA and protein produced by living cells. Microarrays provide a method for analyzing many thousands of different human RNAs as to whether they are expressed and by which cells. For example, a project undertaken by the National Cancer Institute and others to examine mRNAs produced by various types of cancer cells, have revealed 50,000 genes that are active in one or more cancers. The goal of these studies is to identify novel cancer drugs that are directed to knocking out or enhancing the production of certain proteins. (Kathryn Brown, The Human Genome Business Today, Scientific American, July 2000, p.50; Julia Karow, The "Other" Genomes, Scientific American, July 2000, p.53; Ken Howard, "The Bioinformatics Gold Rush, Scientific American, July 2000, p.58; Carol Ezzell, Beyond the Human Genome, Scientific American, July 2000, p.64; all incorporated by reference.) Major efforts in correlating genetic variation of individuals and the functional interrelationships of genes in health and disease are being conducted in a variety of consortia including the single nucleotide polymorphism consortium and the Human Epigenome Consortium (Beck et al. Nature Bio-Technology 17 (1999) p 1144). The Epigenome Consortium plans to analyze sets of genome fragments from both healthy and diseased individuals in the 500 different human tissues (Bioworld International: Dec. 22, 1999). This approach seeks to correlate absolute expression of genes associated with a particular condition with the presence of that condition. Examples of prior art that seek to measure gene expression in absolute amounts including by subtractive methods or by determining amounts with respect to housekeeping genes or by targeting a single gene expression system are U.S. Pat. No. 5,643,765; U.S. Pat. No. 5,811,231; U.S. Pat. No. 5,846,720; U.S. Pat. No. 5,866,330; U.S. Pat. No. 5,968,784; U.S. Pat. No. 5,994,076; WO 97/41261; WO 98/24935; WO 99/11822; WO 99/44063; WO 99/46403; WO 99/57130; WO00/22172 and WO/11208.

We have taken a different and novel approach to the above by identifying reproducible patterns of gene expression that are informative by virtue of the degree of variation between a sample and a baseline, for example, in a subject with the condition and a subject without the condition. The variations may be correlated with other non-genetic indications such as clinical indicators (for humans) of a traditional nature but are not required per se to be causative. Accordingly, the amount of gene expression product (for example RNA transcript) produced by a gene locus in a cell under certain circumstances is measured and then stored as a value in a first profile data set. This value is calibrated with respect to a second value (a baseline profile data set) to provide a member of a calibrated profile data set. The values recorded for the profile data set, relying on a particular baseline data set to produce a calibrated data set, become part of the descriptive record; any or all of these results can be stored in a database which may be accessed through a global network. In this way any new data in the form of a profile data set or a calibrated profile data set measured at any global location can be directly compared to an archive of descriptive records including calibrated profile data sets and baseline data sets so as to extend the stored library of profiles and provide predictive, diagnostic, or evaluative data about a particular biological condition or agent.

We have exemplified the use of selected panels of constituents corresponding to gene loci from which quantitative gene expression is determined by, for example, quantitatively measuring the transcribed RNA in a sample of a subject, for applications that include: (a) measurement of therapeutic efficacy of natural or synthetic compositions or stimuli that may be formulated individually or in combinations or mixtures for a range of targeted physiological conditions; (b) predictions of toxicological effects and dose effectiveness of a composition or mixture of compositions for an individual or in a population; (c) determining how two or more different agents administered in a single treatment might interact so as to detect any of synergistic, additive, negative, neutral or toxic activity (d) performing pre-clinical and clinical trials by providing new criteria for pre-selecting subjects according to informative profile data sets for revealing disease status and conducting preliminary dosage studies for these patients prior to conducting phase 1 or 2 trials. Gene expression profiling may be used to reduce the cost of phase 3 clinical trials and may be used beyond phase 3 trials; (e) labeling for approved drugs; (f) selection of suitable medication in a class of medications for a particular patient that is directed to their unique physiology; (g) diagnosing or determining a prognosis of a medical condition or an infection which may precede onset of symptoms or alternatively diagnosing adverse side effects associated with administration of a therapeutic agent; (h) managing the health care of a patient; and (i) quality control for different batches of an agent or a mixture of agents.

The Subject

The methods herein can be applied to a subject that includes any living organism where a living organism includes a prokaryote such as a bacterium or a eukaryote including single celled eukaryotic organisms at one end of the spectrum and humans at the other and everything in between including plants. The figures relate to calibrated profile data sets obtained from humans and mammals. Nonetheless, the methods disclosed here may be applied to cells of other organism without the need for undue experimentation by one of ordinary skill in the art because all cells transcribe RNA and it is known in the art how to extract RNA from all types of cells.

A tissue sample may include a single cell or multiple cells or fragments of cells. Body fluid includes blood, urine, spinal fluid, lymph, mucosal secretions, hemolymph or any other body fluid known in the art for a subject. For an animal subject, a tissue or fluid sample may be obtained by means of a biopsy needle aspirate, a lavage sample, scrapings and surgical incisions or other means known in the art.

Selected Panels

Figure 20:
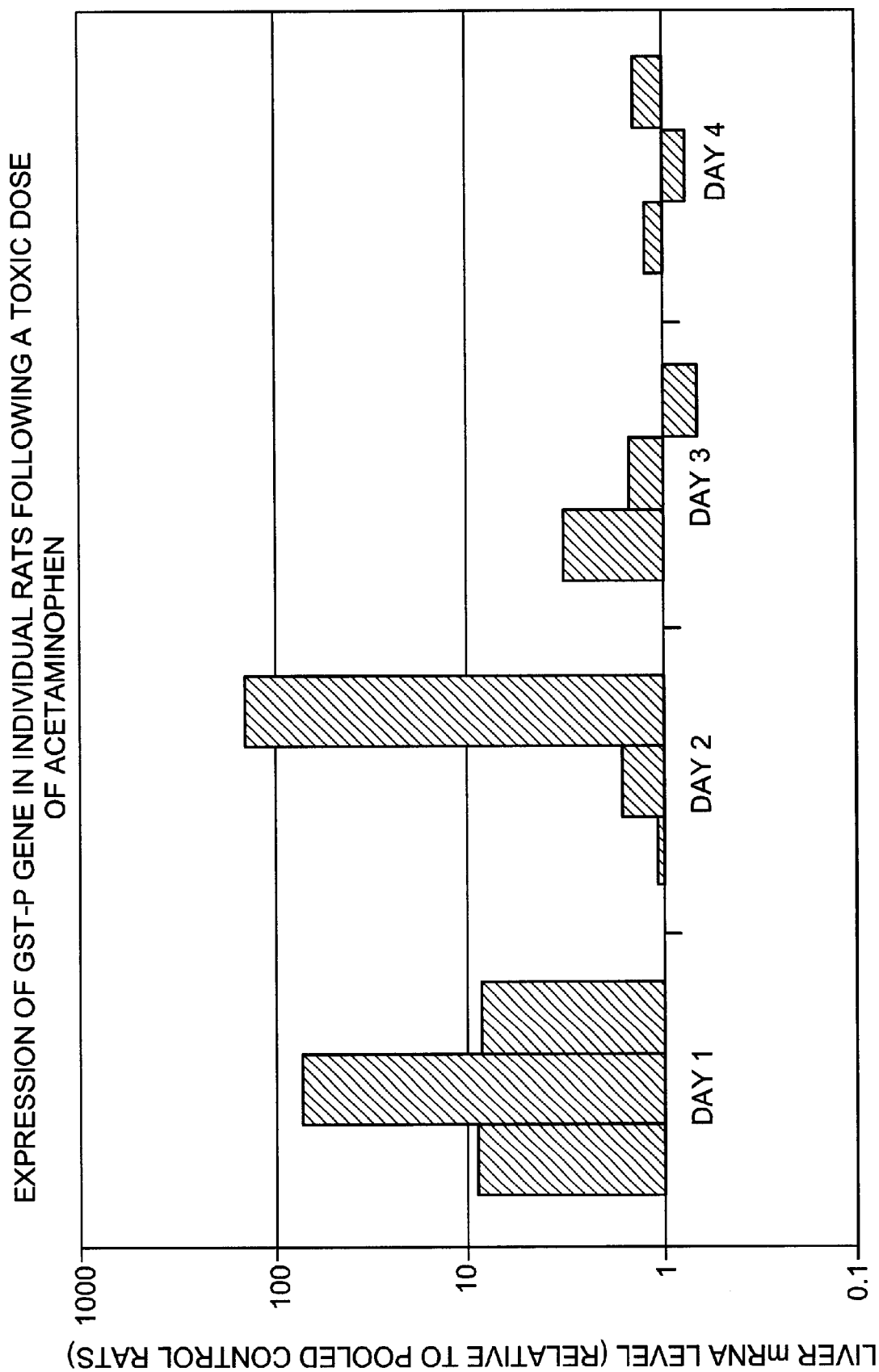
FIG. 20 illustrates that an individual responses can be distinguished from a similarly treated population. A comparison of the response of a single animal compared to its experimental cohort (n=5 animals) with respect to a single locus (GST-P) is provided. The baseline data set is the cohort average. The figures shows that this animal varied significantly from the daily, population average in the first two days of the study, but became more similar to the cohort average with time after treatment with acetamrinophen.
Figure 22:
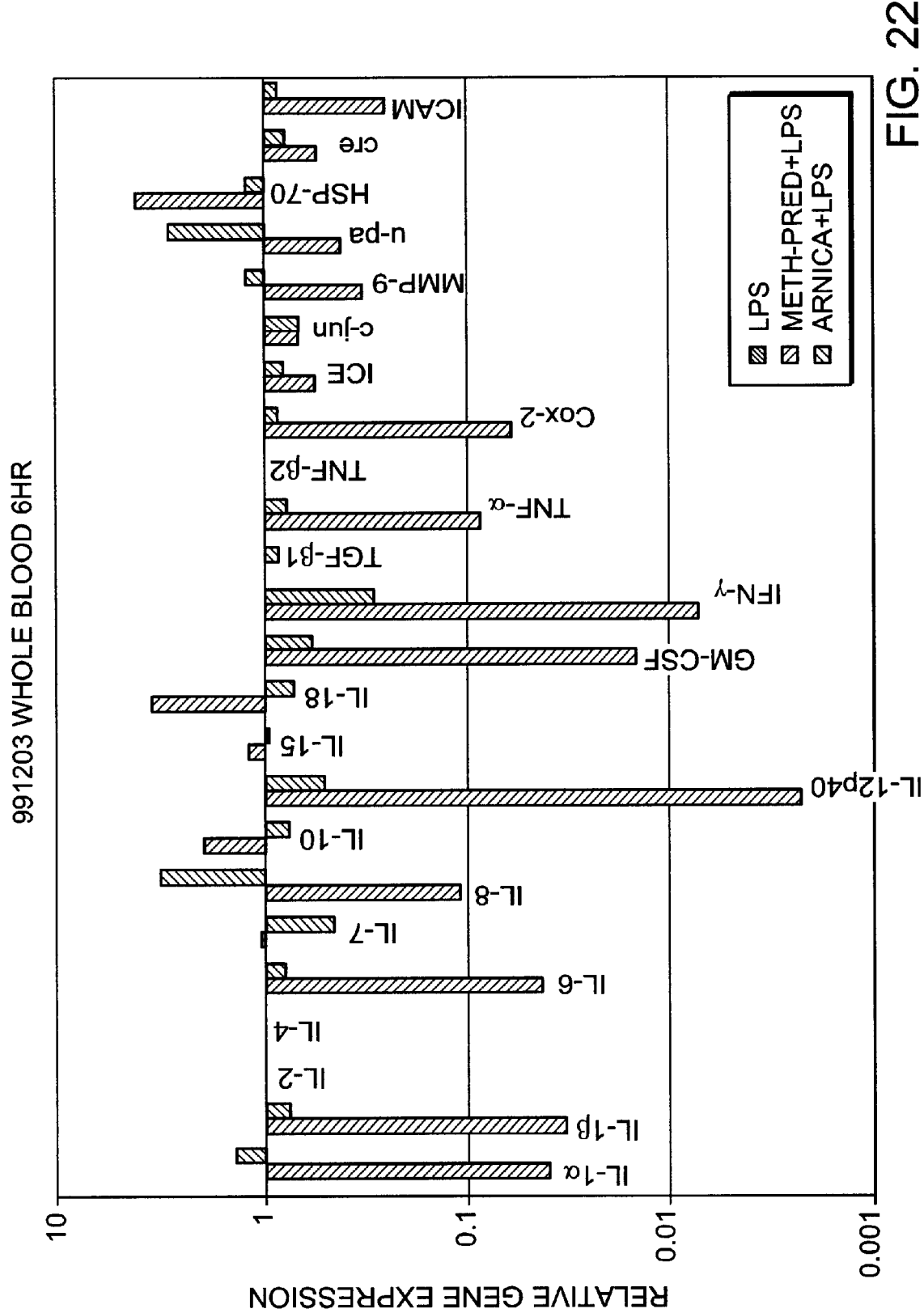
FIG. 22 is a bar graph with a logarithmic axis that shows a graphical representation of calibrated profile data sets for samples of blood treated ex vivo with LPS or LPS and methylprednisolone or LPS and Arnica. The baseline profile data set is LPS treated blood sample.
Figure 23:
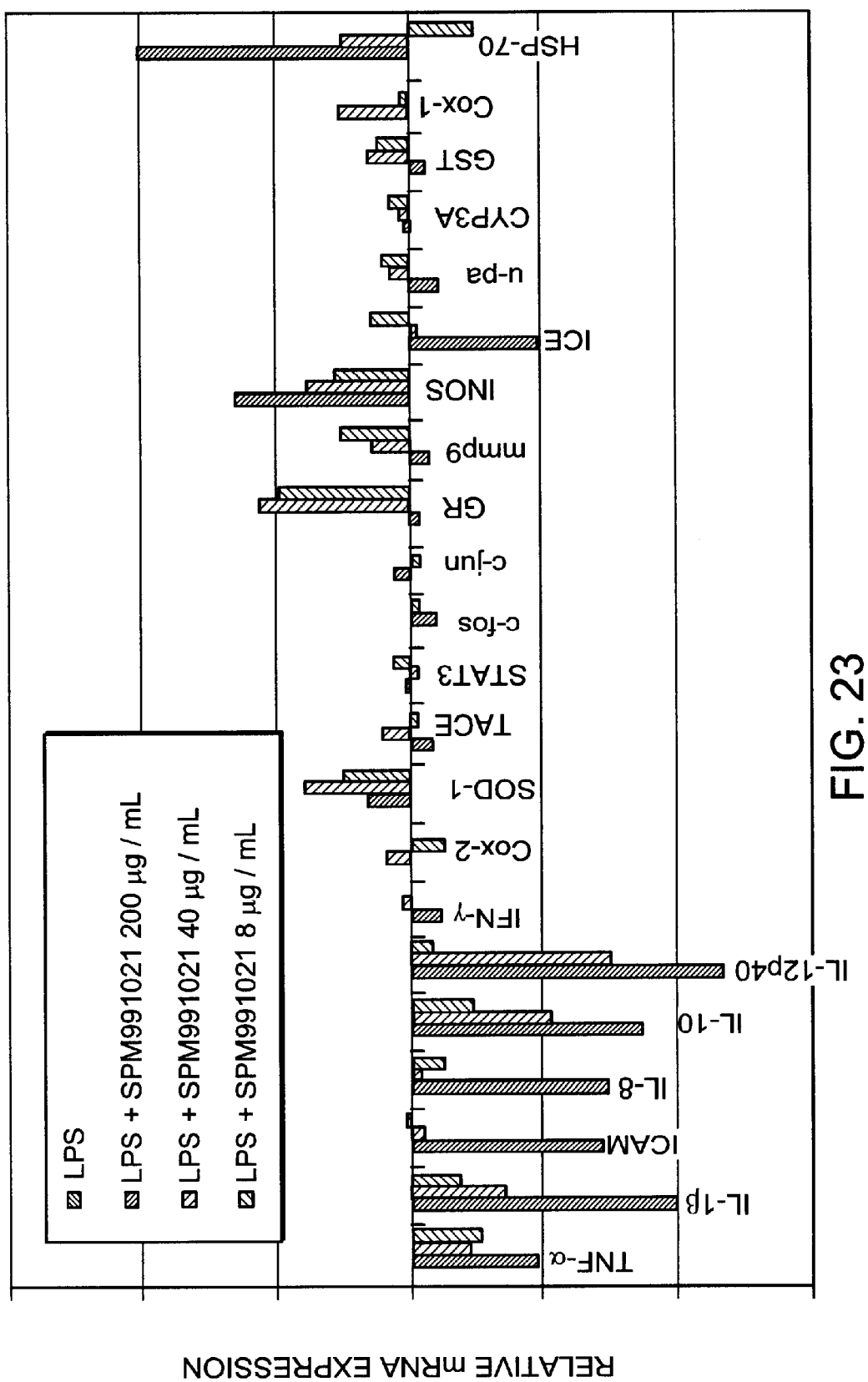
FIG. 23 is a bar graph with a logarithmic axis that shows a graphical representation of calibrated profile data sets for samples of THP-1 cells treated with LPS or LPS and Arnica at three different concentrations using a panel of 22 constituents. The baseline profile data set is untreated THP-1 cells. The figure illustrates a concentration response with respect to the gene expression across the calibrated profile.

Steps in selecting constituents in a selected panel may include searching publicly available medical literature for RNA or proteins or sets of RNAs or proteins that directly or indirectly vary with a particular biological condition. A selected panel containing up to 100 constituents may be selected. According to the condition being examined, just a small subset of the selected panel constituents may be informative. In determining membership of the selected panel of genes, it is not necessary for the panel to be an exhaustive selection. Rather it is desired to obtain from the selected panel an expression profile that discriminates consistently with respect to the targeted physiological or biological condition. Moreover, a selected panel is not necessarily selected according to an expected profile of gene expression in cells that directly respond to a biological effect. For example, gene expression associated with liver metabolism may be analyzed in a blood sample. FIGS. 20 and 22 provide calibrated profiles of whole blood treated with herbal agents using markers for liver metabolism.

The number of constituents in a selected panel can vary. According to the examples provided below, selected panels of up to 24–96 genes are selected for evaluating expression levels. Although a selected panel may be as large as 100 constituents, it is desirable for a particular selected panel to have no more than 24 constituents, more particularly, less than 12 constituents. For example, subsets of no more than 8 genes have been used that may be derived from a larger panel but which are sufficiently informative to effectuate discrimination. The number of constituents in a selected panel for which expression is monitored may vary widely depending on the context. For example, FIG. 1 describes data acquisition from in vitro cell culture and from animal toxicology studies, which includes expression of about 25 to 100 or more genes. In contrast, selection of markers or surrogate markers include, for example, three to 100 genes, preferably five to 50 or five to 25 genes to be analyzed from samples obtained in clinical studies. In this manner markers or surrogate markers having predictive value for a medical condition, such as a genetic predisposition, a response to therapeutic agent, an inflammatory condition, or an infection, etc. can be identified and cumulatively larger populations can be obtained to refine the correlations. A health profile can then be generated for an individual subject using a low volume blood sample. The blood sample can be analyzed for expression profile data of about 100–500 genes, comprising markers or surrogate markers of a number of medical conditions (FIG. 1: right panel). Selected panels of varying sizes may be utilized as necessary and subsequent refinements in methodology may lead to selection of subsets having selected panels as large as 15 genes or 12 genes or as small as 6, 5, 4, 3 or 2 genes.

We have found that we can measure concentrations of constituents in selected panels in a manner that is both highly precise and reproducible in samples taken from the same individual under the same conditions. We have similarly found that such concentration measurements are reproducible in samples that are repeatedly tested.

We commonly run a sample through a panel in quadruplicate; that is, a sample is divided into aliquots and for each aliquot we measure concentrations of each constituent in a selected panel. Over a total of 900 constituent assays, with each assay conducted in quadruplicate, we found an average coefficient of variation, (standard deviation/average)* 100, of less than 1 percent among results for each assay. This figure is a measure of what we call "intra-assay variability". We have also conducted assays on different occasions using the same sample material. With 72 assays, resulting from concentration measurements of constituents in a panel of 24 members, and such concentration measurements determined on three different occasions over time, we found an average coefficient of variation of less than 2 percent. We regard this as a measure of what we call "inter-assay variability".

We have found it valuable in using the quadruplicate test results to identify and eliminate data points that are statistical "outliers"; such data points are those that differ by a percentage greater, for example, than 3% of the average of all four values and that do not result from any systematic skew that is greater, for example, than 1%. Moreover, if more than one data point in a set of four is excluded by this procedure, then all data for the relevant constituent is discarded.

As discussed in further detail below under "Gene Expression", we have found it valuable to optimize the efficiency of amplification for all constituents of a panel in a manner to achieve comparable amplification efficiencies (that is, amplification efficiencies that are substantially similar as described below under "Gene Expression") for all constituents, so that precise quantification of gene expression of all panel constituents may be determined consistently on successive occasions. In this manner, there may result data that is useful because it is precise and reliable.

What this approach means, among other things, is that by utilizing a relatively small panel, and by controlling amplification efficiency and other parameters, we create a panel that is uniquely informative. This approach differs from prior art endeavors where specificity is optimized only on a per-constituent basis and reaction conditions are not optimized for the panel as a whole.

It is envisaged that any single biological condition may be described by a signature panel having a small number of highly informative constituents providing a signature calibrated profile (also referred to as a fingerprint). The presence of highly informative loci is demonstrated in several of the accompanying figures. For example, FIG. 11 (a) Il-2, Il-4 and Il-5 are highly informative. Highly informative constituents in FIG. 21 include the pro-inflammatory—interleukins. The signature panel may provide a signature profile or fingerprint which is sufficiently robust to serve as a standard in describing a particular biological condition or an effect of a particular agent on a biological condition For purposes of illustrating a signature panel, constituents of a selected panel for measuring inflammation have been provided that are informative with respect to a particular biological condition. For example, we have used a selected panel for inflammation that has 6 constituents—Il-1$\alpha$, Il-6, Il-8, Il-18, GMCSF and IFN-$\gamma$ in FIGS. 18($a$)–($e$) to determine the response of 5 subjects to varying concentrations of drugs. This group of constituents is a subset of a larger selected panel of inflammation related gene loci such as shown in FIG. 19$a$ and FIG. 19$b$ where the Inflammation Selected Panel includes Il-$\alpha$, Il-$\beta$, Il-2, Il-3, Il-4, Il-6, Il-7, Il-8, Il-10, Il-12p40, Il-15, Il-15, Il-18, GM-CSF, Ifn-gamma, TGF-$\beta$, cox-2, ICE, MMP-9, ICAM, TNF-$\alpha$ and TNF-$\beta$. The subset of constituents were selected on the basis of the information sought concerning the biological condition.

Embodiments of the invention provide examples of numerous different selected panels which may be used separately or together. These selected panels include an Inflammation Selected Panel (Table 1) a Cell Growth and Differentiation Selected Panel (Table 2), a Liver Metabolism and Toxicity Selected Panel (Table 3). We have developed additional selected panels including Skin Response Selected Panel (Table 4), Prostate Selected Panel (Table 5)(for measuring prostate health and disease), Vascular Selected Panel (Table 6)(for measuring condition of the vascular system and endothelial cells). It is a significant property of each of these selected panels that measurement of the selected panel's constituents provides a measurement of the physiological condition to which the selected panel is targeted. Selected panels may also provide useful information concerning gene response outside the target condition. In these tables the left-hand column identifies the particular gene loci, and the right-hand column describes proteins expressed by these loci. However, as described in detail below, embodiments of the present invention may utilize, for example, mRNA or protein expression products as constituents. While below we provide examples based primarily on the Inflammation Selected Panel and subsets of it, the approaches set forth herein are equally applicable to the other selected panels described above. Although provided as examples, the above selected panels are not intended to be limiting.

Gene Expression

For measuring the amount of a particular RNA in a sample, we have used methods known to one of ordinary skill in the art to extract and quantify transcribed RNA from a sample with respect to a constituent of a selected panel (See detailed protocols below.) Briefly, RNA is extracted from a sample such as a tissue, body fluid (see Example 11 below), or culture medium in which a population of a subject might be growing. For example, cells may be lysed and RNA eluted in a suitable solution in which to conduct a DNAse reaction. First strand synthesis (see Example 10 below) may then be performed using a reverse transcriptase. Gene amplification, more specifically quantitative PCR assays, can then be conducted and the gene of interest size calibrated against a marker such as 18S rRNA (Hirayama et al., Blood 92, 1998: 46–52). Samples are measured in multiple duplicates, for example, 4 replicates. Relative quantitation of the mRNA is determined by the difference in threshhold cycles between the internal control and the gene of interest (see Example 12 below). In an embodiment of the invention, quantitative PCR is performed using amplification, reporting agents and instruments such as those supplied commercially by Applied Biosystems (Foster City, Calif.). Given a defined efficiency of amplification of target transcripts, the point (e.g., cycle number) that signal from amplified target template is detectable may be directly related to the amount of specific message transcript in the measured sample. Similarly, other quantifiable signals such as fluorescence, enzyme activity, disintegrations per minute, absorbance, etc., when correlated to a known concentration of target templates (e.g., a reference standard curve) or normalized to a standard with limited variability can be used to quantify the number of target templates in an unknown sample.

Although not limited to amplification methods, quantitative gene expression techniques may utilize amplification of the target transcript. Alternatively or in combination with amplification of the target transcript, amplification of the reporter signal may also be used. Amplification of the target template may be accomplished by isothermic gene amplification strategies, or by gene amplification by thermal cycling such as PCR.

It is desirable to obtain a definable and reproducible correlation between the amplified target or reporter and the concentration of starting templates. We have discovered that this objective can be achieved by careful attention to, for example, consistent primer-template ratios and a strict adherence to a narrow permissible level of amplification efficiencies (for example 99.8 to 100% relative efficiency). For example, in determining gene expression levels with regard to a single selected profile, it is necessary that all constituents of the panels maintain a similar and limited range of primer template ratios (for example, within a 10-fold range) and amplification efficiencies (within, for example, less than 1%) to permit accurate and precise relative measurements for each constituent. We regard amplification efficiencies as being "substantially similar", for the purposes of this description and the following claims, if they differ by no more than approximately 10%. Preferably they should differ by less than approximately 2% and more preferably by less than approximately 1%. These constraints should be observed over the entire range of concentration levels to be measured associated with the relevant biological condition. In practice, we run tests to assure that these conditions are satisfied. For example, we typically design and manufacture a number primer-probe sets, and determine experimentally which set gives the best performance. Even though primer-probe design and manufacture can be enhanced using computer techniques known in the art, and notwithstanding common practice, we still find that experimental validation is useful. Moreover, in the course of experimental validation, we associate with the selected primer-probe combination a set of features:

(i) The reverse primer should be complementary to the coding DNA strand; located across an intron-exon junction, with not more than three bases of the three-prime end of the reverse primer complementary to the proximal exon. (If more than three bases are complementary, then it would tend to competitively amplify genomic DNA.)

(ii) The primer probe should amplify cDNA of less than 10 bases in length.

(iii) The primer probe should not amplify genomic DNA or transcripts or cDNA from related but biologically irrelevant loci.

A suitable target of the selected primer probe is first strand cDNA, which may be prepared, in one embodiment, according to Example 1 below. In Example 11 below, we illustrate use of the primer probe with the first strand cDNA of Example 1 to permit measurement of constituents of a selected panel.

It is envisaged that techniques in the art using microfluidics for example and highly sensitive markers will enable quantitation of RNA to occur directly from a single cell or lysed cell. This may rely on amplification of a marker but may not require amplification of the transcripts themselves. The amount of transcript measured for any particular locus is a data point or member of the first profile data set for a particular selected panel.

According to embodiments of the invention, a first profile data set is derived from the sample, the first profile data set including a plurality of members, each member being a quantitative measure of the amount of a RNA transcribed from a gene locus, the gene locus being a constituent in a panel of constituents. A first profile data set may be obtained from a quantitative measure of the amount of a distinct RNA or protein corresponding to a gene locus. The figures provided here are directed to RNA. However, methods herein may also be applied using proteins where sensitive quantitative techniques, such as an Enzyme Linked ImmunoSorbent Assay (ELISA), are available and well-known in the art for measuring the amount of a protein constituent.

Baseline Profile Data Sets

The analyses of samples from single individuals and from large groups of individuals provide a library of profile data sets relating to a particular panel or series of panels. These profile data sets may be stored as records in a library for use as baseline profile data sets. As the term "baseline" suggests, the stored baseline profile data sets serve as comparators for providing a calibrated profile data set that is informative about a biological condition or agent. Baseline profile data sets may be stored in libraries and classified in a number of cross-referential ways. One form of classification may rely on the characteristics of the panels from which the data sets are derived. Another form of classification may be by particular biological condition. The concept of biological condition encompasses any state in which a cell or population of cells may be found at any one time. This state may reflect geography of samples, sex of subjects or any other discriminator. Some of the discriminators may overlap. The libraries may also be accessed for records associated with a single subject or particular clinical trial. The classification of baseline profile data sets may further be annotated with medical information about a particular subject, a medical condition, a particular agent etc.

The choice of a baseline profile data set for creating a calibrated profile data set is related to the biological condition to be evaluated, monitored, or predicted, as well as, the intended use of the calibrated panel, e.g., as to monitor drug development, quality control or other uses. It may be desirable to access baseline profile data sets from the same subject for whom a first profile data set is obtained or from different subject at varying times, exposures to stimuli, drugs or complex compounds; or may be derived from like or dissimilar populations.

Figure 5:
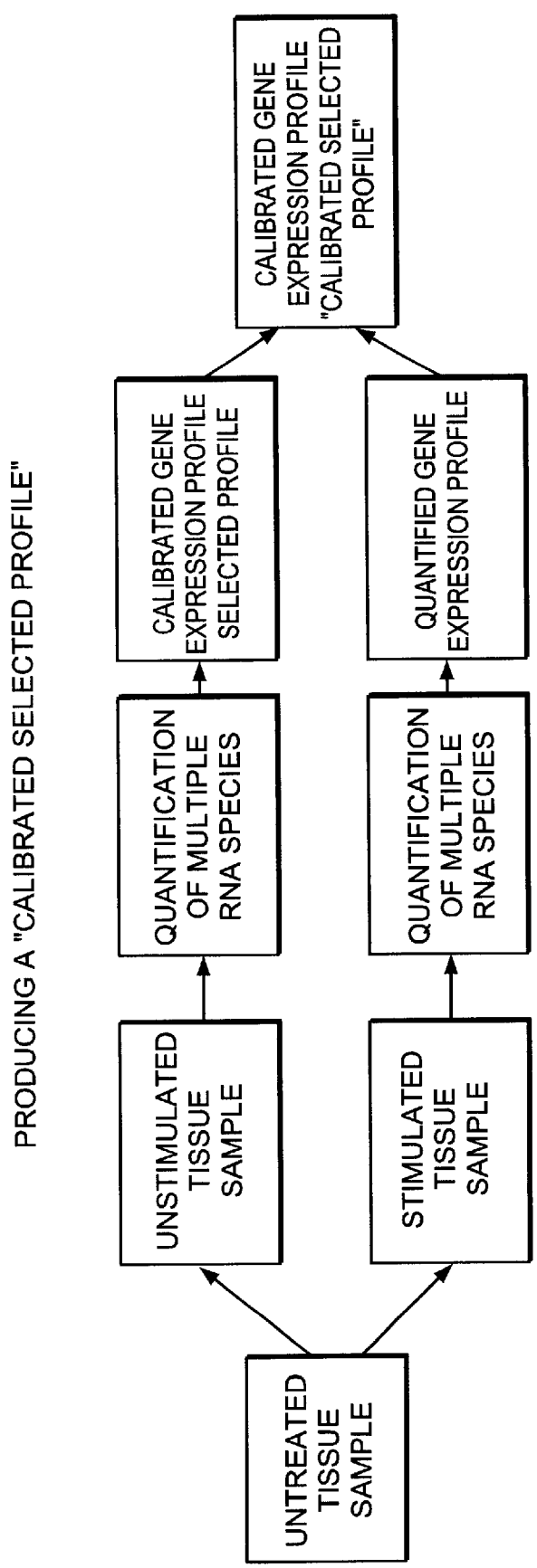
FIG. 5 is a diagram showing a method in accordance with an embodiment of the present invention for obtaining profile data in the absence of a stimulus and in the presence of a stimulus.

The profile data set may arise from the same subject for which the first data set is obtained, where the sample is taken at a separate or similar time, a different or similar site or in a different or similar physiological condition. For example, FIG. 5 provides a protocol in which the sample is taken before stimulation or after stimulation. The profile data set obtained from the unstimulated sample may serve as a baseline profile data set for the sample taken after stimulation. The baseline data set may also be derived from a library containing profile data sets of a population of subjects having some defining characteristic or biological condition. The baseline profile data set may also correspond to some ex vivo or in vitro properties associated with an in vitro cell culture. The resultant calibrated profile data sets may then be stored as a record in a database or library (FIG. 6) along with or separate from the baseline profile data base and optionally the first profile data set although the first profile data set would normally become incorporated into a baseline profile data set under suitable classification criteria.

Selected baseline profile data sets may be also be used as a standard by which to judge manufacturing lots in terms of efficacy, toxicity, etc. Where the effect of a therapeutic agent is being measured, the baseline data set may correspond to gene expression profiles taken before administration of the agent. Where quality control for a newly manufactured product is being determined, the baseline data set may correspond with a gold standard for that product. However, any suitable normalization techniques may be employed. For example, an average baseline profile data set is obtained from authentic material of a naturally grown herbal nutraceutical and compared over time and over different lots in order to demonstrate consistency, or lack of consistency, in lots of compounds prepared for release.

Calibrated Data

Figure 6:
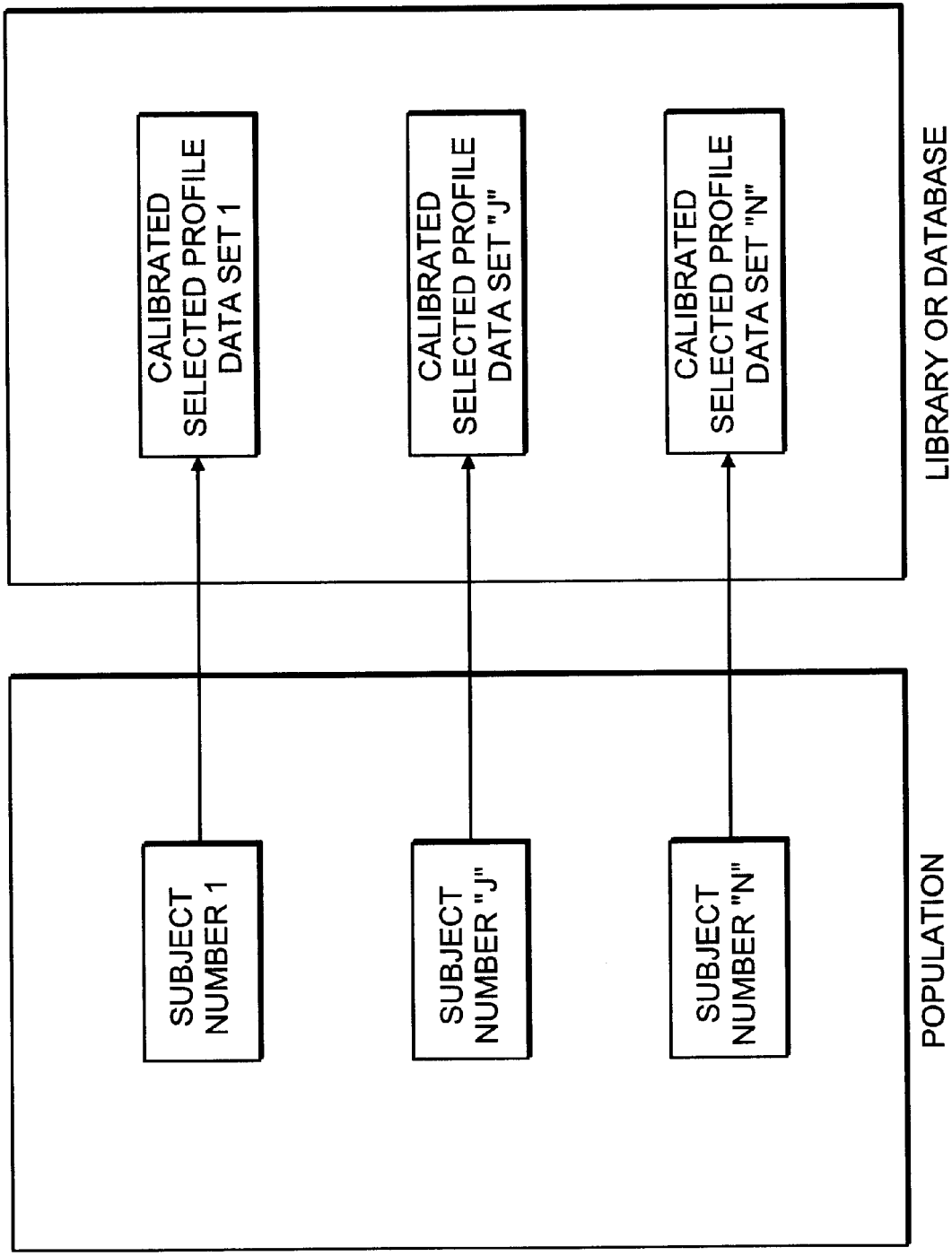
FIG. 6 is a diagram showing the creation of a library of profile data associated with a plurality of subjects in accordance with an embodiment of the present invention.
Figure 14:
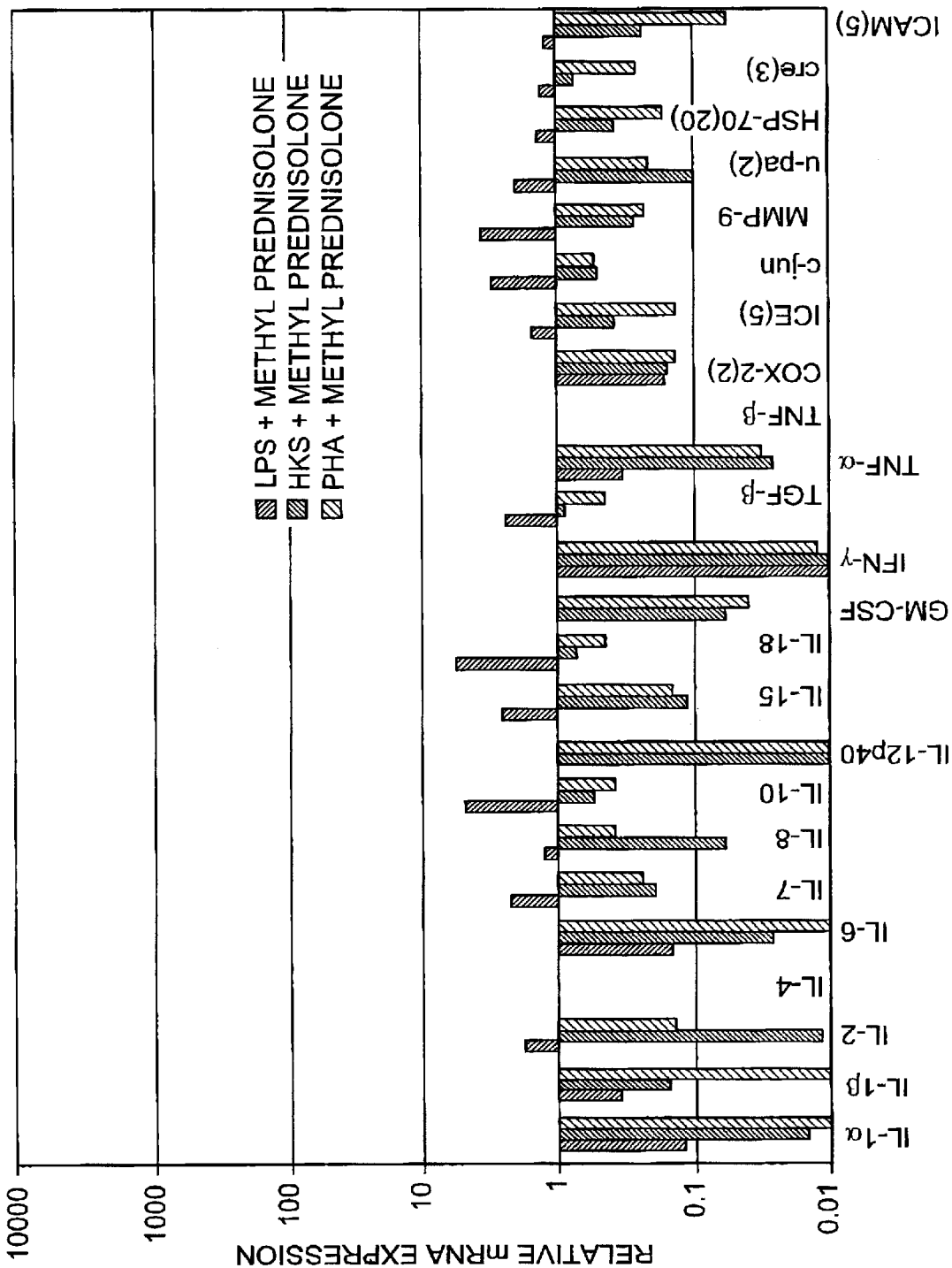
FIG. 14 is a bar graph with a logarithmic axis that shows a graphical representation of calibrated profile data sets using a panel of 22 constituents, each constituent corresponding to a gene locus, the baseline profile data set being derived from untreated cells. Whole blood is exposed for six hours ex vivo to three inflammation inducing agents (lipopolysaccharide, heat killed staphylococci, and phytohemagglutinin) which are then treated with a single anti-inflammatory agent (methyl prednisolone) to reveal similarities and differences in the effect of a single agent on cell populations differing in their biological condition.
Figure 15:
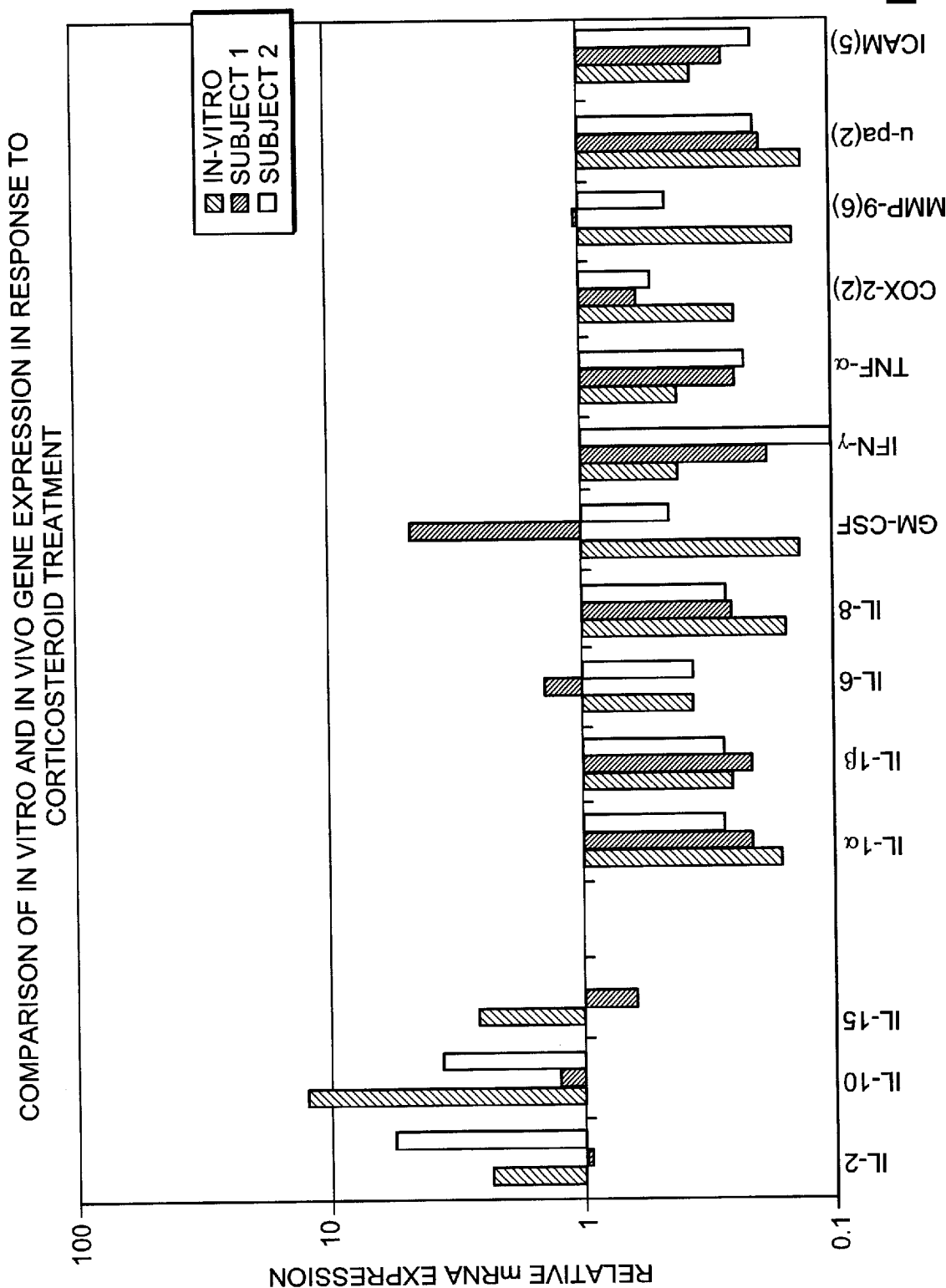
FIG. 15 is a bar graph with a logarithmic axis that shows a graphical representation of calibrated profile data sets for whole blood where one calibrated data set refers to a subject (subject 2) who has been treated in vivo with a corticosteroid (dexamethasone), a second data set refers to the treatment of a blood sample from the same subject prior to in vivo treatment where that sample has been treated ex vivo (in vitro) and the third data set refers to a second subject treated in vivo with dexamethasone (subject 1). The data sets demonstrate the reproducibility and predictability of an ex vivo (in vitro) treatment of blood compared to in vivo treatment with the same agent. The figure also shows minor variation between samples from different subjects reflecting interpersonal variability. A panel of 14 constituents is provided. The baseline profile data set is derived from untreated whole blood from the cognate subject.
Figure 16A:
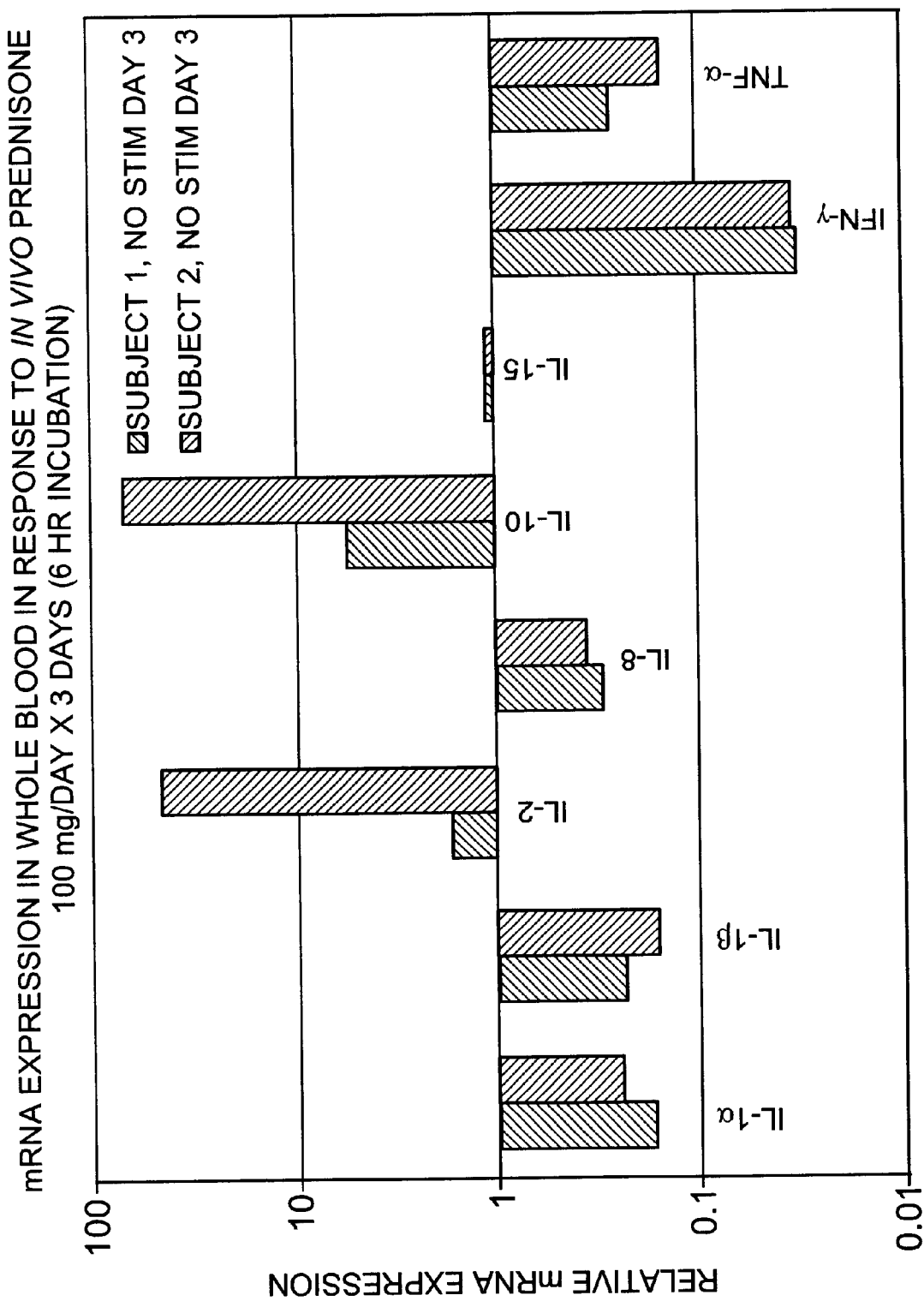
FIG. 16 is a bar graph with a logarithmic y axis that shows a graphical representation of calibrated profile data sets for whole blood where one calibrated data set refers to (a) 2 subjects who have been treated in vivo with an inactive placebo for 3 days and (b) active prednisolone for 3 days at 100 mg/day. The data set shows some variation between samples from different subjects treated with the same drug. The data sets demonstrate similarity of responses across the same gene loci, as well as, quantitative variation at other loci suggesting quantifiable interpersonal variation. A panel of eight members is provided. The baseline profile data set is derived from untreated whole blood.

A calibrated profile data set may be described as a function of a member of a first profile data set and a corresponding member of a baseline profile data set for a given gene locus in a panel. For example, calibrated profile data sets may be derived by calculating a ratio of the amount of RNA transcribed for a panel constituent in a cell sample in an environmental including intervention such as a therapeutic treatment or at a particular time (first profile data set) with respect to the amount of RNA transcribed for the same panel constituent in a cell that differs in some manner from the sample (baseline profile data set) (FIGS. 5 and 6). Given the precision we have achieved in measurement of gene expression, described above in connection with "selected panels" and "gene amplification", we conclude that where differences occur in measurement under such conditions, the differences are attributable to differences in biological condition. Thus we have found that calibrated profile data sets are highly reproducible in samples taken from the same individual under the same conditions. We have similarly found that calibrated profile data sets are reproducible in samples that are repeatedly tested. We have also found repeated instances wherein calibrated profile data sets obtained when samples from a subject are exposed ex vivo to a compound are comparable to calibrated profile data from a sample that has been exposed to a sample in vivo (FIG. 14, FIG. 16(a), (b), and FIGS. 29(a) and 29(b)). We have also found, importantly, that an indicator cell line treated with an agent can in many cases provide calibrated profile data sets comparable to those obtained from in vivo or ex vivo populations of cells (FIG. 15). Moreover, we have found that administering a sample from a subject onto indicator cells can provide informative calibrated profile data sets with respect to the biological condition of the subject including the health, disease states, therapeutic interventions, aging or exposure to environmental stimuli or toxins of the subject (FIG. 25).

A use of a calibrated profile data set is to evaluate a biological condition of a subject. This may be for purposes of diagnosis or prognosis of a clinical disorder. It is desirable to obtain a calibrated data set that describes a state of health or alternatively a state of age or body mass or any condition or state that an individual subject might find themselves to be in. For example, the biological condition may relate to physical activity, conditioning or exercise, mental state, environmental factor such as medication, diet, or geography or exposure to radiation or environmental contamination or infectious agent, biological or environmental toxin. If health or conversely a clinical disorder is being evaluated, calibrated profiles data sets may be used for monitoring change in health status by periodic or regular comparison of profiles; the disorder may be a complex disease process possibly involving multiple gene including inflammation, autoimmune disease, degenerative disease, allergy, vascular disease, ischemia, developmental disease, hormonal conditions and infectious diseases. The clinical disorder may further include arthritis, asthma, multiple sclerosis and perimenopausal changes. The biological condition may affect a system of a subject including a respiratory, vascular, nervous, metabolic, urinary, reproductive, structural and immunological system or other metabolic state. The above examples of a biological condition are given by way of illustration and are not intended to be limiting.

Similarly, calibrated profile data sets may be used to measure, monitor or predict the host response to an infectious agent for purposes of identifying the infectious agent, assessing the duration of infection, the extent of exposure or making therapeutic decisions.

The evaluation of activity of an agent may require a series of calibrated profiles. It is here shown that calibrated profile data sets may be used to describe the biological activity of an agent that may be a single compound or a complex compound such as a nutraceutical or herbal. The agent may be assayed using indicator cells, ex vivo cell populations or by in vivo administration. These assays may rely on a series of signature panels or enlarged panels for different biological conditions. The resultant calibrated profiles may then be used to infer likely in vivo activity from the in vitro study. Insights into toxicity and mechanisms of action can also be inferred from calibration profile data sets. For example, the herbal Echinacea is believed to have both immunostimulatory and anti-inflammatory properties although neither has been measured systematically. We have provided a systematic approach to investigate the biological activities of these and other herbs. We investigated the alleged immunostimulatory properties of the herbs by comparing the effect of treating the indicator cell line THP-1 or peripheral blood cells with the agent to untreated cells. Untreated cells include LPS stimulated untreated cells. Untreated cells were used as a baseline profile data set to measure the difference in gene expression between a baseline profile data set and the experimental treatment with the compound. Baseline profile data sets included a single sample or an average value from a series of experiments. The resultant calibrated profile data sets could then be compared with a library of calibrated profile data sets for a particular herb or/and libraries associated with different agents or conditions.

From the information obtained about a previously undescribed agent, a signature panel may be derived optionally together with a signature profile to serve as a gold standard for testing other batches of the same agent.

Calculation of Calibrated Profile Data Sets and Computational Aids

The function relating the baseline and profile data sets is, in an embodiment of the invention, a ratio expressed as a logarithm. The calibrated profile data set may be expressed in a spreadsheet or represented graphically for example, in a bar chart or tabular form but may also be expressed in a three dimensional representation. The constituent may be itemized on the x-axis and the logarithmic scale may be on the y-axis. Members of a calibrated data set may be expressed as a positive value representing a relative enhancement of gene expression or as a negative value representing a relative reduction in gene expression with respect to the baseline.

Each member of the calibrated profile data set should be reproducible within a range with respect to similar samples taken from the subject under similar conditions. For example, the calibrated profile data sets may be reproducible within one order of magnitude with respect to similar samples taken from the subject under similar conditions. More particularly, the members may be reproducible within 50%, more particularly reproducible within 20%, and sometimes even 10%. In accordance with embodiments of the invention, a pattern of increasing, decreasing and no change in relative gene expression from each of a plurality of gene loci examined in the precision panel may be used to prepare a calibrated profile set that is informative with regards to a biological condition, biological efficacy of an agent treatment conditions or for comparison to populations. Patterns of this nature may be used to identify likely candidates for a drug trial, used in combination with other clinical indicators to be diagnostic or prognostic with respect to a biological condition or may be used to guide the development of a pharmaceutical or nutraceutical through manufacture, testing and marketing.

Figure 8:
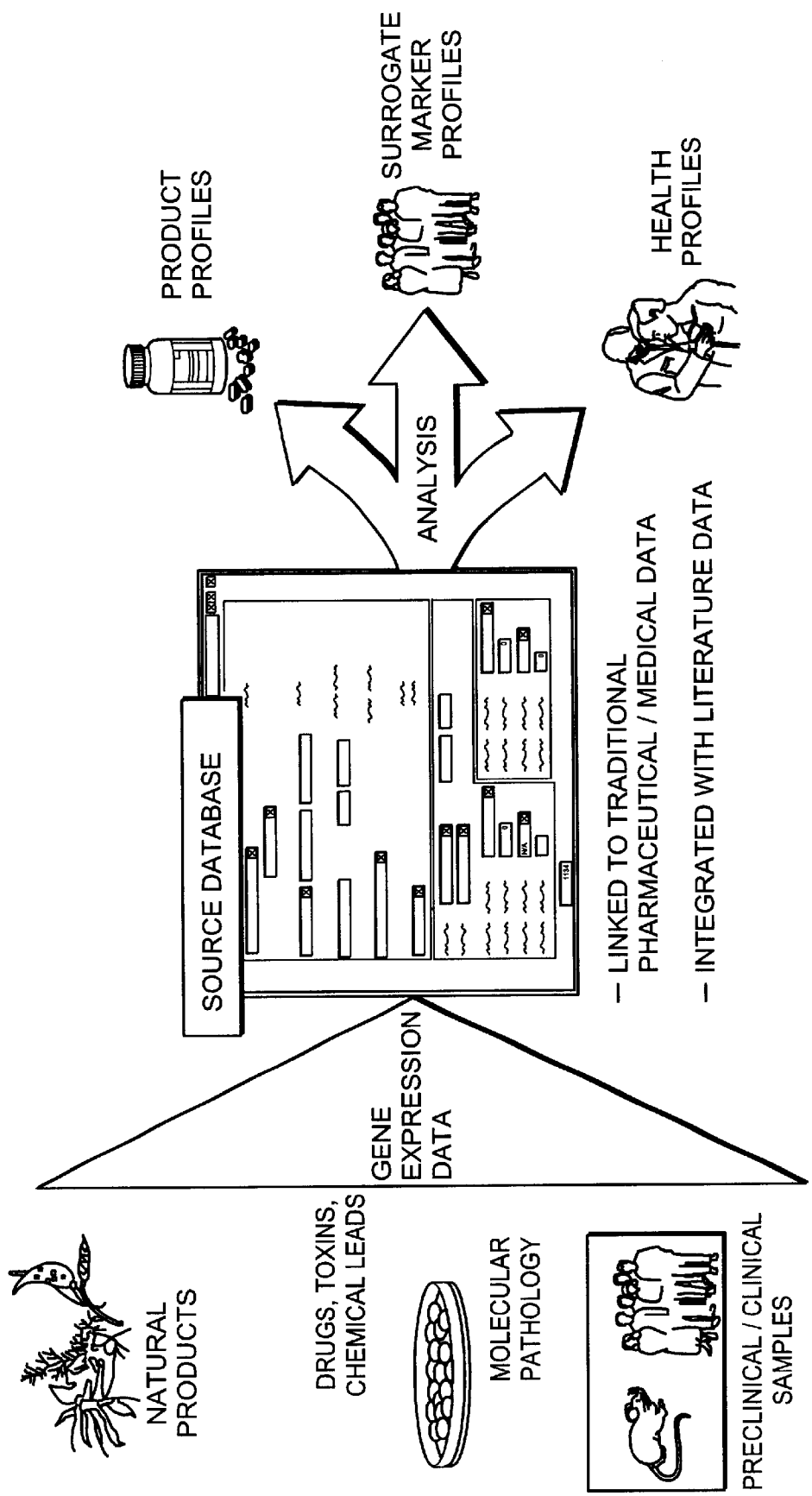
FIG. 8 is a diagram illustrating a data entry screen for a data record of the type shown in FIG. 7 and typical contexts in which data records may be compiled in accordance with embodiments of the present invention.

The numerical data obtained from quantitative gene expression and numerical data from calibrated gene expression relative to a baseline profile data set may be stored in databases or digital storage mediums and may retrieved for purposes including managing patient health care or for conducting clinical trials or for characterizing a drug. The data may be transferred in networks via the World Wide Web, email, or internet access site for example or by hard copy so as to be collected and pooled from distant geographic sites (FIG. 8).

In an embodiment of the present invention, a descriptive record is stored in a single database or multiple databases where the stored data includes the raw gene expression data (first profile data set) prior to transformation by use of a baseline profile data set, as well as a record of the baseline profile data set used to generate the calibrated profile data set including for example, annotations regarding whether the baseline profile data set is derived from a particular signature panel and any other annotation that facilitates interpretation and use of the data.

Because the data is in a universal format, data handling may readily be done with a computer. The data is organized so as to provide an output optionally corresponding to a graphical representation of a calibrated data set.

For example, a distinct sample derived from a subject being at least one of RNA or protein may be denoted as $P_j$. The first profile data set consists of $M_j$ where Mj is a quantitative measure of a distinct RNA or protein constituent. The record Ri is a ratio of M and P and may be annotated with additional data on the subject relating to for example, age, diet, ethnicity, gender, geographic location, medical disorder, mental disorder, medication, physical activity, body mass and environmental exposure. Moreover, data handling may further include accessing data from a second condition database which may contain additional medical data not presently held with the calibrated profile data sets. In this context, data access may be via a computer network.

The above described data storage on a computer may provide the information in a form that can be accessed by a user. Accordingly, the user may load the information onto a second access site including downloading the information. However, access may be restricted to users having a password or other security device so as to protect the medical records contained within. A feature of this embodiment of the invention is the ability of a user to add new or annotated records to the data set so the records become part of the biological information.

The graphical representation of calibrated profile data sets pertaining to a product such as a drug provides an opportunity for standardizing a product by means of the calibrated profile, more particularly a signature profile. The profile may be used as a feature with which to demonstrate relative efficacy, differences in mechanisms of actions. etc. compared to other drugs approved for similar or different uses.

The various embodiments of the invention may be also implemented as a computer program product for use with a computer system. The product may include program code for deriving a first profile data set and for producing calibrated profiles. Such implementation may include a series of computer instructions fixed either on a tangible medium, such as a computer readable medium (for example, a diskette, CD-ROM, ROM, or fixed disk), or transmittable to a computer system via a modem or other interface device, such as a communications adapter coupled to a network. The network coupling may be for example, over optical or wired communications lines or via wireless techniques (for example, microwave, infrared or other transmission techniques) or some combination of these. The series of computer instructions preferably embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (for example, shrink wrapped software), preloaded with a computer system (for example, on system ROM or fixed disk), or distributed from a server or electronic bulletin board over a network (for example, the Internet or World Wide Web). In addition, a computer system is further provided including derivative modules for deriving a first data set and a calibration profile data set.

Clinical Trials

Figures 10A, 10B:
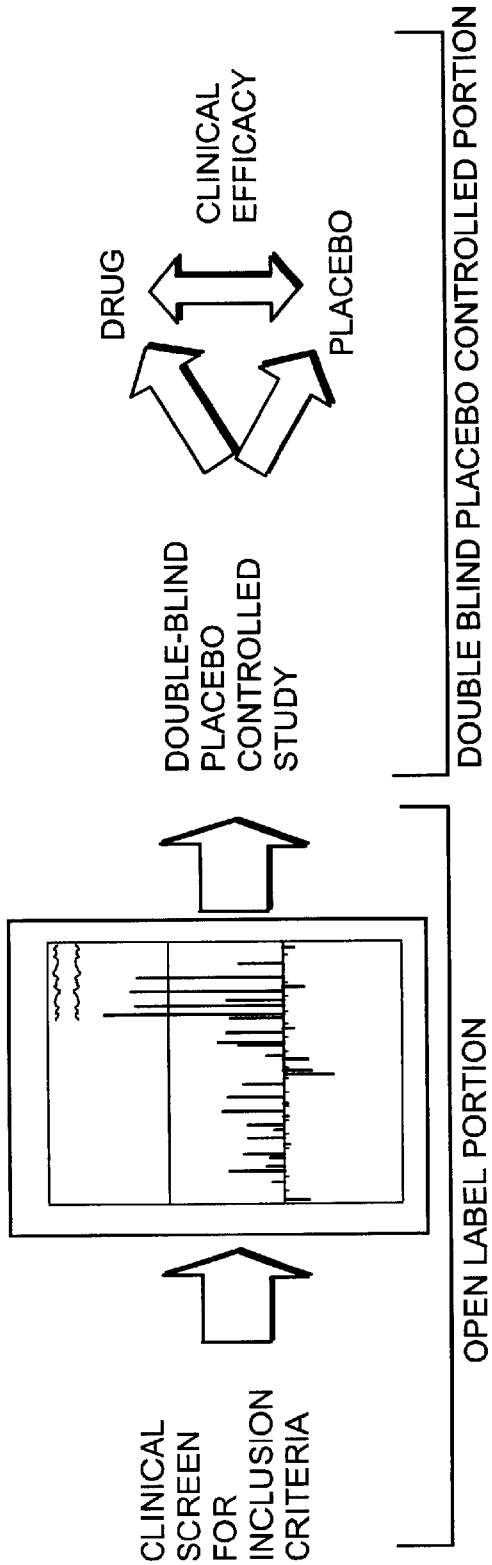
FIG. 10 shows a schematic of a phase two clinical trial that utilizes gene expression profiling (a). The right hand panel (b) indicates that the same information may be used in Phase IV or post marketing studies to compare the efficacy of already approved and marketed drugs or to guide the marketing of such therapies; to guide the choice of therapy for an individual subject or population from within a class of appropriate compounds.

The use of calibrated profile data sets for performing clinical trials is illustrated in FIG. 10 using the above-described methods and procedures for running a clinical trial or managing patient care. Moreover, standardization between laboratories may be achieved by using a particular indicator cell line such as THP-1 which is stimulated by a known stimulator such as lipopolysaccharide so that resultant profile acts as a measure that the laboratory is performing the protocol correctly. Of course this is one single example, and other cells lines, tissues, or biological samples or combinations of the foregoing may be used as standards.

A further embodiment of the invention provides a method for patient selection for augmenting clinical trials. Clinical trials in which candidate subjects are included or excluded according to a predetermined optimum calibrated profile for a given biological condition can result in more precise monitoring than would be otherwise possible. It can also result in a greater efficiency in clinical trial design because unsuitable patients that have for example complicating factors or conditions can be screened out. The calibrated profile data will also enhance the "signal to noise" by removing non-responders from clinical studies. The basic structure of a clinical trial design using gene expression profiling may follow any of several formats. These include testing body fluid from a candidate patient in the trial ex vivo against a new therapeutic agent and analyzing the calibrated profiles with respect to an agent-treated and placebo-treated samples using a predetermined selected panel and evaluating whether the candidate patient would be likely to respond without adverse effects to the composition being tested. In selected indications, profile data obtained from in vitro cell cultures or organ cultures may be desired where the cell originates from a target subject or from another subject or from an established cell line, or from a cell samples removed from the target subject where the cell samples may be obtained from any body fluid including a blood, urine, semen, amniotic, or a cerebrospinal fluid sample, or from a scraping from mucosal membranes such as from the buccal cavity, the eye, nose, vagina or by means of a biopsy including epithelial, liver, sternum marrow, testicular, or from tumor tissue removed surgically from a tumor at any location. The above-described sources of samples are applicable to any medical use in which calibrated profile data sets are desired.

Figure 12A:
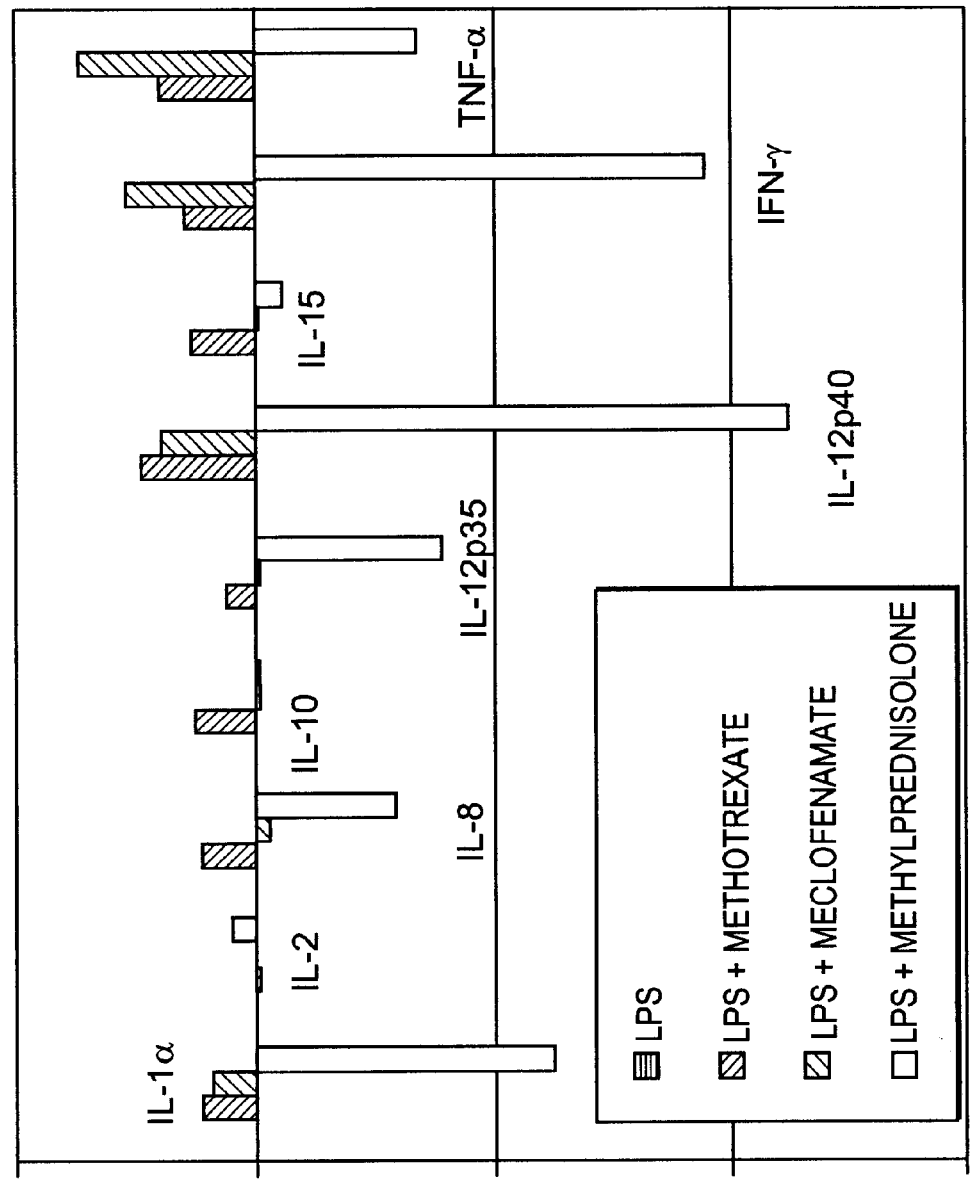
FIG. 12 is a bar graph with a logarithmic axis that shows a graphical representation of calibrated profile data sets for whole blood stimulated ex vivo with lipopolysaccharide (LPS), using a panel of 9 constituents, each constituent corresponding to a gene locus encoding the gene products indicated, the blood being further exposed to anti-inflammatory agents: methotrexate, meclofenamate and methylprednisolone. The baseline profile data set is derived from LPS stimulated (but otherwise untreated) cells.
Figure 21:
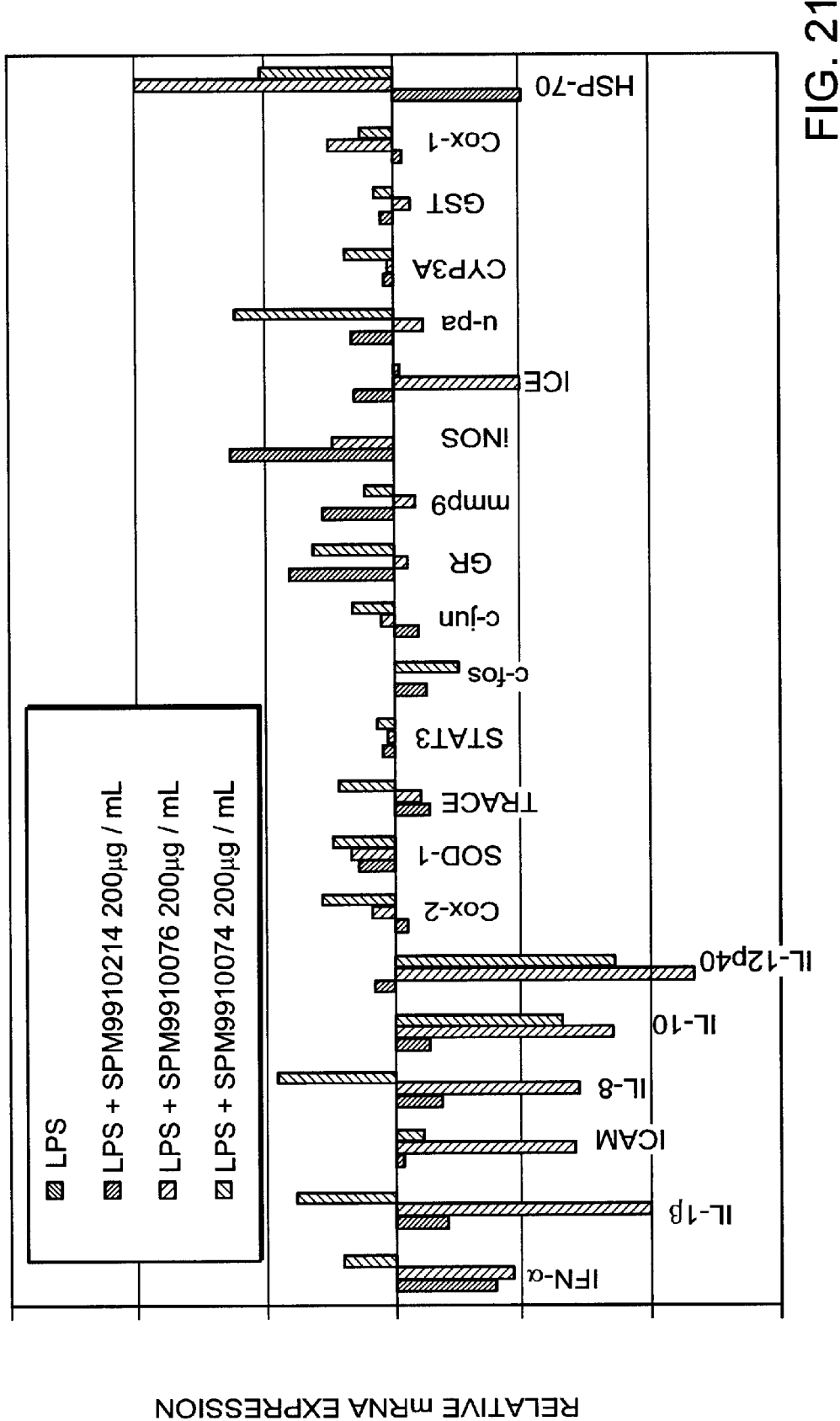
FIG. 21 is a bar graph with a logarithmic axis that shows a graphical representation of calibrated profile data sets for samples of blood treated ex vivo with LPS or LPS and one of three anti-inflammatory herbals (Echinacea, Arnica or Siberian Ginseng) at a concentration of 200 ug/ml. A panel of 24 constituents is used. The baseline profile data set is derived from LPS stimulated cells absent a herbal treatment. The figure illustrates the effectiveness of the use of the calibrated selected profile to investigate the overall effects of complex compounds such as nutraceuticals whose biological effect is a summation of more than one activity. In this case, each of the herbals is consumed as an immunostimulant, however the calibrated selected profiles reveal a unique pattern shows a mixture of both immunostimulatory and anti-inflammatory effects.

In vitro dosage and toxicity studies using calibrated profile data sets obtained from indicator cell lines or samples of the patient tested ex vivo may provide useful information prior to initiation of the clinical trial and may significantly reduce the cost and time of a clinical trial while increasing the likelihood of identifying the presence of beneficial effect(s). In particular, the dose may be optimized on an individualized basis to maximize the impact on therapeutic outcome. For example, FIG. 12 shows how ex vivo blood cells respond to the stimulatory effect of LPS and the subsequent treatment with an anti-inflammatory drug (methotrexate, meclofenamate or methylprednisolone). The data show how the effect of methotrexate and meclofenamate generates similar calibrated profile data sets where the baseline is LPS treated blood. In contrast, methylprednisolone has a substantially different effect from the other two compounds. A similar type of analysis can be performed with complex mixtures, as illustrated in FIG. 21, in which the calibrated profiles obtained when Echinacea, Arnica and Siberian Ginseng applied to LPS stimulated blood ex vivo are compared. In this example, all three agents appear to act differently from each other with respect to a sample from a single subject. Similar analyses can be used to compare compounds with unknown targets or activities or metabolic patterns to compounds, complex or simple, with known or pre-determined profiles.

The above methods and procedures may be utilized in the design and running of clinical trials or as a supplemental tool. Moreover, the above methods and procedures may be used to monitor the patients' health as well as the patient's responsiveness to an agent before during and after the clinical trial. This includes monitoring whether multiple agents interfere with each other, act synergistically or additively or are toxic or neural with respect to each other. This type of information is very important as individuals take an increasing number of medications.

Similarly, the methods and procedures described above may be used to manage patient care for an individual or a population. Such methods and procedures may also be used to develop a regional or global research network that uses calibrated profile data sets and the resulting databases to conduct research or trials.

Both the calibration profile data sets in graphical form and the associated databases together with information extracted from both are commodities that can be sold together or separately for a variety of purposes. For example, graphic representations of calibration profile data sets may provide a description of a product with respect to its activity that may be used to promote the product. Alternatively, the graphical form of the calibrated profile data sets and access to baseline profile databases provide a means for manufacturers to test discrete batches of product against a gold standard.

The data may be used strategically for design of clinical trials. It may also be useful for physicians practicing at remote sites to offer personalized healthcare to a patient. Accordingly, the physician may set up personalized databases for calibrated profile data sets prior to and after treatment of a particular condition. New data on the subject could be added to the personalized database at each visit to the doctor. The data may be generated at remote sites by the use of kits that permit a physician to obtain a first profile data set on a sample from a patient. For remote users to access the site, it is envisaged that secured access to the global network containing libraries of baseline profile data sets and calibrated profile data sets, classified by particular criteria and representing data from larger populations than a single individual, would be necessary. The access to the global database may be password protected thereby protecting the database from corrupted records and safeguarding personal medical data. The graphical form provided by the calibrated data sets may be used to create catalogs of compounds in a pharmacopiae complete with toxic effects that might arise for particular individuals as well as other types of drug interactions.

Access to the global database may include the option to load selected data onto a second access site. This process may include downloading the information to whatever site is desired by the user and could include securing hard copies of information. It is desirable to control how and what data is offloaded or copied to maintain the integrity of the database. It is envisaged that while a global network of clinical data would be an informational resource, it would have utility in conducting research that may include epidemiological studies and studies concerning the mechanism of action of an agent, as well as studies concerning the nature of interpersonal variability as determined by calibrated profile data sets.

Examples of Medical Uses (a) Early detection of infectious diseases: Markers or surrogate markers from mice may be obtained for measuring gene expression in humans that indicate early or immediate response to infection, for example, to a virus such as hepatitis virus, or to a bacterium such as *Mycobacterium tuberculosis* (the etiologic agent of tuberculosis) (see FIG. 4). Candidate genes are identified and changes in expression of those genes in the presence of a challenge provide a set of markers. The set of markers can combine markers encoded by the genome of the subject and one more distinctive markers encoded by the genome of the infectious agent. For example, changes in expression of an immediate early gene of a virus, e.g. a gene encoding an enzyme of viral replication, and a host gene such as the gene for any or all of IL-2, IL-4 and IL-5, may comprise markers or surrogate markers for a medical condition capable of detecting that condition prior to the onset of medical symptoms. This method may afford earlier detection of an infection than is possible using current diagnostic techniques.

(b) Toxicity profiles and mechanistic profiles obtained from an in vitro assay and in vivo assays. Toxicity and mechanistic information arising from the administration of a compound to a population of cells may be monitored using calibrated profile data sets. The following is an example of an experimental protocol for obtaining this information. Firstly, an experimental group is established: (1) control cells maintained without therapeutic agent and without stimulus; (2) cells treated with therapeutic agent but without stimulus; (3) cells without therapeutic agent but with stimulus, (4) sample with therapeutic agent and with stimulus. The population of cells can be selected from primary cell cultures prepared in culture plates using methods well established in the art; or mature differentiated cell preparation from whole blood or isolated monocytes from the target organism.

The cells are stimulated so as to present a targeted physiological condition by pretreatment with LPS purified from a Gram-negative bacterium (a variety of LPS preparations from pathogenic bacteria, for example, from *Salmonella typhimurium* and from *Escherichia coli* O1157:H7, are available from Sigma, St. Louis, Mo.). The therapeutic agent administered to the cell samples in this example is an inhibitor of an enzyme known to be key in disease etiology, namely an inhibitor of a protease or a nucleic acid polymerase. Following treatment by addition of the therapeutic agent and further incubation for four to six hours, samples of the cells are harvested and analyzed for gene expression. Nucleic acid, specifically mRNA, can be prepared from the sample by methods known to one or ordinary skill in the art (see, for example, the Lyse-N-Go™ reagent, Pierce Chem. Co., Rockford, Ill.). Samples are analyzed by QPCR according to a quantitative replicative procedure, (for example, quantitative polymerase chain reaction procedure (QPCR)) (see, for example, Gibson, U. 1996 Genome Res. 6:995–1001, and references cited therein). Total RNA was assessed using universal primers. Toxicity of the agent for cells can be measured in untreated cells by vital stain uptake, rate of DNA synthesis (autoradiography of labeled nucleic compared to cells stained), stain by DNA-specific eyes (Hoechst), etc. Mechanistic profiles can be determined by analysis of the identifies of de novo up- or down-regulated genes. Further, in the presence of a therapeutic agent, some genes are not expressed or differentially expressed, indicating potential efficacy of the therapeutic agent in suppressing the effects of stimulation by the LPS. For example, in FIG. 21, levels of ICE that are somewhat stimulated in the presence of LPS+Echinacea are substantially depressed by LPS+Arnica relative to LPS stimulated cells absent agent. Levels of HSP 70 which are depressed in the presence of LPS+Echinacea are substantially stimulated in the presence of LPS+Arnica, and LPS+Siberian Ginseng relative to LPS stimulated cells absent the addition of an agent. Levels of IL-12p40 which are slightly increased in the presence of LPS+Echinacea are substantially depressed in the presence of LPS+Arnica and LPS+Siberian Ginseng relative to LPS stimulation. Similarly, FIG. 16 shows a much enhanced reduction of gene expression in whole blood for IL-1α, Il-1β, Il-7, Il-10, IL-IL-15, IFN-γ, TGF-β, TNF-β cox-2, and ICAM in the presence of prednisolone+LPS when compared to arnica +LPS or nothing+LPS.

(c) Quantitation of gene expression in a blood cell to predict toxicity in another tissue or organ.

Leukocytes, for example, may be obtained from a blood sample of a subject, for the purpose of assessing the appearance of a pathological condition in another organ, for example, the liver. A profile data set is obtained of genes expressed in the leukocytes, for example, genes encoding a set of lymphokines and cytokines. The data set is compared to that of the database, to examine correlations, for example to other subjects, and to the subject prior to administration of a therapeutic agent.

By this method, a correlation can be drawn between, for example, administration of acetaminophen (Tylenol) and sensitivity to this therapeutic agent and manifested by liver damage. An early prediction of therapeutic agent sensitivity, detected prior to the onset of actual damage to the liver, may be clinically available so that the subject receives no further administration of acetaminophen. The database may be used to detect a correlation or correlations prior to the onset of traditional medical assessments, such as increase in bilirubin level or other indication of liver pathology.

(d) Calibrated profiles from blood cells for prognosis of severity and prediction of adverse reactions in treatment of an autoimmune disease.

The probability and timing of onset of symptoms of an autoimmune disease, for example, rheumatoid arthritis, may be monitored by appearance of expression of markers or surrogate markers as determined by the methods of gene expression profiling of markers or surrogate markers and comparison to a profile database as described above. Thus an indication of onset may be obtained, and advance management by utilization of preventive measures to forestall onset, can be taken. Further, the user may choose a set of potential therapeutic agents, and assess for a given agent, the probability that a subject will present an adverse reaction if given a full course of treatment, prior to that full course. For example, using embodiments of the invention, a single dose or a few doses of the agent methotrexate may be administered to a subject having arthritis and in need of a therapeutic agent. If the gene expression profile data set of the subject in response to the short course of methotrexate correlates with data sets from subjects having adverse reactions to this agent, then administration of a full course of methotrexate is counterindicated. Conversely, if the gene expression profile data set correlates with those of subjects who have responded positively to administration of a course of methotrexate treatment, then this therapeutic agent can be administered to the subject with much lower probability of adverse reaction.

Discussion of Figures

FIGS. 1–4 illustrate some of the applications of calibrated profile data sets. In FIG. 1, three possible scenarios are provided. Firstly, a candidate therapeutic agent may be tested to determine its molecular pharmacology and toxicology profiles. The test might include obtaining calibrated profile data sets for a series of selected panels selected on the basis of what activity is predicted for the drug. The population of cells exposed to the agent may be the result of in vivo administration as depicted by the mouse or direct exposure in vitro where the cells may be an indicator cell line or an ex vivo sample from the subject. The result of the screen is the identification of more effective drug, candidates for testing in human subjects.

The second scenario in FIG. 1 is the use of calibrated profile data sets to identify a suitable clinical population for screening a potential therapeutic agent. Both demonstration of lack of toxicity and demonstration of clinical efficacy require certain assumptions about the clinical population. The calibrated profile data sets provide a means for establishing those assumptions with respect to the biological condition of the individuals selected for the clinical trials.

The third scenario in FIG. 1 involves the practice of individualized medicine, which may include creating an archive of calibrate profile data sets on the individual in a state of health such that changes can be identified using signature panels so as to permit evaluation, prognosis, or diagnosis of a particular condition. Moreover, stored information about the patient in the form of calibrated profile data sets permits selecting one of a group of possible therapeutic agents most likely to be effective for the patient, optimizing dosage of drug, and detecting adverse effects that might arise through drug-drug interactions before symptoms arise. Use of calibrated profile data sets may provide more efficient and cost-effective health care management.

Figure 2:
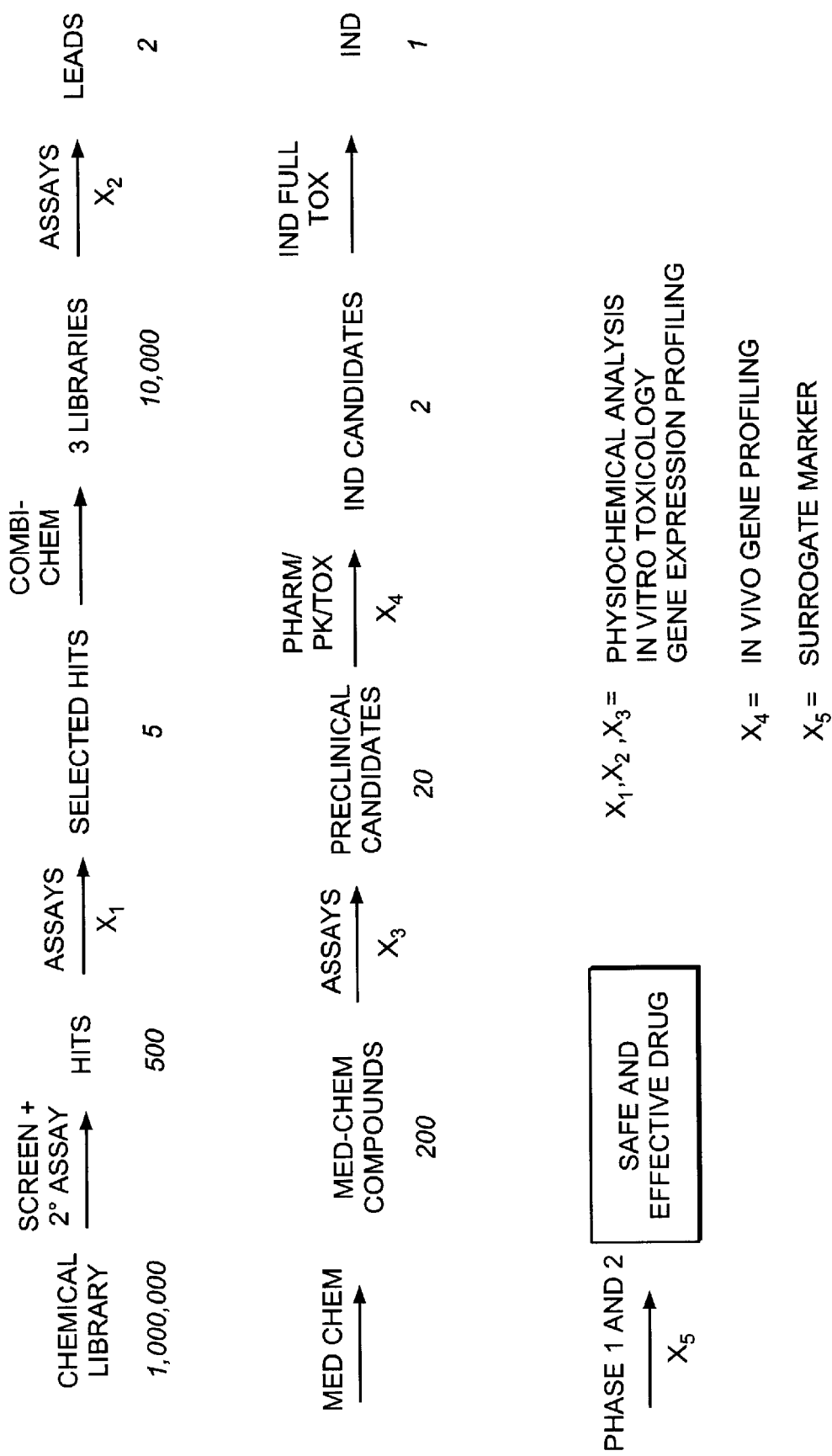
FIG. 2 is a diagram showing the drug discovery pathway of new compounds from early leads to likely drug candidates. Although calibrated profile data sets are indicated at the pre-clinical step, gene expression data can be acquired and is useful at any of the stages shown. IND refers to investigative new drug and refers to an early stage in regulatory review.
Figure 3:
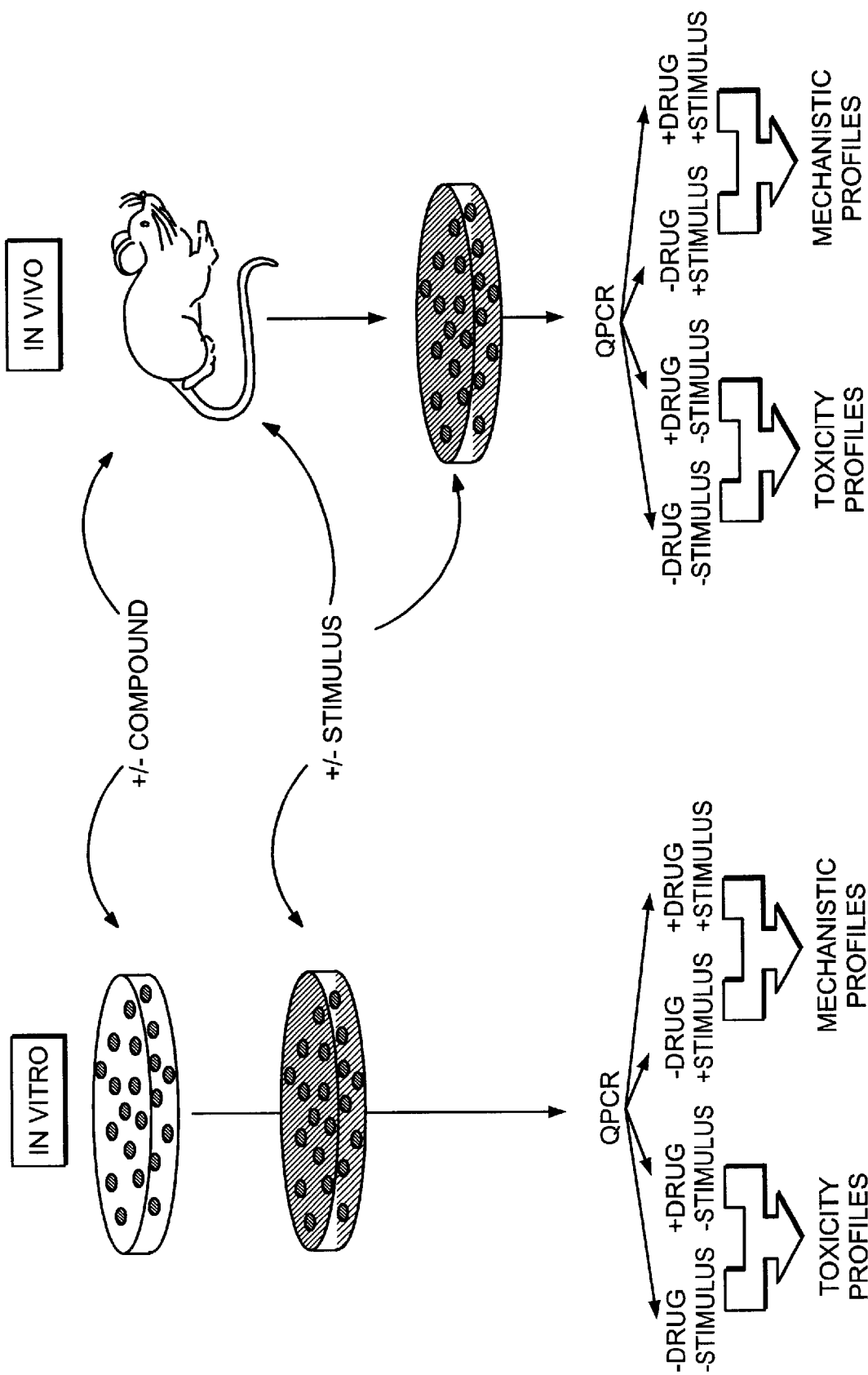
FIG. 3 is a diagram presenting a comparison of in vivo and in vitro protocols for forming calibrated profile data sets for rapidly assessing product candidate toxicity and efficacy in accordance with several embodiments of the present invention.
Figure 4:
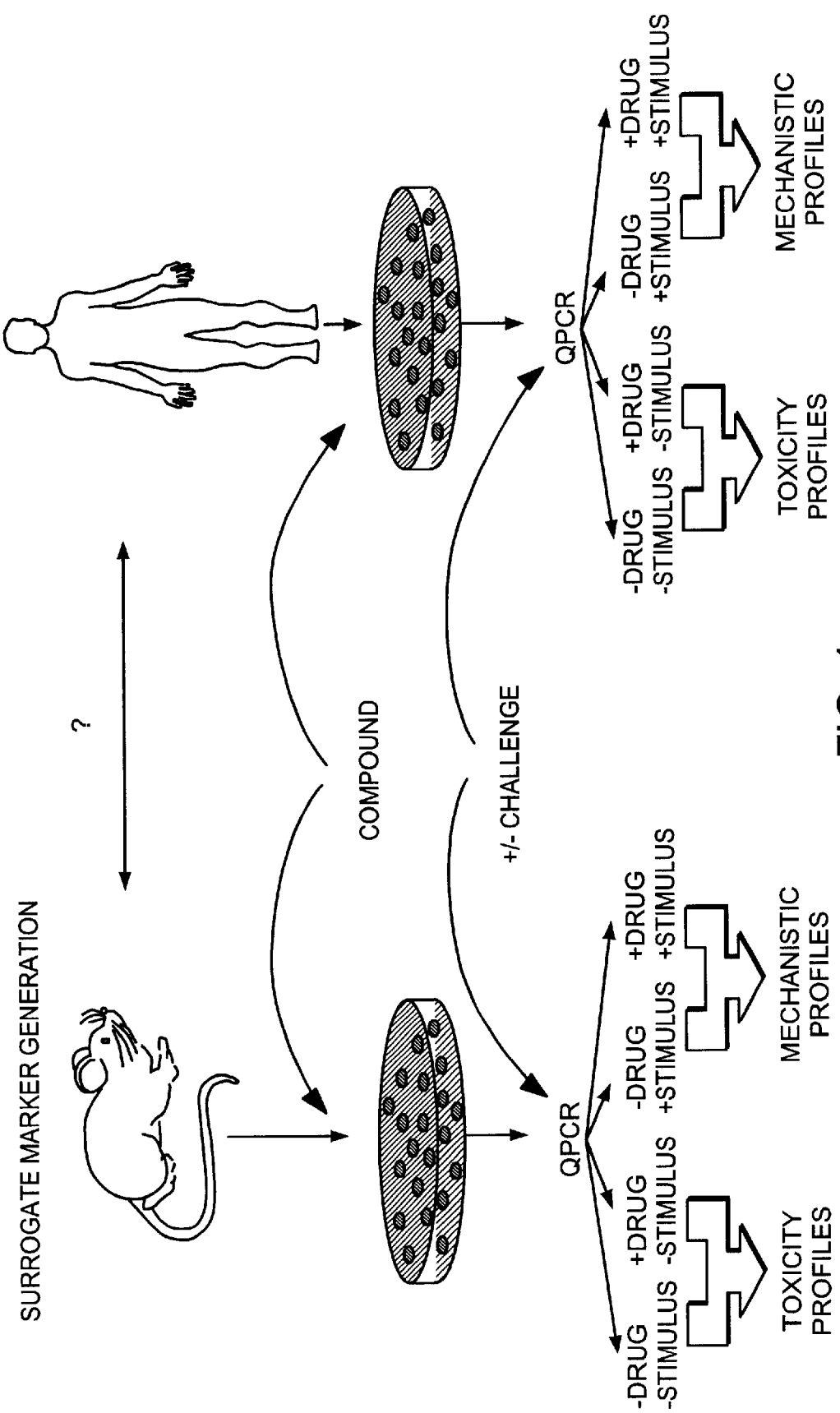
FIG. 4 is a diagram showing the application of gene expression profiling as a guide to pre-clinical and clinical studies in accordance with an embodiment of the present invention.

The novel approach described above for evaluating a biological condition of a subject may be applied to an ex vivo or in vitro assay for measuring the effect of an agent on a biological condition as illustrated in FIGS. 2–4. A sample from the patient may measured directly ex vivo or tested ex vivo against an agent to predict an effect in the patient. This provides a quick and effective way to determine which drug, chosen from within a single class of drugs that all may be used to treat a particular condition, may be most effective for a given subject. Alternatively, an agent may be tested on an indicator cell line that can provide a quantitative measure of therapeutic performance in a class of individuals.

FIG. 2 illustrates how calibrated profile data sets may assist in screening a library of candidate compounds to discover candidate drugs. Starting with for example, 500 candidate drugs, these can be tested in indicator cells or ex vivo body fluid or tissues against signature panels for iii vitro toxicology or metabolic indicators. The figure illustrates the large number of compounds that entered in late stages in the development process only to ultimately be rejected due to adverse biological interactions. Use of calibrated profile data sets may in many instances more readily identify likely successful candidates and thereby reduce the expense and untoward effects of animal and human experimentation for compounds that could have been predicted to fail.

FIG. 3 illustrates how a compound may be administered to an experimental animal such as a mouse or to an indicator cell line. The in vivo or ex vivo or indicator cell sample may further be treated with a stimulus. The result of both the compound and the stimulus may then be detected, for example, using signature profiles for toxicity or for mechanism to compare the effect of no drug+/–stimulus or +/–and no stimulus. Both in vitro (left panel of FIG. 3) and in vivo (right panel of FIG. 3) studies can be used to evaluate the effect of a compound (drug, nutraceutical, environmental stimuli, etc.). The right hand panel also illustrates the specific embodiment of an "in vitro clinical trial", that is, treatment of cells obtained from a subject and treated with a compound (with or without a stimulus) in vitro (or ex vivo) in order to predict the outcome of similar treatment of the subject in vivo (see FIG. 15 for a specific example). The output from both panels is described as toxicity and mechanistic profiles. Either experimental course may be used to both evaluate potential toxicity, e.g., using the toxicity, or liver metabolism selected panels, and to determine or confirm likely mechanism of action by a critical selection of a gene panel(s) that illustrates and differentiates molecular mechanisms of action (see FIG. 12 for a specific example). These are merely examples, and other selected panels may be employed to evaluate or characterize other biological effects or conditions. FIG. 4 illustrates a bioassay in which cells are removed from the subject and tested ex vivo with the addition of a compound and also a challenge or stimulus. The ex vivo effect of stimulus and then drug on whole blood taken from a human subject is shown in FIG. 12 in which the stimulus is lipopolysaccharide (an inflammatory agent) while the drug is any of methotrexate, meclofenamate or methylprednisolone using a signature panel for inflammation. Methylprednisolone, a drug commonly used in the treatment of acute exacerbations of COPD as well as in the chronic management of this disease, is considered to be a potent by non-specific anti-inflammatory agent. However, as demonstrated in FIG. 22, its effects on gene expression are dependent on the stimulus. While there are general qualitative similarities between the effects on gene expression across these three stimuli, there are both quantitative and qualitative differences that may be important in understanding when glucocorticoid intervention is warranted.

According to embodiments of the invention, an indicator cell population is used to measure quantitative gene expression the effect of an agent or a biological sample may influence the choice of which indicator cell line will be most informative. For example, a cloned cell line such as THP-1 or a primary cell population (peripheral mononuclear cells) may provide information that is comparable to that obtained from a body sample directly (see FIG. 15). The normal state of gene expression may range from zero or few transcripts to $10_5$ or more transcripts.

Similarly, an agent may be evaluated for its effect on any population of cells, either in vivo, ex vivo or in vitro, by administering the agent and then determining a calibrate profile data set for those cells under the selected conditions. Examples of this approach are provided in FIGS. 10–16 and 18. FIG. 18 further provides calibrated profile data sets for different concentrations of a single agent showing that the transcription of selected constituents vary with dose and therefore the anticipated effectiveness with respect to the biological condition.

Figure 16B:
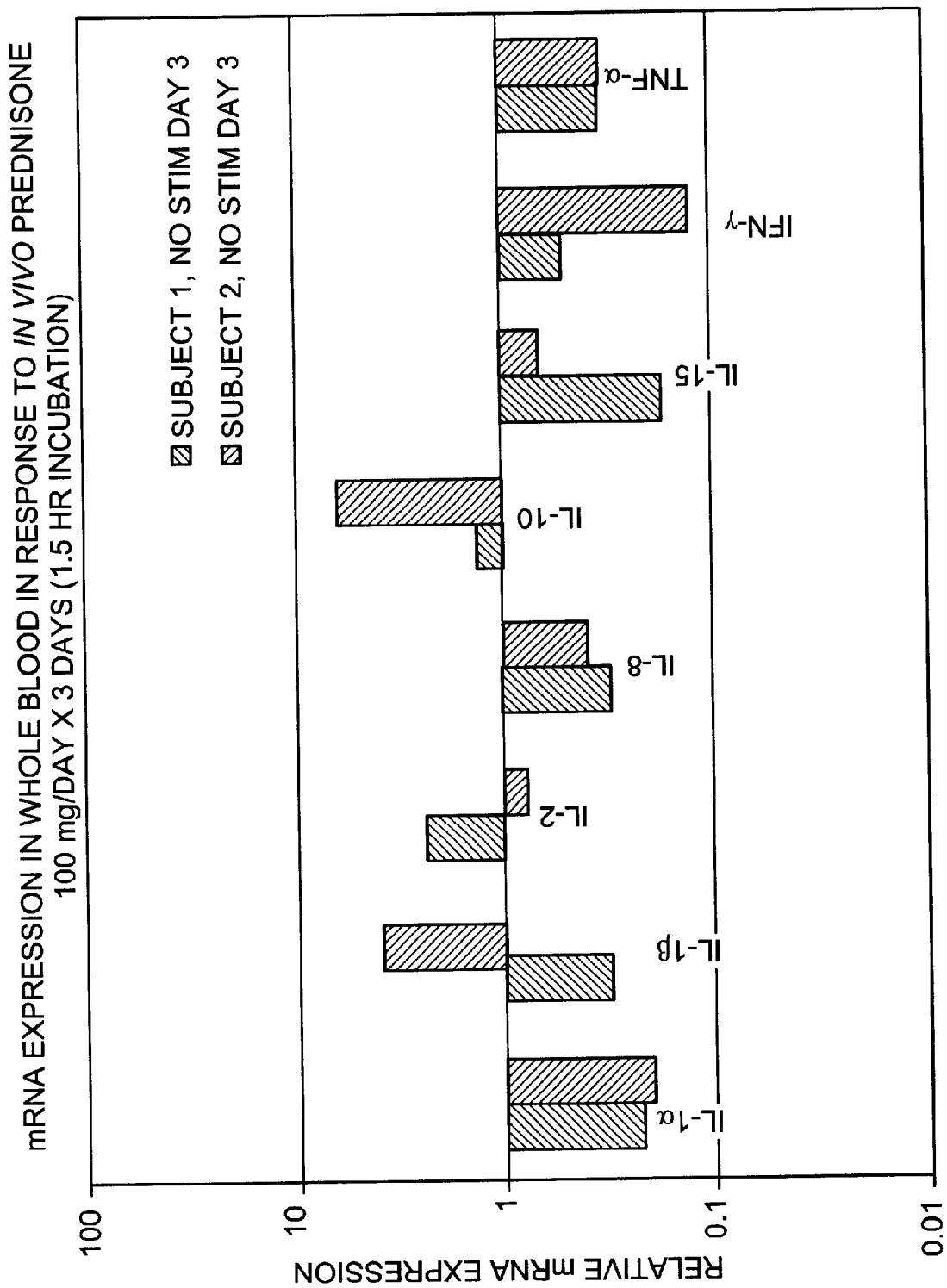
Figure 17:
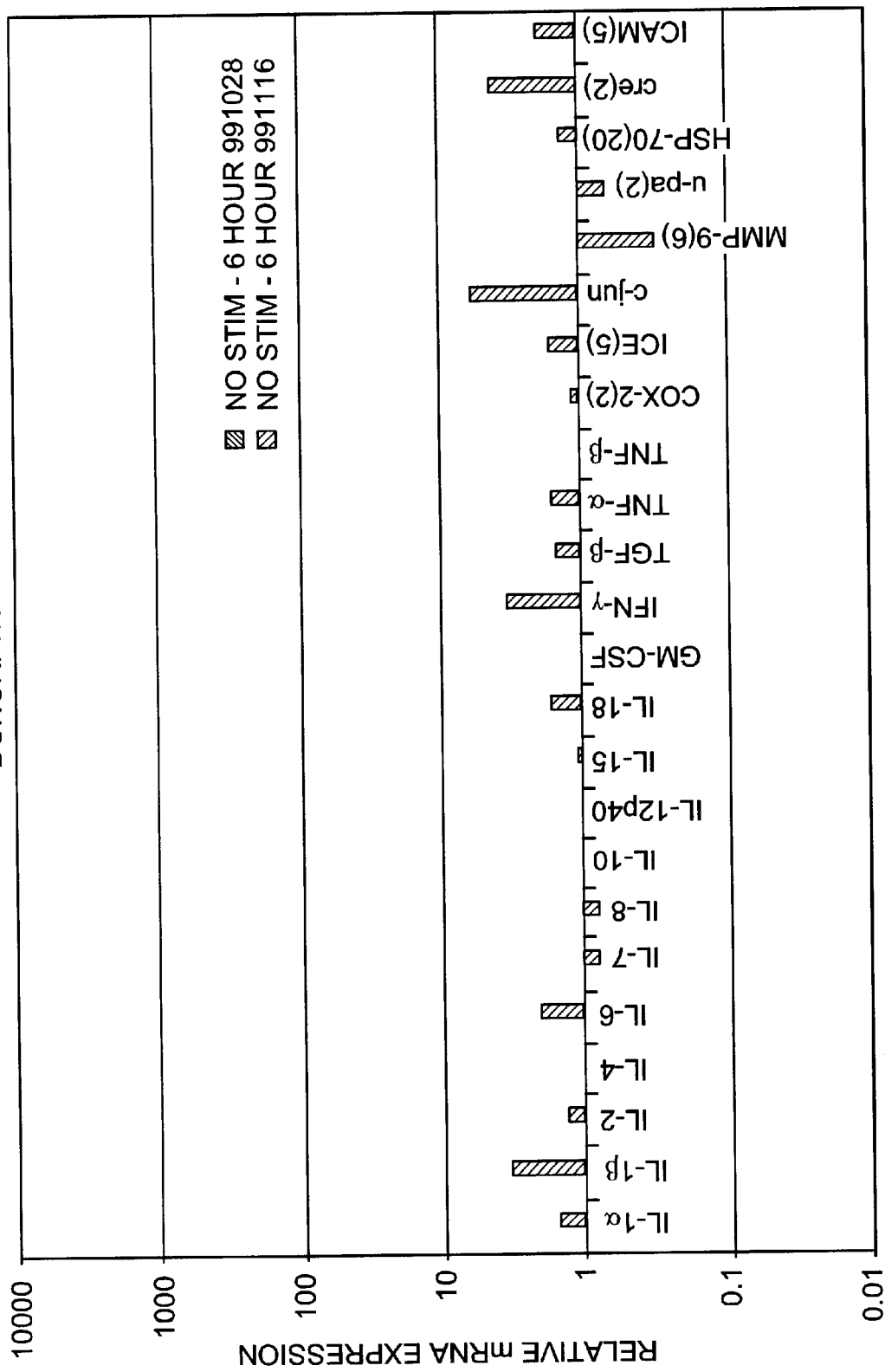
FIG. 17 is a bar graph with logarithmic y axis that shows a graphical representation of calibrated selected profile data sets for two samples taken from a single subject within a 19 day period using a panel (e.g., inflammation panel) of 24 members where each member corresponds to a unique gene locus. The baseline profile data set relates to peripheral blood taken from the subject prior to treatment.

The above description of determining a biological condition is exemplified as follows: the action of a pharmaceutical or nutraceutical is measured with respect to its anti-inflammatory properties. The measurement of the effect may be established using a selected panel of constituent gene loci for example, an inflammation selected panel, including, Interleukin 1 alpha (IL-1α) or Tumor Necrosis Factor alpha (TNF-α). The anti-inflammatory effect may first be established by treating indicator cells or sample cells ex vivo with a known inflammation inducers (for example, lipopolysaccharide or other mitogens) followed by treatment with the experimental agent or condition expected to affect the expression from the appropriate gene loci. Accordingly, a baseline profile data set may be established in this case as the gene expression for a particular panel of constituents resulting in the presence of the inflammation inducer. The addition of a potential anti-inflammatory agent results in a change relative to the baseline. This approach is illustrated for example in FIG. 12. Methylprednisolone has a substantial down regulation effect on IL-2 in blood cells stimulated ex vivo with LPS where the baseline data set is LPS stimulated cells. In this case the effect is shown as negative. In contrast, as shown in FIG. 16b, IL-2 appears to be upregulated in whole blood not previously exposed to LPS, where the baseline data set is unstimulated cells. These results are consistent with the observation that methylprednisolone stimulates IL-2 production.

The determination of the biological condition of a subject may include measuring and storing additional data about the subject. For example, if the subject is a human or mammalian patient, additional clinical indicators may be determined from blood chemistry, urinalysis, X-ray, other chemical assays and physical or sociological findings.

Figure 7:
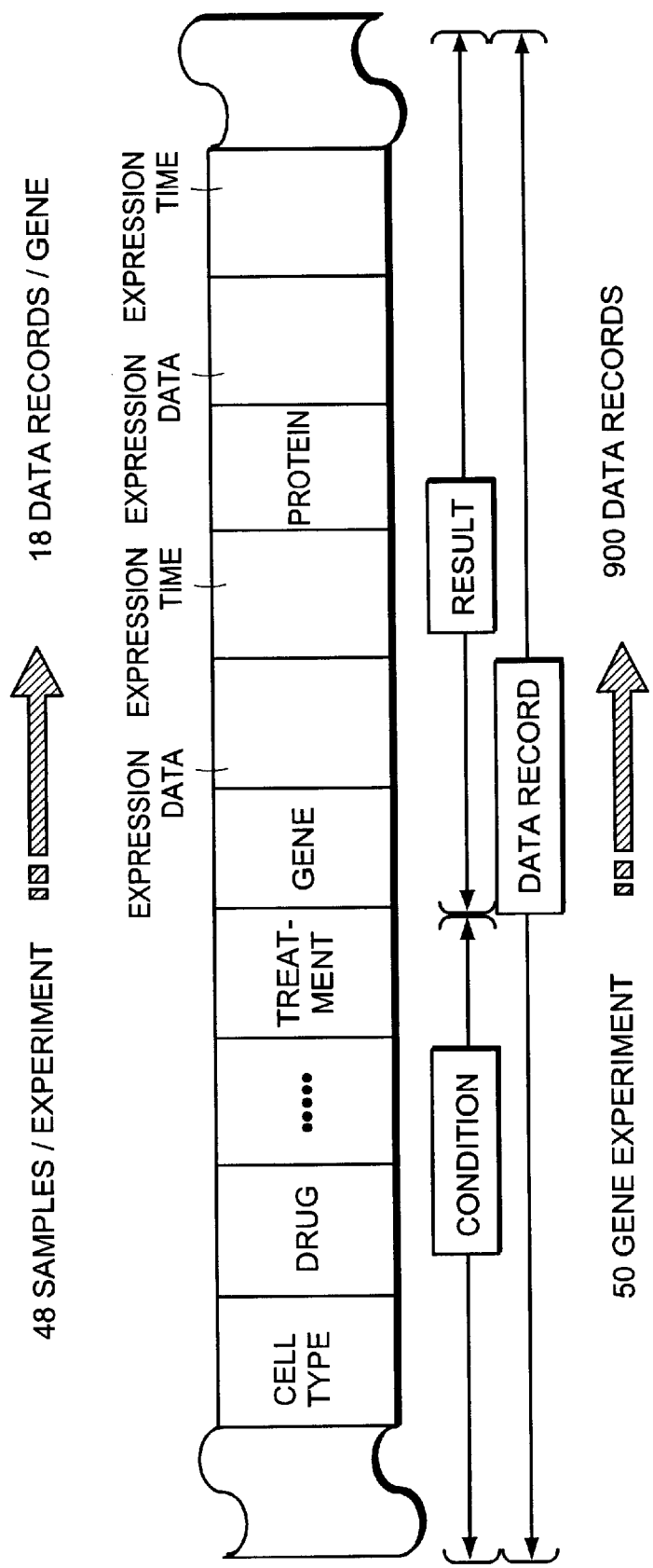
FIG. 7 is a diagram illustrating the structure of a profile data record in accordance with an embodiment of the present invention.

FIG. 7 illustrates how the accumulation of calibrated profile data sets may improve the predictive power of the database and thereby increase its value in generating information about a biological condition or agent. The figure indicates the use of the database in terms of its power, for example, to predict the course of a therapeutic intervention or follow the course of an individual subject compared to a population. Information from the database may be used to predict a likely mechanism of metabolism or molecular mechanism of action, and to compare a single profile to a collection of signature, calibrated selected profiles.

Use of a database in accordance with an embodiment of the present invention is illustrated in FIG. 8. FIG. 8 illustrates a data profile set from the database. Entries for input include a name, an Experimental Type, and whether the entry is a New Reference; Cell/Tissue/Species and whether these are new; Therapeutic agent (compound), Dose, and additional parameters and whether the therapeutic agent is new. Observations are recorded according to the identity of a Gene (New Gene) and a Protein (New Protein). The Stimulus or other Treatment, if any, and the Dose are entered. Gene (and/or Protein) Expression, Expression Value, Expression Units if appropriate and Expression Time are shown. The figure specifically illustrates the range of applicable fields of investigation from complex natural products to clinical trails in humans, linkage to traditional forms of measurement and evaluation such as literature citations, clinical indicators and traditional pharmacokinetic measurements. Expert analysis of the selected profile data contained in the database may then be used to guide product development and marketing, or used to improve the clinical decision making concerning the health of a single individual or population of individuals.

One form of record may provide information about a subject or agent with respect to identity, medical history including traditional pharmaceutical/medical data, clinical indications as determined from literature data, reference to additional types of analysis in the database, etc.

Figure 9:
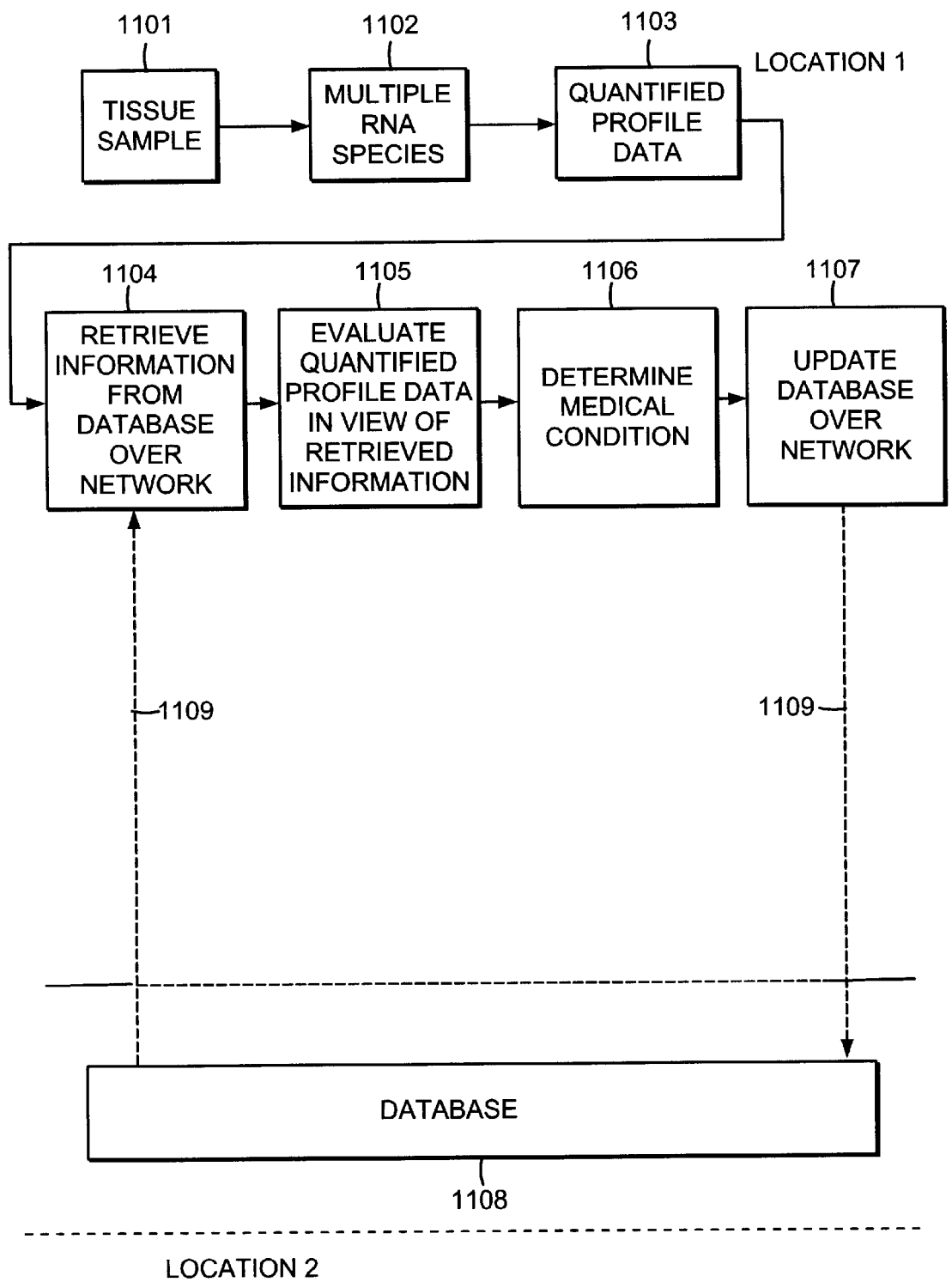
FIG. 9 shows an embodiment of the present invention in which profile data, in either the raw or calibrated form, is evaluated using data from a database that is remotely accessed over a network.

FIG. 9 shows an embodiment of the present invention in which profile data is evaluated using data from a database that is remotely accessed over a network. Using the approach of this figure data may be derived at one or more locations (such as location 1 shown here), compared using information retrieved over communication path 1109 from a central database at location 2, and the result of the comparison may be used to affect, for example, the course of treatment of an individual or population. The communication path 1109 between location 1 and location 2 is two-way, so that information resulting from determinations made at location 1 may delivered over the path 1109 to update the database 1108. The consequence is an iterative process whereby the information from database is used in a determination that may affect the course of treatment, evaluation, or development, and the results of the determination become part of the database. In a first location, as in FIG. 5, from a tissue sample procured in process 1101, there are derived multiple RNA species pursuant to process 1102, and then in process 1103, profile data are quantified to produce a profile data set that is pertinent to the tissue sample obtained in process 1101. In order to evaluate the profile data set, in process 1104 information is retrieved from database 1108, which is located in a second location. In fact the database may be in communication with a large number of locations, each of which is generating profile data that must be evaluated. The retrieval of information from the database is accomplished over a communication path 1109, which may include a network such as the Internet, in a manner known in the art. Once information has been obtained from the database 1108, the information is used in evaluating the quantified profile data in process 1105, with the result in process 1106 that the medical condition of the subject may be assessed. In process 1107, the database 1108 is updated over the communication path 1109 to reflect the profile data that have been quantified in process 1103. In this manner the database 1108 may be updated to reflect the profile data obtained over all locations, and each location has the benefit of the data obtained from all of the locations. While, for simplicity, all of the processes in FIG. 9 are shown as taking place at location 1, some or even all of the processes may be implemented elsewhere, for example location 2, or in multiple locations. At location 2, associated with the database, for example, may be a server that is used for hosting these processes, including evaluation of the quantified profile data.

EXAMPLES

Example 1

(a) Use of whole blood for ex vivo assessment of a biological condition affected by an agent.

Human blood is obtained by venipuncture and prepared for assay by aliquoting samples for baseline, no stimulus, and stimulus with sufficient volume for at least three time points. Typical stimuli include lipopolysaccharide (LPS), phytohemagglutinin (PHA) and heat-killed staphylococci (HKS) or carrageean and may be used individually (typically) or in combination. The aliquots of heparinized, whole blood are mixed without stimulus and held at 37° C. in an atmosphere of 5% CO2 for 30 minutes. Stimulus is added at varying concentrations, mixed and held loosely capped at 37° C. for 30 min. Additional test compounds may be added at this point and held for varying times depending on the expected pharmacokinetics of the test compound. At defined times, cells are collected by centrifugation, the plasma removed and RNA extracted by various standard means.

Nucleic acids, RNA and or DNA are purified from cells, tissues or fluids of the test population or indicator cell lines. RNA is preferentially obtained from the nucleic acid mix using a variety of standard procedures (or RNA Isolation Strategies, pp. 55–104, in *RNA Methodologies, A laboratory guide for isolation and characterization*, 2nd edition, 1998, Robert E. Farrell, Jr., Ed., Academic Press); in the present use using a filter-based RNA isolation system from Ambion (RNAqueous™, Phenol-free Total RNA Isolation Kit, Catalog #1912, version 9908; Austin, Tex.).

In accordance with one procedure, the whole blood assay for selected profiles determination was carried out as follows: Human whole blood was drawn into 10 mL Vacutainer tubes with Sodium Heparin. Blood samples were mixed by gently inverting tubes 4–5 times. The blood was used within 10–15 minutes of draw. In the experiments, blood was diluted 2-fold, i.e. per sample per time point, 0.6 mL whole blood +0.6 mL stimulus. The assay medium was prepared and the stimulus added as appropriate.

A quantity (0.6 mL) of whole blood was then added into each 12×75 mm polypropylene tube. 0.6 mL of 2X LPS (from *E.coli* serotye 0127:B8, Sigma #L3880 or serotype 055, Sigma #L4005, 10 ng/ml, subject to change in different lots) into LPS tubes was added. Next, 0.6 mL assay medium was added to the "control" tubes with duplicate tubes for each condition. The caps were closed tightly. The tubes were inverted 2–3 times to mix samples. Caps were loosened to first stop and the tubes incubated @ 37° C., 5% CO2 for 6 hours. At 6 hours, samples were gently mixed to resuspend blood cells, and 1 mL was removed from each tube (using a micropipettor with barrier tip), and transfered to a 2 mL "dolphin" microfuge tube (Costar #3213).

The samples were then centrifuged for 5 min at 500×g, ambient temperature (IEC centrifuge or equivalent, in microfuge tube adapters in swinging bucket), and as much serum from each tube was removed as possible and discarded. Cell pellets were placed on ice; and RNA extracted as soon as possible using an Ambion RNAqueous kit (b) Amplification Strategies.

Specific RNAs are amplified using message specific primers or random primers. The specific primers are synthesized from data obtained from public databases (e.g., Unigene, National Center for Biotechnology Information, National Library of Medicine, Bethesda, Md.), including information from genomic and cDNA libraries obtained from humans and other animals. Primers are chosen to preferentially amplify from specific RNAs obtained from the test or indicator samples, see, for example, RT PCR, Chapter 15 in *RNA Methodologies, A laboratory guide for isolation and characterization*, 2nd edition, 1998, Robert E. Farrell, Jr., Ed., Academic Press; or Chapter 22 pp.143–151, *RNA isolation and characterization protocols*, Methods in molecular biology, Volume 86, 1998, R. Rapley and D. L. Manning Eds., Human Press, or in Statistical refinement of primer design parameters, Chapter 5, pp.55–72, PCR applications: protocols for functional genomics, M. A. Innis, D. H. Gelfand and J. J. Sninsky, Eds., 1999, Academic Press). Amplifications are carried out in either isothermic conditions or using a thermal cycler (for example, a ABI 9600 or 9700 or 7700 obtained from Applied Biosystems, Foster City, Calif.; see Nucleic acid detection methods, pp. 1–24, in *Molecular methods for virus detection*, D. L. Wiedbrauk and D. H., Farkas, Eds., 1995, Academic Press). Amplified nucleic acids are detected using fluorescent-tagged detection primers (see, for example, Taqman™ PCR Reagent Kit, Protocol, part-number 402823 revision A, 1996, Applied Biosystems, Foster City Calif.) that are identified and synthesized from publicly known databases as described for the amplification primers. In the present case, amplified DNA is detected and quantified using the ABI Prism 7700 Sequence Detection System obtained from Applied Biosystems (Foster City, Calif.). Amounts of specific RNAs contained in the test sample or obtained from the indicator cell lines can be related to the relative quantity of fluorescence observed (see for example, Advances in quantitative PCR technology: 5' nuclease assays, Y. S. Lie and C. J. Petropolus, Current Opinion in Biotechnology, 1998, 9:43–48, or Rapid thermal cycling and PCR kinetics, pp. 211–229, chapter 14 in PCR applications: protocols for functional genomics, M. A. Innis, D. H. Gelfand and J. J. Sninsky, Eds., 1999, Academic Press.

As a particular implementation of the approach described here, we describe in detail a procedure for synthesis of first strand cDNA for use in PCR. This procedure can be used for both whole blood RNA and RNA extracted from cultured cells (i.e. THP-1 cells).

Materials (1) Applied Biosystems TAQMAN Reverse Transcription Reagents Kit (P/N 808–0234). Kit Components: 10× Taq-Man RT Buffer, 25 mM Magnesium chloride. deoxyNTPs mixture, Random Hexamers, RNase Inhibitor, MultiScribe Reverse Transcriptase (50 U/mL) (2) RNase/DNase free water (DEPC Treated Water from Ambion (P/N 9915G), or equivalent)

Methods

1 Place RNase Inhibitor and MultiScribe Reverse Transcriptase on ice immediately. All other reagents can be thawed at room temperature and then placed on ice.

2 Remove RNA samples from −80° C. freezer and thaw at room temperature and then place immediately on ice.

3 Prepare the following cocktail of Reverse Transcriptase Reagents for each 100 µL RT reaction (for multiple samples, prepare extra cocktail to allow for pipetting error):

|  | 1 reaction (µL) | 11X, e.g. 10 samples (µL) |
| --- | --- | --- |
| 10X RT Buffer | 10.0 | 110.0 |
| 25 mM MgCl2 | 22.0 | 242.0 |
| dNTPs | 20.0 | 220.0 |
| Random Hexamers | 5.0 | 55.0 |
| RNAse Inhibitor | 2.0 | 22.0 |
| Reverse Transcriptase | 2.5 | 27.5 |
| Water | 18.5 | 203.5 |
| Total: | 80.0 | 880.0 (80 µL per sample) |

4 Bring each RNA sample to a total volume of 20 µL in a 1.5 mL microcentrifuge tube (for example, for THP-1 RNA, remove 10 µL RNA and dilute to 20 µL with RNase/DNase free water . . . for whole blood RNA use 20 µL total RNA) and add 80 µL RT reaction mix from step 5.2.3. Mix by pipetting up and down.

5 Incubate sample at room temperature for 10 minutes.

6 Incubate sample at 37° C. for 1 hour.

7 Incubate sample at 90° C. for 10 minutes.

8 Quick spin samples in microcentrifuge.

9 Place sample on ice if doing PCR immediately, otherwise store sample at −20° C. for future use.

10 PCR QC should be run on all RT samples using 18S and β-actin (see SOP 200-020.

Example 2

Different inflammatory stimuli give rise to different, baseline profile data sets so that the calibrated selected profiles for different agents in the same class of anti-inflammatory result in different signature profiles.

Figure 11A:
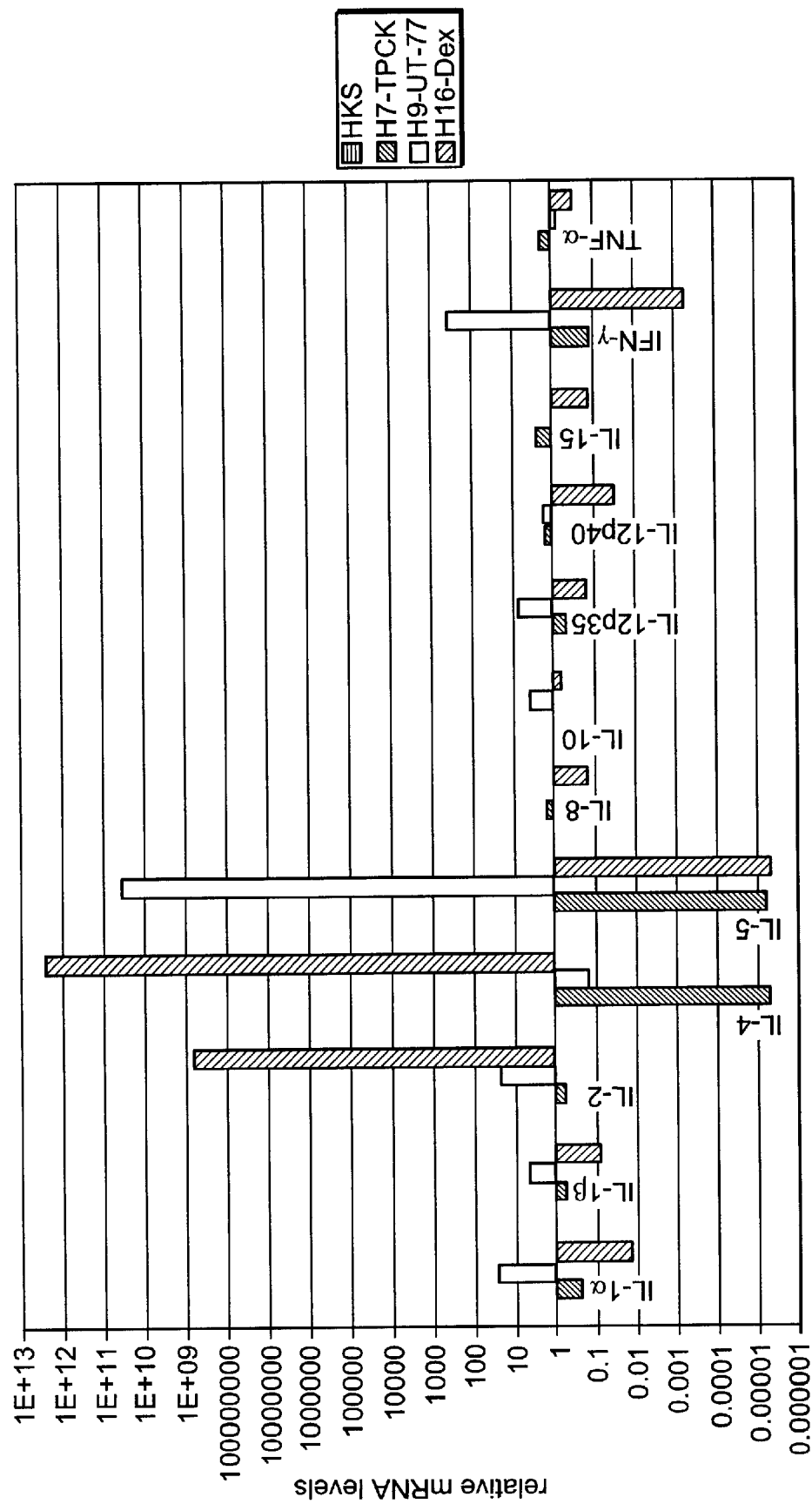
FIG. 11 is a bar graph that shows a graphical representation in the form of a histogram representing calibrated profile data sets based on quantitative expression of RNA in cells of a whole blood sample using a panel of 12 constituents where each constituent corresponds to a unique gene locus. (a) The blood sample is stimulated ex vivo with heat killed staphylococci are further exposed H7-TPCK, H9-UT-77, or H16-Dex as indicated. The baseline profile data set is a blood sample stimulated ex vivo (in vitro) with heat killed staphylococci (b) The blood sample is stimulated ex vivo with lipopolysaccharide (LPS) and is then further exposed to compounds H7-TPCK, H9-UT-77, or H16-Dex as indicated.
Figure 11B:
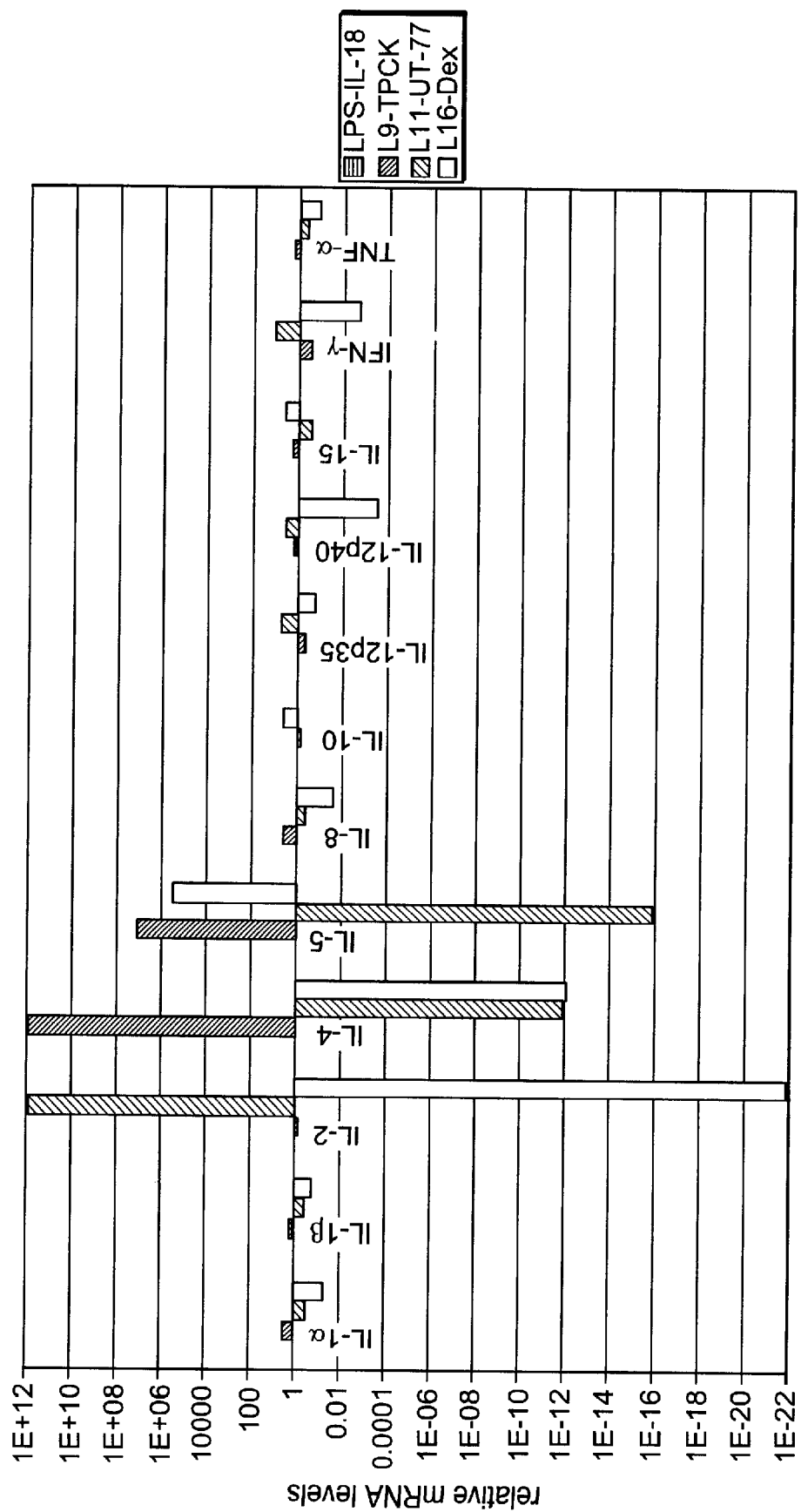

FIGS. 11(a) and 11(b) show different inflammatory stimuli give rise to different, baseline profile data sets that may be used in determining the calibrated selected profile data sets for the three anti-inflammatory agents tested, and the resulting different signature profiles. The different profiles reflect the difference in the molecular targets and mechanisms of action of the three agents derived from a single class of therapeutics, anti-inflammatory agents. FIG. 11(a) also illustrate the extraordinary range of detection (y-axis) from less than 10 fold difference from the calibrated profile with respect to some constituents to a change of $10^{13}$ (10E13) in gene expression of one constituent (indeed the change for a constituent in FIG. 11(b) is $10^{-22}$) when compared to the calibrator. Comparison to the calibrator results in gene expression profiles that are increased, decreased, or without change from the calibrated set.

FIG. 11(a) shows relative gene expression (mRNA synthesis) in heat-killed staphylococci (HKS)-stimulated cells, and the effect of three different compounds (TPCK, UT-77, and "Dex", or dexamethasone). Compound TPCK caused a 10-fold decrease in relative IFN-γ expression, and 100,000-fold decreases in IL-4 and IL-5 expression. Further, compound UT-77 caused even greater magnitude of increases in relative expression of the gene encoding IL-5, and more modest increases in IL-1 expression (more than 10-fold) and IFN-γ. Such effects can be highly significant in disease etiologies and outcomes, and have predictive value concerning the usefulness as therapeutic agents of these compounds or similar chemical entities or chemicals that act similarly. HKS cells may be used as an in vitro model of Gram-positive bacterial infection.

FIG. 11(b) displays analyses of expression of the 12 genes in lipopolysaccharide-(LPS)-treated cells, an in vitro model of Gram-negative bacterial infection. These data include several striking contrasts to the data in FIG. 11(a). Thus treatment with the therapeutic agent Dex caused a striking decrease in expression of the IL-2 gene in LPS-treated cells, and a striking increase in IL-2 expression in HKS-treated cells. Strikingly large differences in gene expression in the differently stimulated cells can be seen for the IL-4 and the IL-5 genes. Expression of the gene for IFN, in contrast, responded similarly in cells treated by either of the stimuli and any of the therapeutic agents.

By these criteria, expression of the genes for IL-2, IL-4 and IL-5 were observed to be candidate markers or surrogate markers in cell model systems to distinguish responses of the cells to Gram-positive and Gram-negative bacterial infection.

Example 3

A single therapeutic agent for treating a particular condition can be differentiated from a second therapeutic agent that also treats the particular condition by a signature profile for a given selected panel of gene loci.

FIG. 12 shows a calibrated profile data set for a panel having 8 constituents that are indicative of a biological condition that includes inflammation. The profiles are shown for three different anti-inflammatory agents-methotrexate, meclofenamate and methylprednisolone. The calibrated profile data sets for each agent as shown represents a signature profile for that agent. This signature profile may serve as a device for establishing quality control for a batch of the agent. Indeed, it is envisaged that compounds or classes of compounds on the market or in development may be characterized by a signature profile. The signature profile may be represented in a graphical format, more particularly as a bar graph as provided in FIG. 12. For FIG. 12, an ex vivo sample was tested. A sample of blood was taken from the subject. Aliquots of the sample were subjected to lipopolysaccharide (LPS) ex vivo. After 30 minutes, the anti-inflammatory agent as indicated was added to an aliquot of the sample of blood and after about another 4 hours, the expression of the panel of genes (Il-1a, Il-2, Il-8, Il-10, Il-12p35, Il-12p40, IL-15, IFN-Gamma and TNF-a) was determined. Although the calibrated profile of methotrexate and meclofenamate were similar, the calibrated profile of methylprednisolone was substantially different. Differences may be reflective of the differences of the mechanisms or target(s) of action of this agent within the general class of anti-inflammatory compounds. The baseline is the profile data set for lipopolysaccharide absent any additional agents.

Example 4

There is relatively low variability with respect to the profile within a single individual over time when the calibrated selected profile is determined from the measurement of gene expression across many gene loci that have been appropriately induced.

Figure 13A:
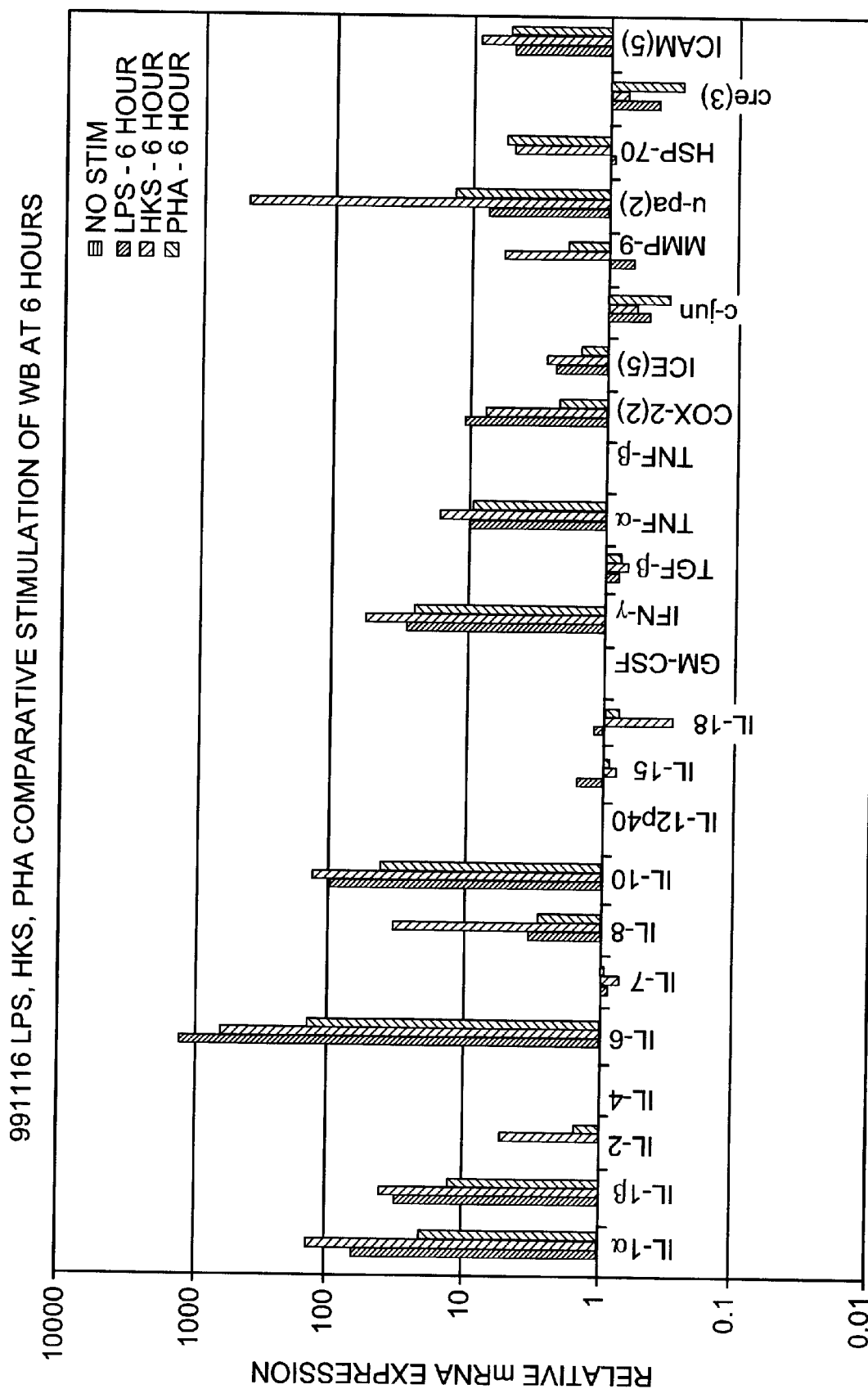
FIG. 13 are bar graphs with a logarithmic axis that shows a graphical representation of calibrated profile data sets for two different samples of whole blood (a) 991116 and (b) 991028 reflecting the biological condition of the cells using a panel of 24 members, each member corresponding to a gene locus, the baseline profile data set being derived from untreated cells. The calibrated data sets for cells exposed for six hours to three inflammation inducing agents (lipopolysaccharide, heat killed staphylococci, and phytohemagglutinin) are compared for each sample. (c) shows a direct comparison of LPS stimulated 991116 with respect to 991028 as the baseline profile data set (d) shows a direct comparison between unstimulated 991116 and 991028.
Figure 13B:
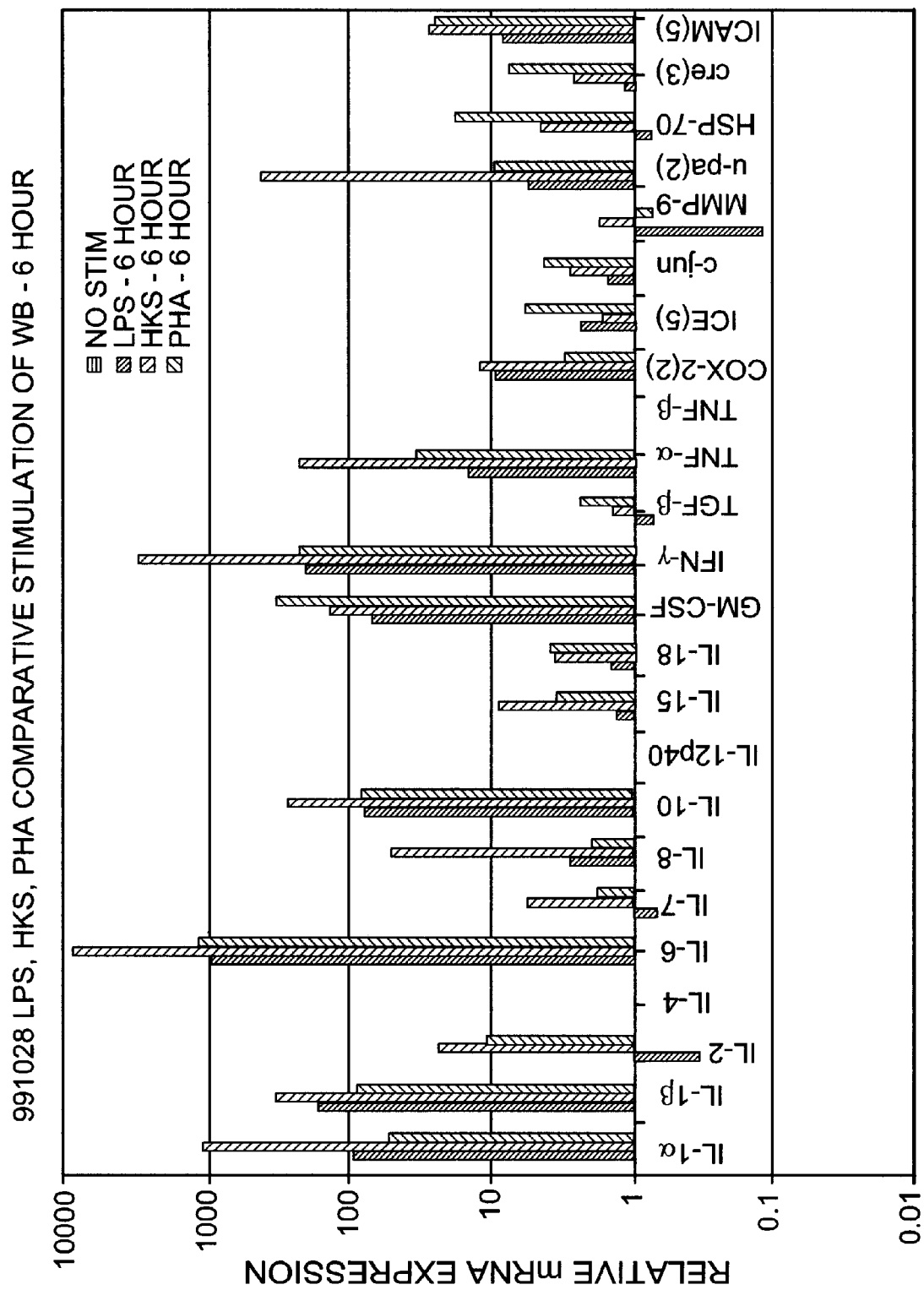
Figure 13C:
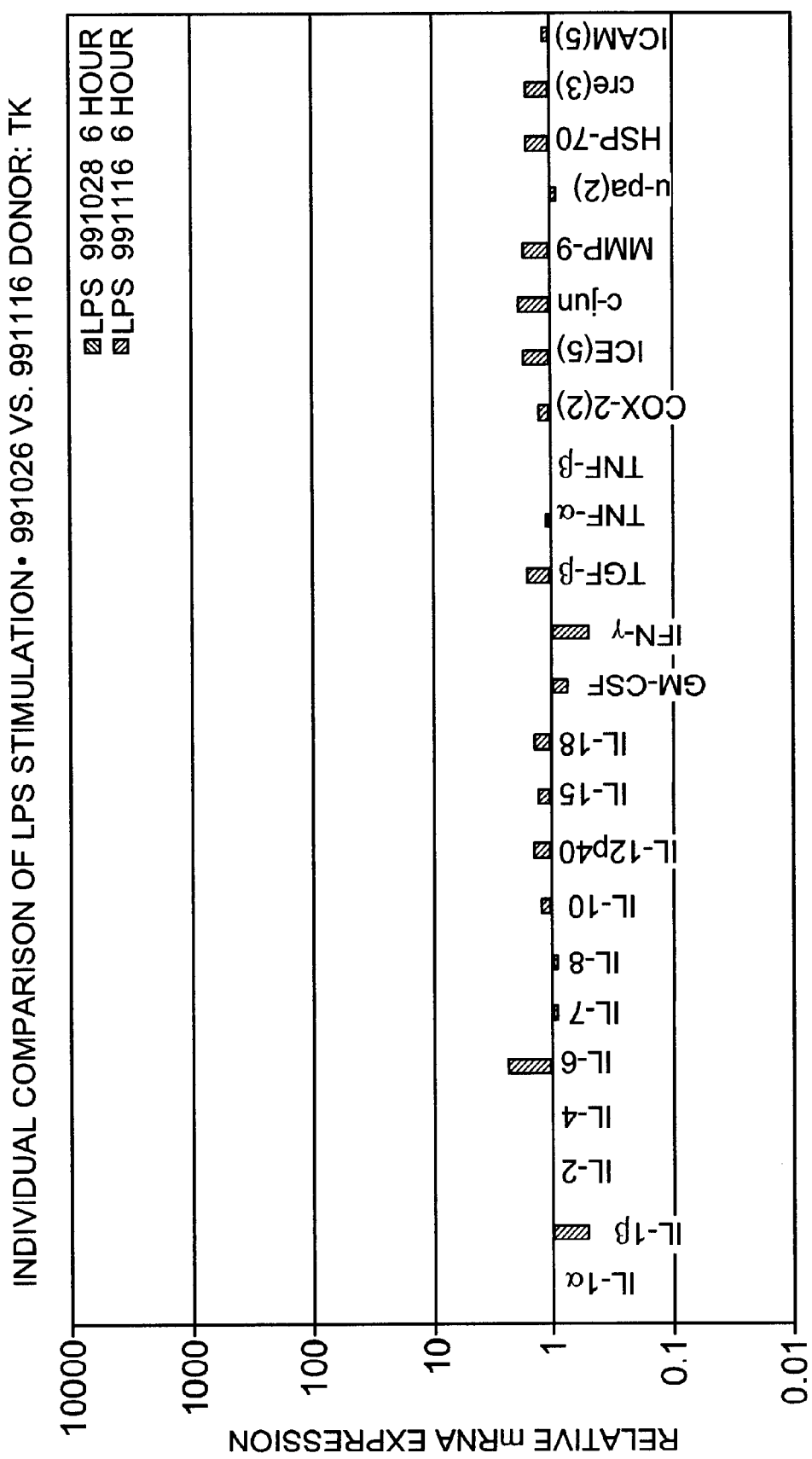
Figure 13D:
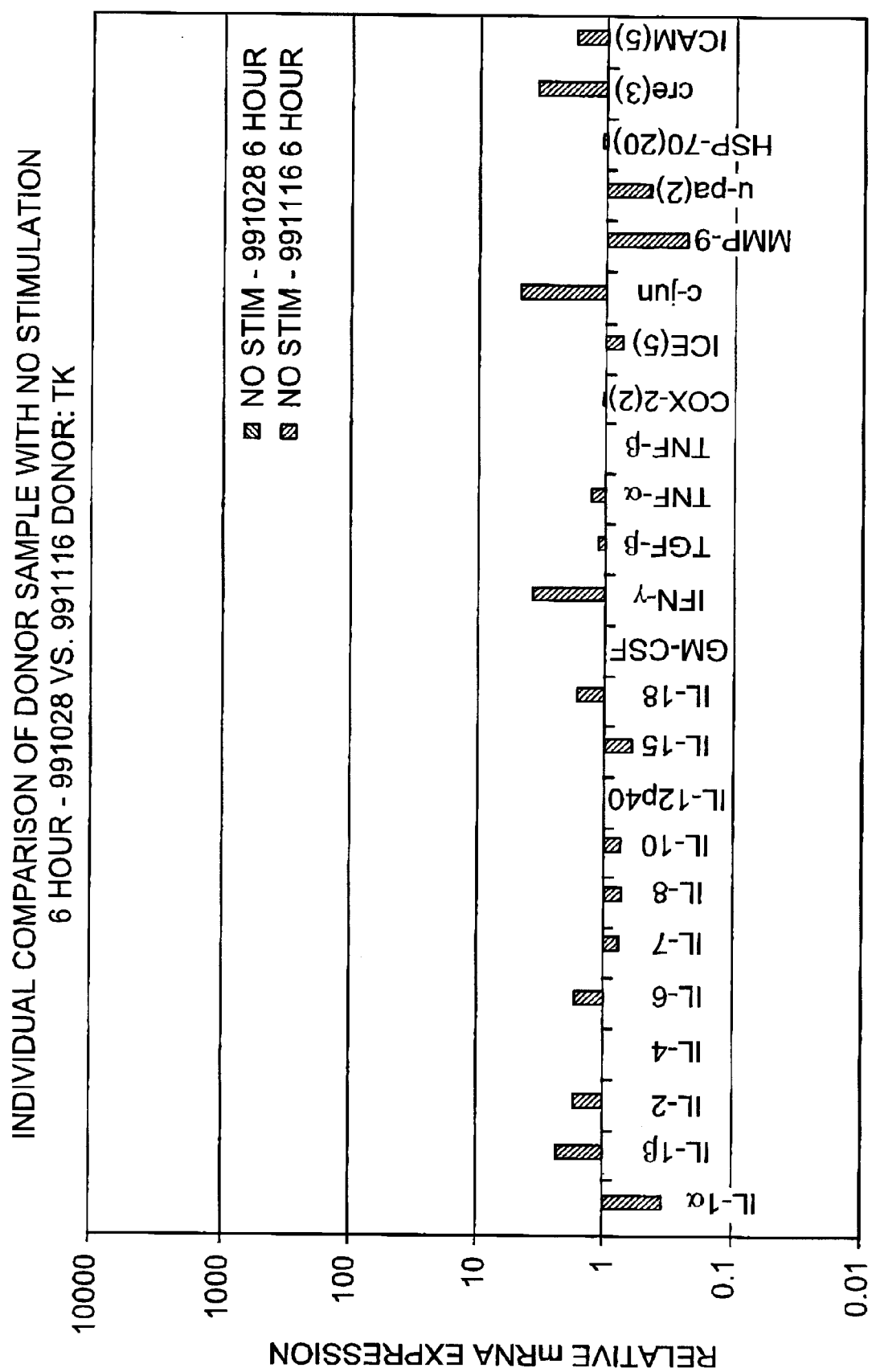

FIGS. 13(a), 13(b), and 13(c) show graphical representations of calibrated selected profile data sets for two different samples of whole blood. Heparinized whole blood from a single normal healthy volunteer was collected on two separate occasions of more than 2 weeks apart. FIG. 13a, for sample 991116, and FIG. 13b, for sample 991028, reflect the biological condition of the tested cells from the single donor using a selected panel (i.e., the inflammation selected panel) of 24 members, in response to stimulation with one of three different agents. The baseline in this example is derived from untreated cells obtained from the same individual. The calibrated profiles are shown for cells exposed for 4 to 6 hours to lipopolysaccharide (LPS), heat-killed Stapylococci (HKS), and phytohemagglutinin (PHA). FIG. 13c shows a direct comparison of LPS-stimulated blood sample 99116 with respect to blood sample 991028, i.e., 991028 is used as the calibrator or baseline profile data set. The messenger RNA levels measured on Oct. 28, 1999 were used to compare the levels of messenger RNA measured on Nov. 16, 1999. A perfect identity of RNA levels would be represented by a flat line at unity. These data show that for baseline gene expression, there can be as much as an 8 fold difference (c-jun) in messenger RNA levels. However, for most of the genes measured, when there is no known substantial physiological change in the subject, the levels of messenger RNA measured on one day are similar to those measured on a different day. Changes in gene expression, whether mRNA or protein, in excess of 10–20% may be reflective of biological changes in the subject even though traditional clinical measurements may not identify such changes. FIG. 13(d) is similar to FIG. 13(c) except that the cells were not stimulated with LPS.

FIGS. 13(a) through 13(d) document the relatively low variability with respect to the profile within a single individual over time in similar physiological conditions when the calibrated selected profile is determined from the measurement of gene expression across many gene loci that have been appropriately induced. The figures illustrate (1) the class-specific effects (generally inflammatory as determined by the effect on pro-inflammatory gene loci, e.g. TNF-alpha, IL-1 alpha and IL-1 beta ), (2) the agent-specific effects quantitative differences between each of the agents at the same gene loci (e.g., IL-2) and (3) reproducible and therefore predictable effects on the subject population, TK (FIG. 13c).

Example 5

Similarities and differences in the effect of a single agent on cell populations their biological condition.

Ex-vivo gene expression analysis can be performed by obtaining the blood of a subject for example by drawing the blood into a vacutainer tube with sodium heparin as an anticoagulant. An anti-inflammatory such as 3-methyl-prednisolone at a final concentration of 10 micromolar was added to blood in a polypropylene tube, incubated for 30 minutes at 37° C. in 5% $CO_2$. After 30 minutes a stimuli such as LPS at 10 ng/mL or heat killed staphlococcus (HKS) at 1:100 dilution was added to the drug treated whole blood. Incubation continued at 37° C. in 5% $CO_2$ for 6 hours unless otherwise indicated. Erythrocytes were lysed in RBC lysis solution (Ambion) and remaining cells were lysed according to the Ambion RNAqueous-Blood module (catalog #1913). RNA was eluted in Ambion elution solution. RNA was DNAsed treated with 1 unit of DNAse I (Ambion #2222) in 1X DNAse buffer at 37° C. for 30 minutes. In this example, first strand synthesis was performed using the Applied Biosystems TaqMan Reverse Transcriptase kit with Multi-Scribe reverse transcriptase (catalog #N808–0234). Quality check of RT reactions were performed with Taqman PCR chemistry using the 18S rRNA pre-developed assay reagents (PDAR) from Applied Biosystems (part #4310893E). PCR assay of Source Selected Profiles were performed on 6 to 24 genes in four replicates on the Applied Biosystems 7700. PCR assays were performed according to specifications outlined with the PDAR product. Relative quantitation of the gene of interest was calibrated against 18S rRNA expression as described in Applied Biosystems product User Bulletin 2 (1997) and elaborated in Hirayama, et al (Blood 92, 1998:46–52) using 18S instead of GAPDH. Relative quantitation of the mRNA was measured by the difference in threshold cycles between 18S and the gene of interest. This delta $C_T$ was then compared to the normalizing condition, either subject before treatment, or stimuli without drug in an ex-vivo assay to measure "fold induction" represented in the bar graphs (FIG. 14). For example, in the above graph, IFN-levels are 1/50 less on day 3 than before treatment.

Example 6

In Vivo and Ex vivo samples provide comparable signature profiles.

FIG. 15 shows the calibrated profile data set for two subjects (Subject 1 and Subject 2) who have been treated over a three day period with a standard dose of the corticosteroids, dexamethasone. Blood from each subjects was obtained 72 hours later and a quantitative measure of the amount of RNA corresponding to the panel constituents was determined. Although, the calibrated profile data set for each subject was similar for most gene loci, some notable differences were also detected, for example for Il-2, Il-10, Il-6 and GM-CSF. A calibrated profile data set is also shown for comparison for an ex vivo sample of blood from sample 1 prior to treatment with corticosteroid where the ex vivo sample is subjected to an equivalent amount of corticosteroid in vitro as calculated to be the plasma level in the subject. The similarity in the calibrated profile data set for ex vivo samples when compared to in vivo samples provides support for an in vitro assay that will predict the in vivo action of the compound. We have observed a similar comparable effect between in vivo and ex vivo samples infected with an infectious agent, more particularly bacterial or viral agents. We have concluded therefore that the ex vivo samples provide an effective method of determining the effect of a single compound or multiple compounds on a patient, where the multiple compounds may be either used in combination, in parallel or sequentially to optimize the selection of an agent for a biological condition for the subject.

Example 7

Demonstration of reproducibility of an in vitro response with an approved anti-inflammatory on 5 different donor subjects.

Comparison and analysis of the FIGS. 18a through 18e demonstrate the consistency of effect of the stimulus and in vitro treatment with an approved anti-inflanmmatory on 5 different donors (each figure representing a unique donor). The use of a known and tested stimulus results in a highly reproducible gene response in vitro that may be correlated with a predictable in vivo response.

FIGS. 18a–18e provide the results of analysis of 5 donors from which a blood sample has been taken. The blood samples were exposed to a therapeutic agent at various concentrations ranging from 0.1 $\mu$M to 5 $\mu$M, more particularly 0.1 $\mu$M, 0.3 $\mu$M, 1 $\mu$M, 3 $\mu$M and 5 $\mu$M, for a 4 hour period. Different concentrations of the drug resulted in a calibrated profile data set for an inflammation panel at each concentration that was qualitatively different from the next.

Figure 18A:
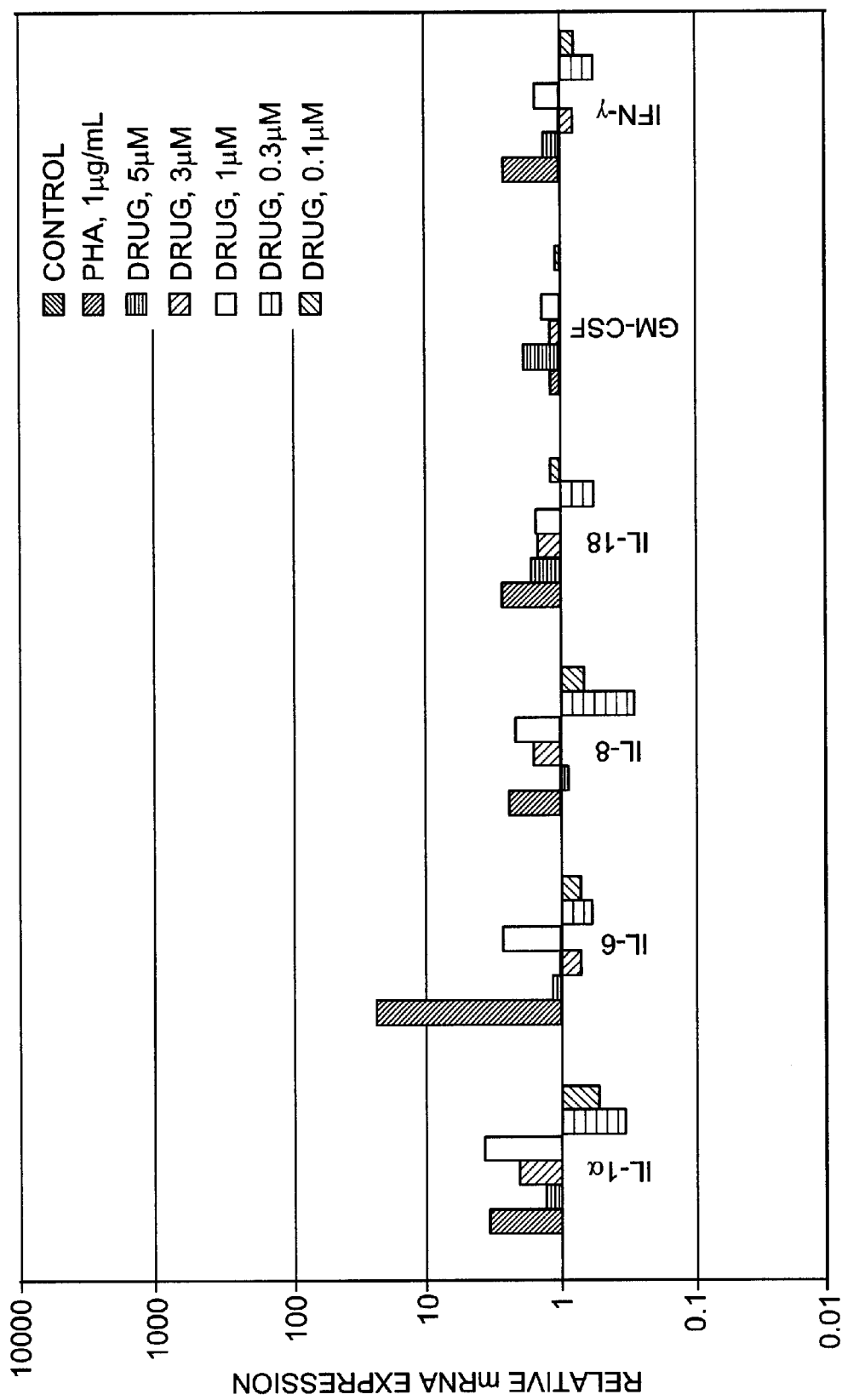
FIGS. 18(a) through 18(e) are bar graphs with a logarithmic axis that show a graphical representation of calibrated profile data sets for each of 5 subjects from which a blood sample has been taken. Each of the blood samples was exposed to the inflammatory agent phytohemagglutinin (PHA) or to a therapeutic agent (anti-inflammatory agent) at different concentrations: 0.1 $\mu$M, 0.3 $\mu$M, 1 $\mu$M, 3 $\mu$M and 5 $\mu$M, for a 4 hour period ex vivo (in vitro) so as to determine the optimum dose for treating the subject. A panel of 6 constituents was used corresponding to 6 gene loci. The baseline profile data set was an untreated sample obtained from the cognate donor.
Figure 18B:
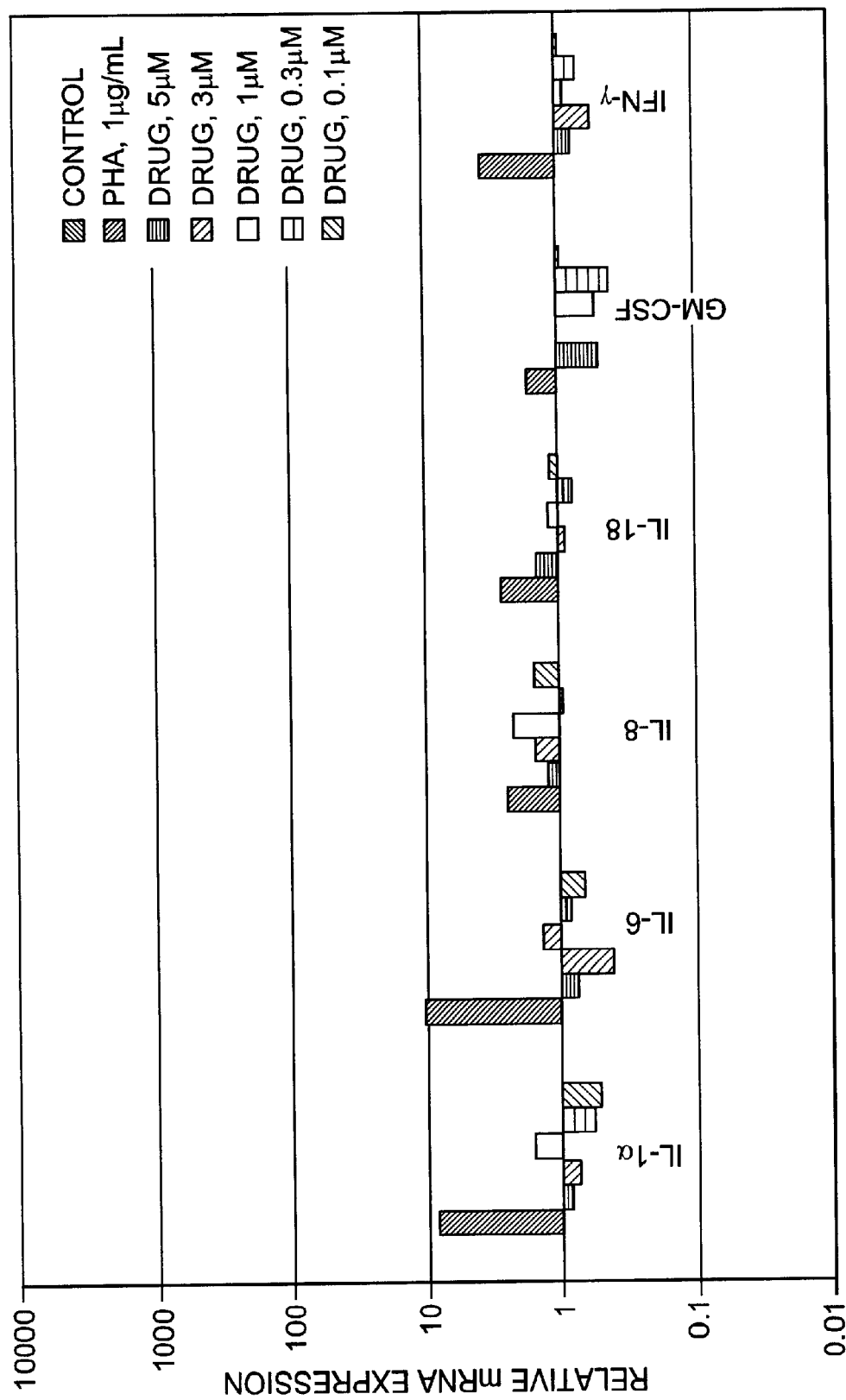
Figure 18C:
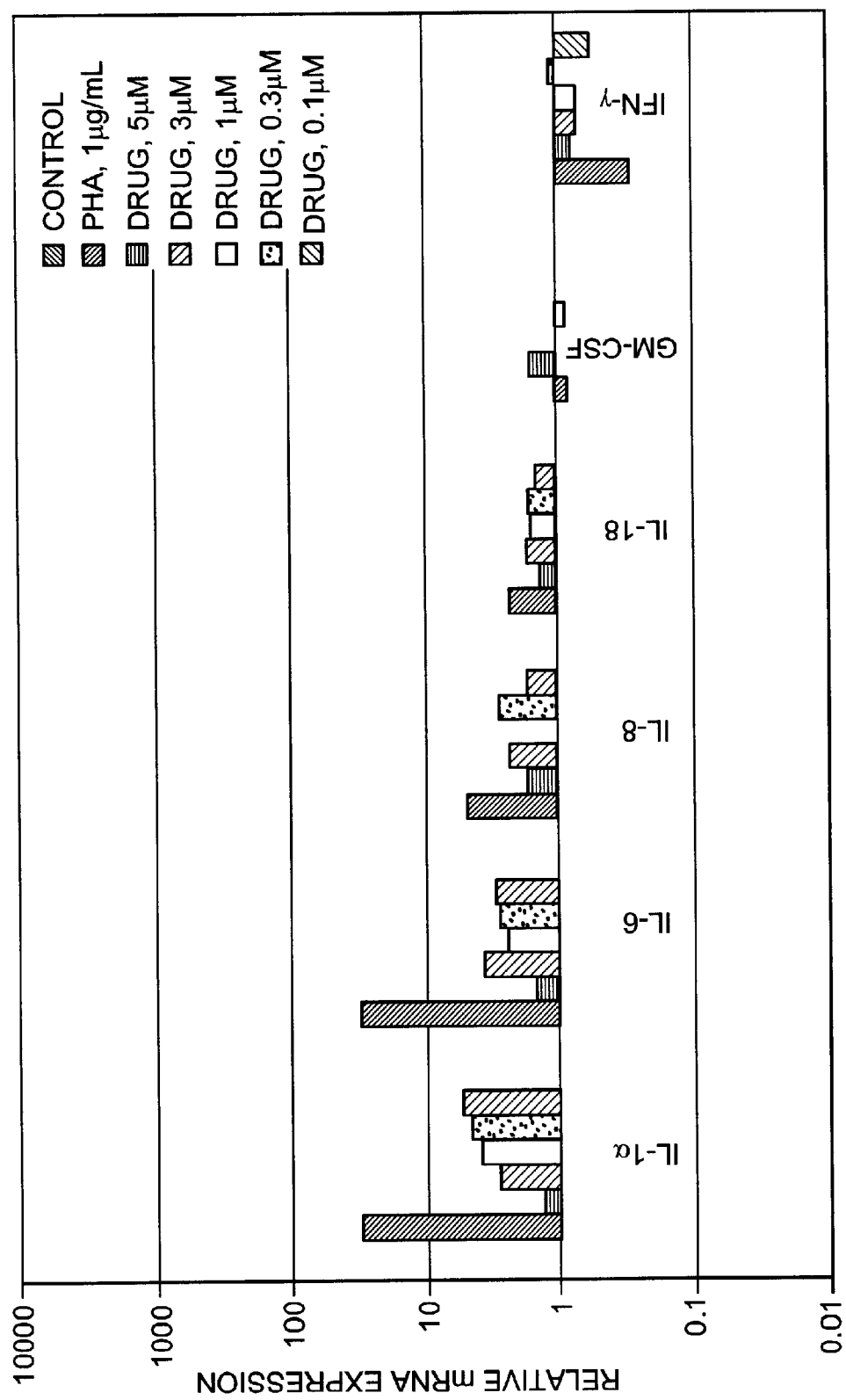
Figure 18D:
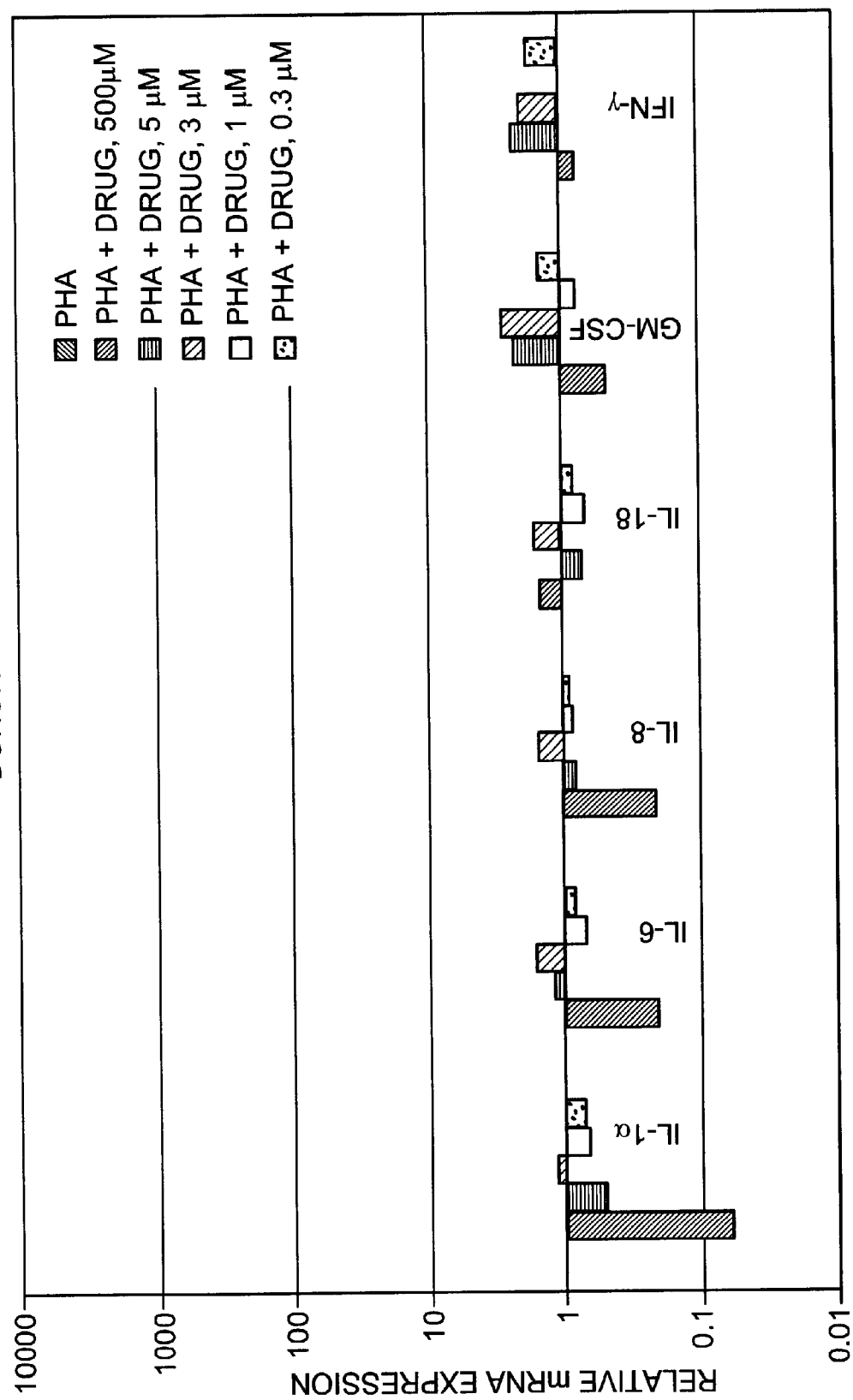
Figure 18E:
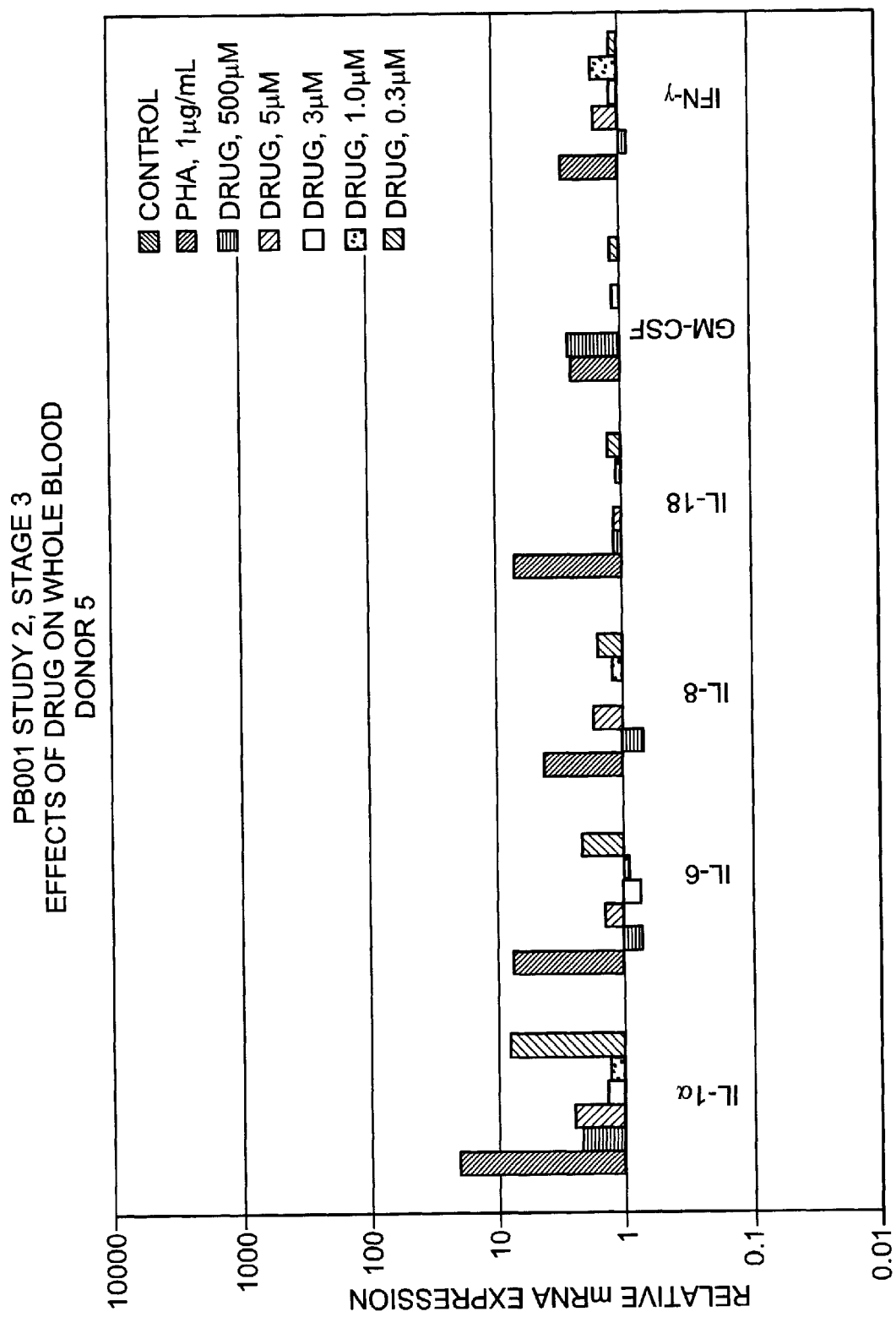
Figure 19A:
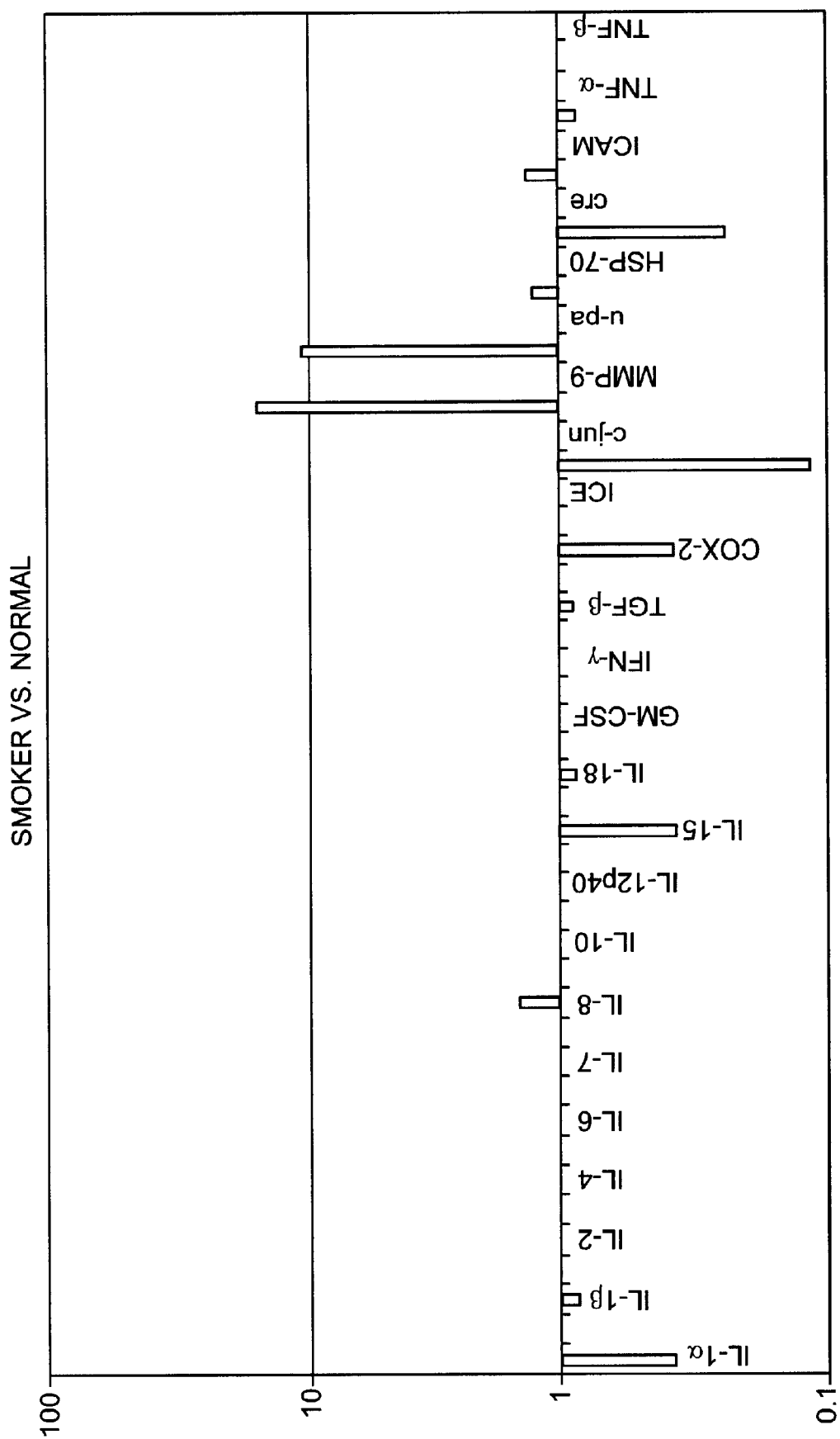
FIG. 19 is a bar graph with a logarithmic axis that shows a graphical representation of calibrated profile data sets for three different subjects having different biological conditions using a panel with 24 constituents. The profile data sets show variability according to these conditions providing the basis for a diagnostic signature panel: (a) shows a calibrated profile data set for a smoker against a baseline for a non-smoker. (b) shows a calibrated profile data set for a subject with chronic obstructive pulmonary disease against a baseline for a subject lacking this disease. The baseline profile data set is derived from a subject that is "normal" with respect to these conditions.
Figure 19B:
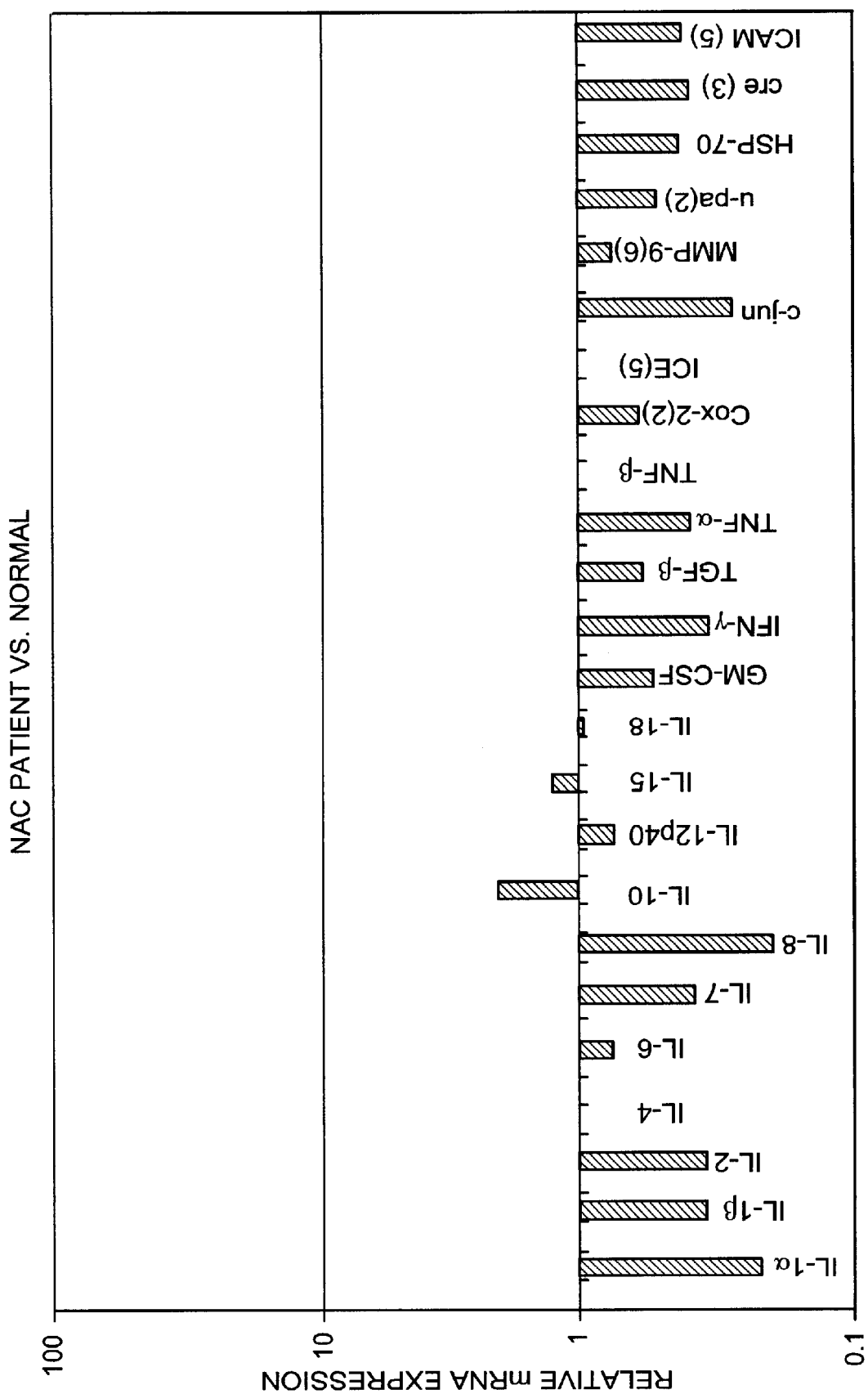

FIG. 18a corresponds to donor 1, FIG. 18b corresponds to donor 2, FIG. 18c corresponds to donor 3, FIG. 18d corresponds to donor 4, and FIG. 18e corresponds to donor 5. Each individual varied from the other and also provided a variable profile for a different concentration. This set of figures illustrates the high level of information obtainable by calibrated profile data sets.

Example 8

A calibrated profile data set may provide a signature profile for a complex mixture of compounds.

FIG. 21 illustrates the effect of three different anti-inflammatory herbs on a selected panel of constituents including constituents of an Inflammation Selected Panel (TNFα, Il-1b, ICAM, Il-8, Il-10, Il-12p40, ICE, cox-2, cox-1 and mmp-3) a cell growth and differentiation selected panel (c-fos, cjun and STAT3), a toxicity selected panel (SOD-1, TACE, GR, HSP70, GST, c-fos, c-jun, INOS) and a liver metabolism selected panel (INOS, cyp-a and u-pa). The cells assayed in FIG. 21 are aliquots of blood from a subject that are exposed ex vivo to lipopolysaccharide and to Echinacea (SPM9910214) Arnica (SPM9910076) and Siberian Ginseng (SPM9910074), each of the nutraceuticals being applied to the blood sample at the same concentration of 200 ug/ml. The baseline is cell sample with lipopolysaccharide in the absence of a nutraceutical. Each nutraceutical (formed from a complex mixture) has a characteristic signature profile just as did the single compound pharmaceutical anti-inflammatory agents. The signature profile may be provided in a graphic form that can be use to identify a herbal while providing information concerning its properties and its efficacy for a single subject or for an average population of subjects.

Example 9

A quality control assay for Echinacea brands using calibrated profile data sets.

Figure 24:
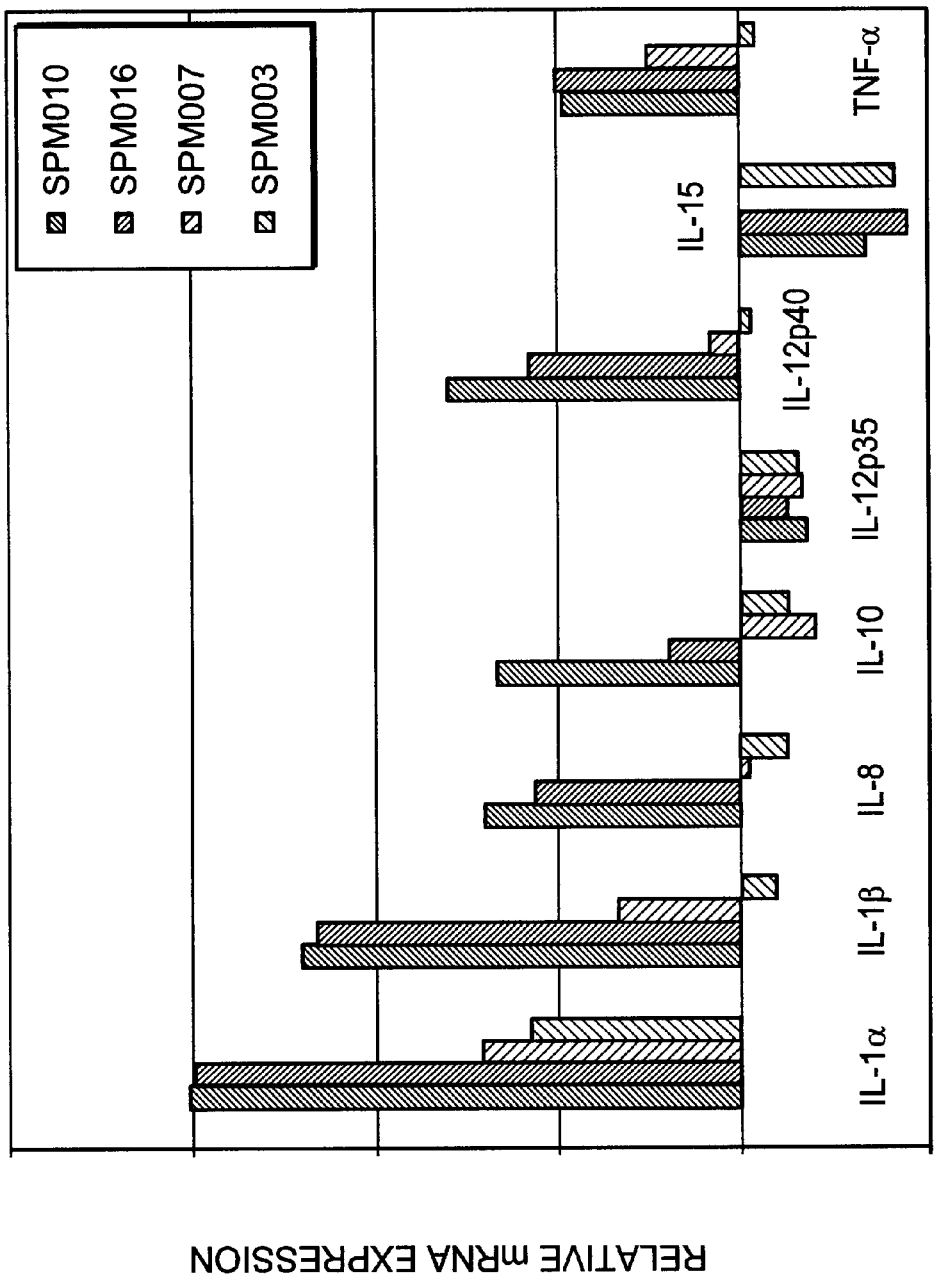
FIG. 24 is a bar graph with a logarithmic axis that shows a graphical representation of calibrated profile data sets for samples of THP-1 cells treated ex vivo with four different commercial brands of Echinacea using a panel of 8 constituents. The baseline profile data set is untreated THP-1 cells.

FIG. 24 shows a graphic representation of the calibrated profile data sets for four different commercial brands of Echinacea. Brands using an Inflammation Selected Panel. As expected, SPM007 and SPM003 gave the signature, calibrated profiles similar to authentic Echinacea. Samples SPM010 and SPM 016, although labeled and sold as Echinacea when tested using the system described in FIG. 14, resulted in signature calibrated profiles that were substantially similar to the profile obtained with lipopolysaccharide alone. Echinacea samples SPM010 and SPM016 were found to have elevated, highly biologically active levels of endotoxin while the LPS levels in SP700 and SP003 were undetectable. A stored signature profile for active Echinacea obtained from a selected panel designed to test efficacy and mode of action, e.g., the inflammation panel, permits evaluation of new batches of Echinacea, differentiation of existing or new brands of Echinacea, guide the isolation and development of new compounds with different or similar activities from a complex compound like Echinacea or may be used in the development of quality assurance in the production, analysis and sale of new or previously marketed compounds. In the example cited, two of the brands of Echinacea SP010 and SP016 result in calibrated profiles that are characteristic of authentic Echinacea.

Example 10

Comparison of three herbal preparations using an indicator cell line.

Figure 25A:
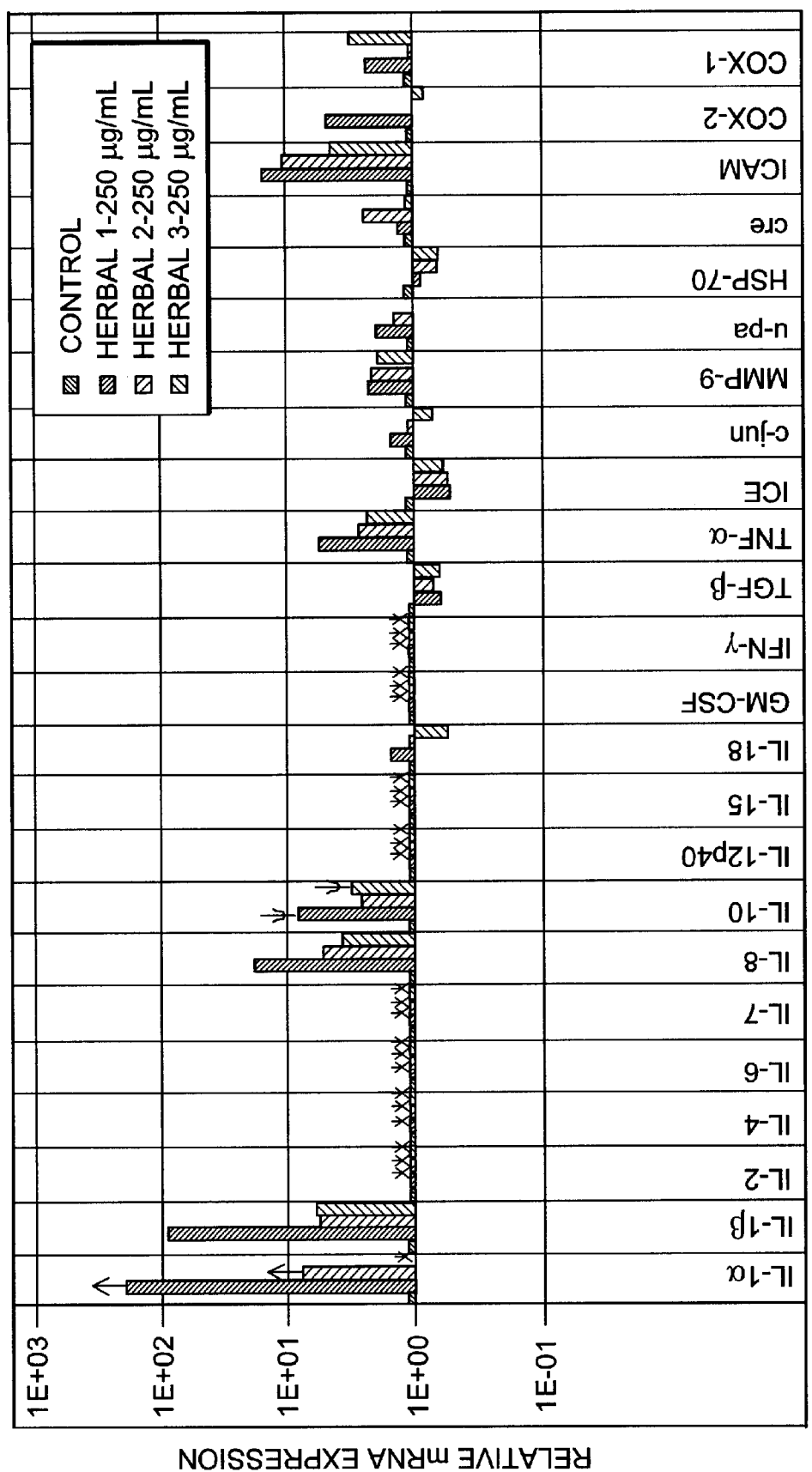
FIG. 25 illustrates the use of the calibrated profile to compare relative efficacy across brands, or different formulations. Calibrated profile data sets for herbal preparations from different manufacturing sources with respect to an indicator monocytic cell line (THP-1) are shown graphically, the baseline profile data set being THP-1 cells absent the herbal. (a) Three commercial herbal Echinacea preparations at 250 ($\mu$g/ml); (b) three herbal preparations at different concentrations (250 $\mu$g/ml, 50 $\mu$g/ml and 3–10 $\mu$g/ml) (c) four commercial Echinacea brands at 250 $\mu$g/ml).

FIGS. 25(a) through 25(c) provide calibrated profile data sets for three herbal preparations with respect to an indicator cell line (THP-1) rather than a blood sample from a subject. In FIG. 25(a), the baseline is the profile data set for THP-1 cells absent the herbal while the histograms represent the calibrated profile data sets for the same herbal from three different manufacturing sources of the same herb at 250 ug/ml. Gene expression results are shown on a log scale. Similar to the observation in FIG. 14, these demonstrate that similarly labeled compounds obtained from different sources have demonstrable and quantifiable differences in calibrated profiles using a specific panel, e.g., the inflammation selected panel designed to obtain information about the expression of gene products related to inflammation and infection. This suggests that the compounds likely have different efficacies when used for specific purposes.

FIG. 25(b) provides a comparison of the calibrated profile of a single herb at three concentrations using the indicator cell line of THP-1. The baseline profile data set is untreated THP-1 cells. Analysis of the data suggests a concentration-dependent response in the indicator cell lines which, although demonstrated here, may be indicative of a similar response in subjects.

FIG. 25(c) provides a comparison of four commercial Echinacea brands used at the same concentration and tested against a panel of constituents using a THP-1 cell line as an indicator cell population. Differential expression, as revealed, for example, by inspection or calculation of differences in the calibrated profiles, allows direct comparisons of complex compounds to be made. For example, analysis of the differences in the calibrated profiles may be used to guide compound isolation and development, product differentiation in the marketplace, or used by the consumer or health professional to guide the individualized choice of a single compound from a class of similar compounds that may be suited for a particular biological condition.

Example 11

Set up of a 24-gene Human Selected Panel for Inflammation.
Materials
1 20× Primer/Probe Mix for each gene of interest.
2 20× Primer/Probe Mix for 18S endogenous control.
3 2× Taqman Universal PCR Master Mix
4 cDNA transcribed from RNA extracted from cells
5 Applied Biosystems 96-Well Optical Reaction Plates
6 Applied Biosystems Optical Caps, or optical-clear film
7 AB Prisma 7700 Sequence Detector Methods 1 Make stocks of each Primer/Probe mix containing the Primer/Probe for the gene of interest, Primer/Probe for 18S endogenous control, and 2× PCR Master Mix as follows. Make sufficient excess to allow for pipetting error e.g. approximately 10% excess. The following example illustrates a typical set up for one gene with quadruplicate samples testing two conditions (2 plates).

|  | 1X (1 well) | 9X (2 plates worth) |
| --- | --- | --- |
| 2X Master Mix | 12.50 | 112.50 |
| 20X 18S Primer/Probe Mix | 1.25 | 11.25 |
| 20X Gene of interest Primer/Probe Mix | 1.25 | 11.25 |
| Total | 15.00 | 135.00 |

2 Make stocks of cDNA targets by diluting 95 μl of cDNA into 2000 μl of water. The amount of cDNA to be adjusted to give Ct values between 10 and 18.

3 Pipette 15 μl of Primer/Probe mix into the appropriate wells of a Applied Biosystems 96-Well Optical Reaction Plate.
4 Pipette 10 μl of cDNA stock solution into each well of the Applied Biosystems 96-Well Optical Reaction Plate.
5 Seal the plate with Applied Biosystems Optical Caps, or optical-clear film.
6 Analyze the plate on the AB Prism 7700 Sequence Detector.

In Examples 12 through 19 below, procedures analogous to those of Examples 1 and 11 were followed to determine relative mRNA expression.

Example 12

Calibrated profile data sets, using a subset of the Inflammation Selected Panel, show the effect of administration of a steroid.

Figure 26A:
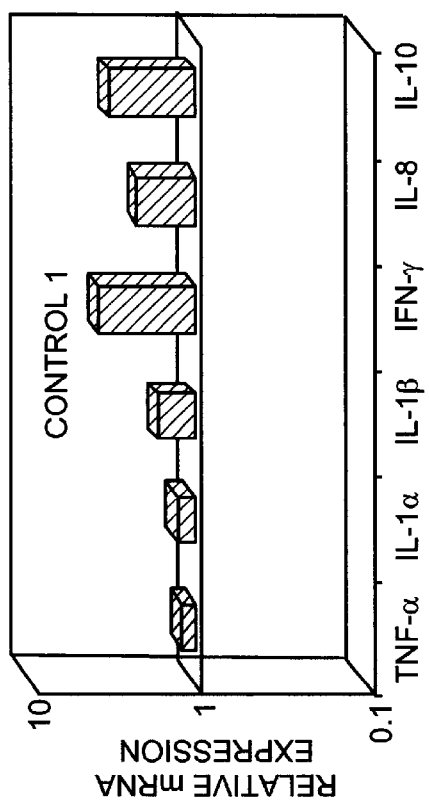
FIGS. 26(a) through 26(d) illustrate calibrated profile data sets, using a subset of the Inflammation Selected Panel, that show the effect of administration of a steroid.
Figure 26B:
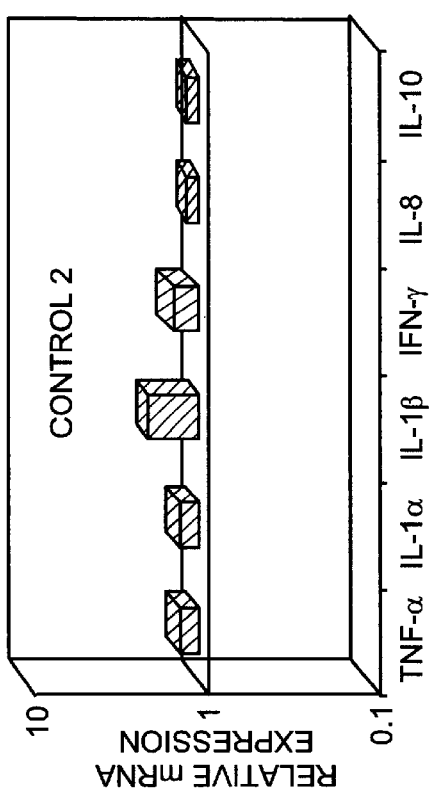
Figure 26C:
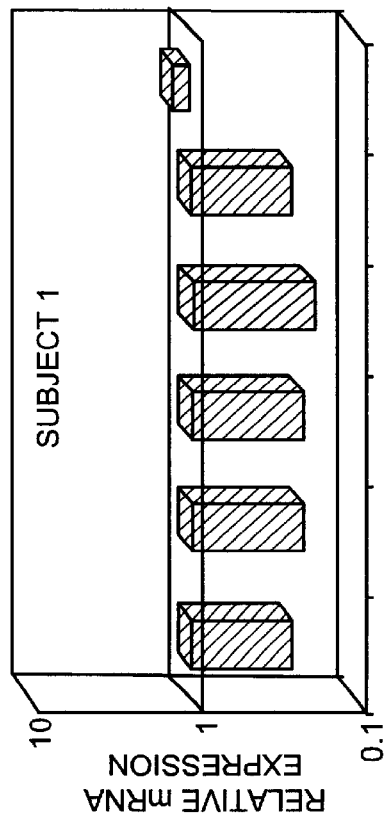
Figure 26D:
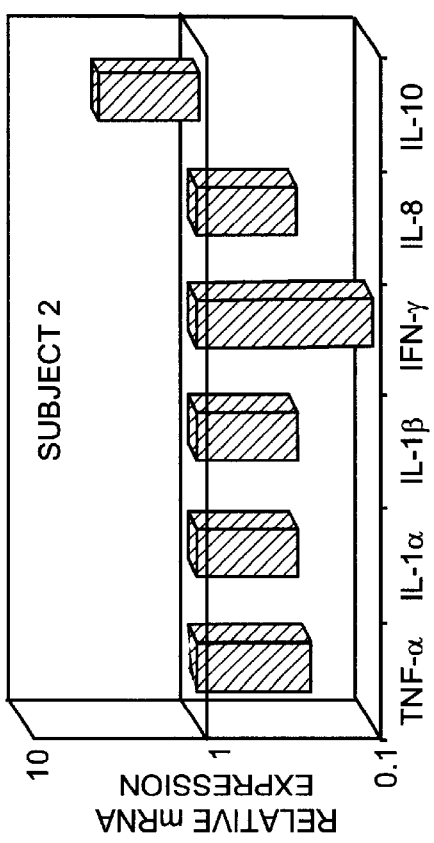

In FIGS. 26(a) and 26(c), subjects 1 and 2 respectively have been subjected to a course of administration of methylprednisone twice a day for three consecutive days. In FIGS. 26(b) and 26(d), two other individuals, identified as control 1 and control 2 respectively, were administered a placebo over a corresponding period. In each case, the blood samples of the individuals were taken prior to the course of administration and immediately following the course of administration. The graphs of these each of these figures show the relative concentration of each constituent of a subset of the Inflammation Selected Panel, the subset being chosen for its ability to discriminate as to the effect of anti-inflammatory agents. For each constituent, the post-administration concentration is shown as a ratio in relation to its pre-administration concentration; hence the baseline of 1 is indicative of the same concentration of the constituent before and after administration, and the presence of a bar below the baseline indicates a post-administration drop in concentration of the constituent. FIGS. 26(a) and 26(c) show that the response of subjects 1 and 2 to the administration of the steroid are qualitatively and quantitatively similar-indeed, strikingly similar. Moreover, and in contrast, the responses of controls 1 and 2 to the placebo are markedly distinct from the responses of subjects 1 and 2.

Example 13

Calibrated profile data sets, using a subset of the Inflammation Selected Panel, provide a comparison of the effects of administration of methylprednisone and Ibuprofen. In this example, FIGS. 27(a) and 27(c) are identical to FIGS. 26(a) and 26(c), and show the responses of subjects 1 and 2 respectively to the administration of methylprednisone. FIGS. 27(b) and 27(d) show the responses of the same subjects, namely subjects 1 and 2 respectively, to the administration of high-dose Ibuprofen (800 mg administered three times per day over a three-day period). (FIGS. 27(b) and 27(d) use the same conventions as FIGS. 27(a) and 27(c) in showing post-administration concentration of constituents relative to pre-administration concentration.) It can be seen from these figures that the responses of the subjects to Ibuprofen are qualitatively and quantitatively similar-again, strikingly similar. Moreover, the responses of the subjects to Ibuprofen are distinct from the responses of the subjects to methylprednisone. In fact, the distinct pattern of response to Ibuprofen correlates with other information known about Ibuprofen. For example, IL-1-β is known to be of importance in responding to joint destruction, and Ibuprofen here is shown as not raising the level (and in the case of subject 2, lowering the level) of IL-1-β expression. And Ibuprofen is known to be not very effective in treating joint destruction. Similarly, IL-10 activity is associated with anti-inflammatory activity and is useful in addressing bowel inflammatory disease; Ibuprofen here is shown as in fact depressing the level of IL-10 expression. These phenomena are consistent with the fact that Ibuprofen is known to be ineffective in addressing bowel inflammatory disease.

Example 14

Calibrated profile data sets, using a subset of the Inflammation Selected Panel, identify chronic obstructive pulmonary disease (COPD) patients.

Figures 28A, 28B, 28C, 28D:
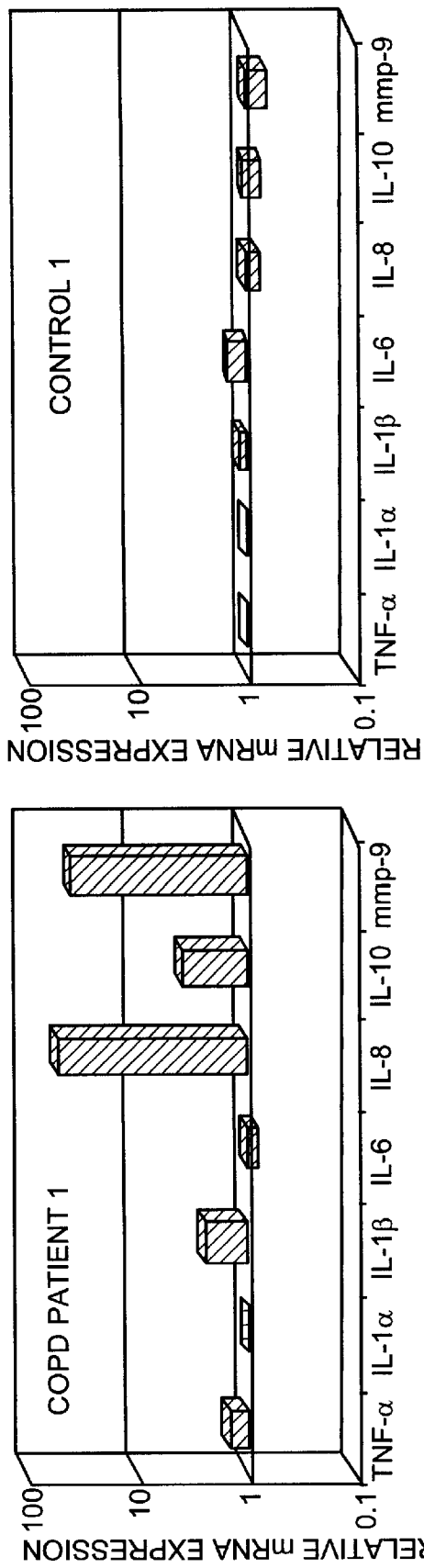
FIGS. 28(a) through 28(d) illustrate calibrated profile data sets, using a subset of the Inflammation Selected Panel, in identifying chronic obstructive pulmonary disease (COPD) patients.

The graphs of these each of FIGS. 28(a) through 28(d) show the relative concentration of each constituent of a subset of the Inflammation Selected Panel, the subset being chosen for its ability to discriminate as to the presence of COPD. For each constituent, the concentration is shown as a ratio in relation to a concentration that is normative of the concentrations of the constituent in a population of healthy subjects. Thus for any constituent, a baseline level of 1 corresponds to a normal concentration. FIGS. 28(a) and 28(c) show the relative concentrations of constituents in COPD patients 1 and 2 respectively, while FIGS. 28(b) and 28(d) show the relative concentrations of constituents in two healthy individuals identified as control 1 and control 2 respectively. Indeed, FIGS. 28(b) and 28(d) show levels of constituents in controls 1 and 2 as being close to population normals, whereas FIGS. 28(a) and 28(c) show levels of constituents in COPD patients 1 and 2 as being dramatically different from normal levels.

Example 15

Evaluations of the effects of drug exposure performed in vitro correspond closely with evaluations performed in vivo, employing in each case calibrated profile data sets, using a subset of the Inflammation Selected Panel.

FIGS. 29(a) and 29(b) present graphs showing response to the administration of methylprednisone. The response shows the relative concentration of each constituent of a subset of the Inflammation Selected Panel, the subset being chosen for its ability to discriminate as to the effect of anti-inflammatory agents. For each constituent illustrated, the darker bar (on the right) shows the in vivo response of a subject to a course of administration of methylprednisone twice a day for three consecutive days. In the in vivo cases, a blood sample of the subject was taken prior to the course of administration and immediately following the course of administration, the constituents were measured, and the responses are shown in FIGS. 29(a) and 29(b). The post-administration concentration of each constituent is shown as a ratio in relation to its pre-administration concentration; hence the baseline of 1 is indicative of the same concentration post-administration as pre-administration. The procedures of FIGS. 29(a) and 29(b) were conducted on two different occasions a year apart. At the same time that each in vivo procedure was conducted, methylprednisone was also administered in vitro to a sample of the blood of the same subject. For each constituent illustrated in each of FIGS. 29(a) and 29(b), the lighter bar (on the left) shows the in vitro response of the sample to the administration of the drug. Again, the post-administration concentration of each constituent is shown as a ratio in relation to its pre-administration concentration.

What is remarkable about the results shown in FIGS. 29(a) and 29(b) is that in each procedure, the in vitro response is strikingly similar to the in vivo response, in most cases even where the results in vivo differed over time. This result shows the value of in vitro modeling for the evaluation of the effect of the administration of agents using Example 16

The effect of different agents is evaluated using a subset of the Selected Prostate Panel.

In FIG. 30 is shown the response of five different cell lines to the administration of various agents, using a subset of the Selected Prostate Panel (listed in Table 5). This figure also shows broad functions of constituents of the panel.

Example 17

The use of a rat liver metabolism selected panel to measure the effect of a pharmaceutical agent, clofibrate, Male rats were treated with 400 mg/kg/day of clofibrate administered by mouth and the levels of gene expression were measured in liver tissue. Clofibrate is used here because its metabolism in the rat and human liver is well described. As expected, clofibrate induces gene expression at the cyp 1A 1 locus, but the agent also induces expression at a number of other metabolic loci in the selected panel as measured in this cohort of in-bred Sprague-Dawley rats. The ratio of the concentration of each constituent for the clofibrate treated rats is measured with reference to a control (baseline) which is a set of rats treated only with the carrier compound. The resultant selected profile is provided in FIG. 31.

Example 18

Figure 32:
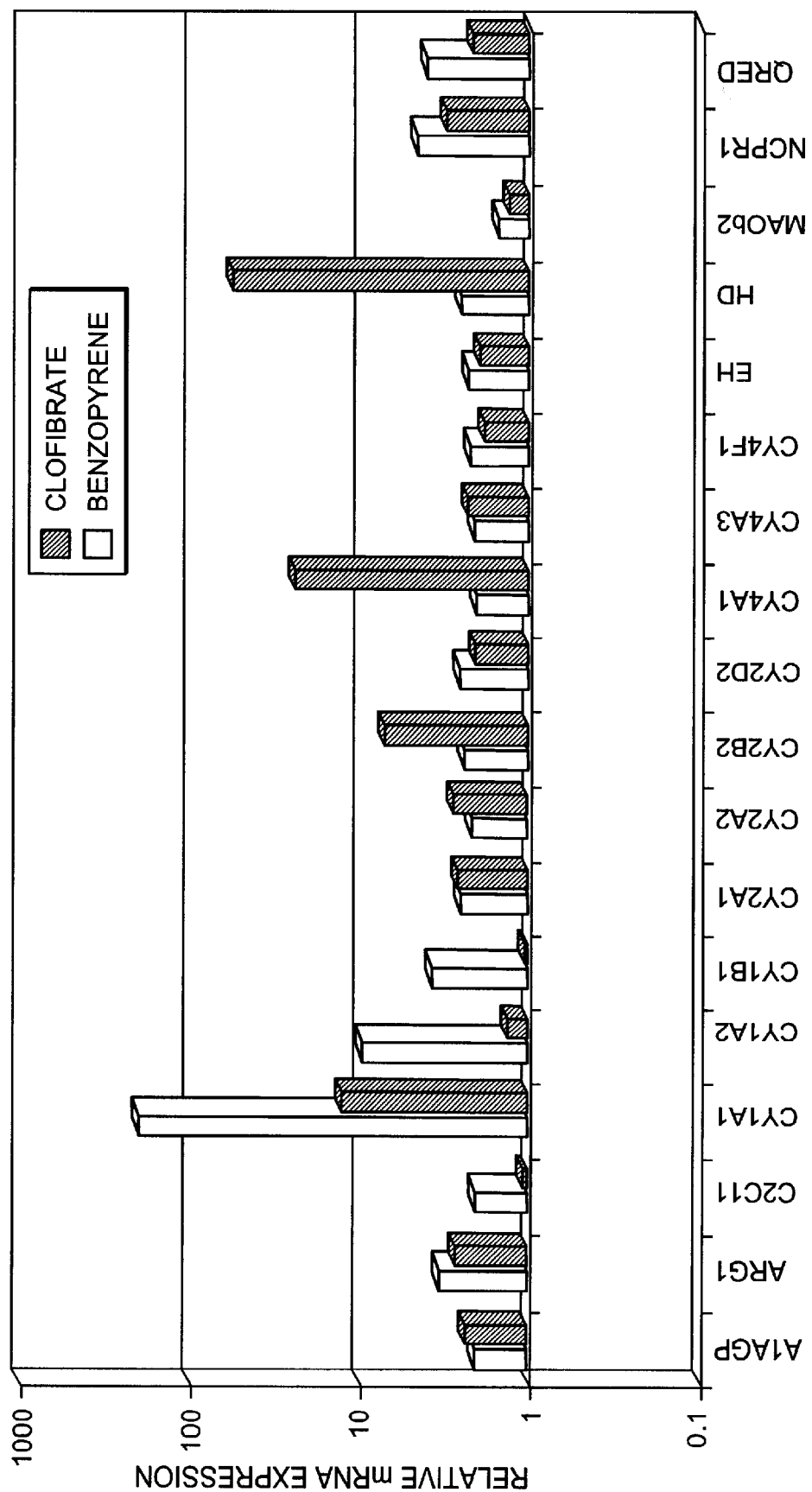
FIG. 32 illustrates the ability of the rat metabolism selected panel to differentiate drug responses (clofibrate versus benzo[a]pyrene) in Spraque-Dawley rats. Clofibrate (right hand bars) and Benzopyrene (left hand bars). The control (baseline) is a set of rats treated only with the carrier control.

The ability of the rat metabolism selected panel to differentiate drug responses Male rats were treated with 400 mg/kg/day of clofibrate or benzo[a]pyrene administered by mouth and the levels of gene expression were measured in liver tissue. The response to clofibrate and benzo[a]pyrene was determined in Sprague-Dawley rats using a rat metabolism panel. The results are shown in FIG. 32. Each drug gives a characteristic and distinct pattern of gene induction across the selected panel. As expected from the prior art, benzo[a] pyrene specifically induces gene expression at the loci for cyp 4A1 and HD. The control (baseline) is a set of rats treated only with the carrier control.

Example 19

The effect of administration of a stimulant is measured by a skin-epithelial/vascular/inflammation selected panel.

Figure 33:
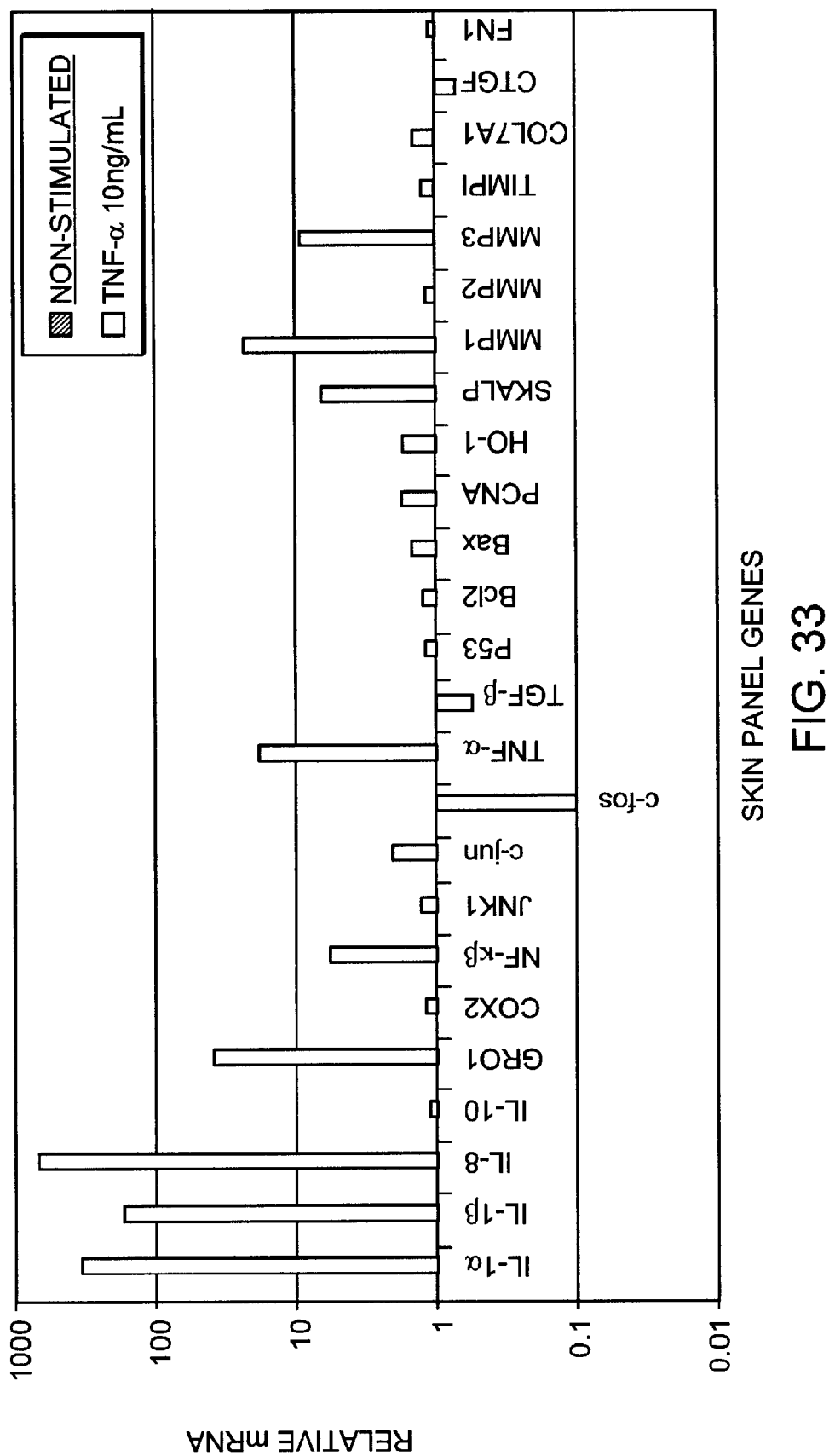
FIG. 33 illustrates the effect of administration of a stimulant (TNF-$\alpha$) as measured by a combination of constitutents selected from the inflammation, skin/epithelial, and vascular selected panels. The target is human keratinocytes in culture. The baseline is non stimulated cells. The baseline is a set of rats that were non-stimulated.

FIG. 33 illustrates the response of a subject to the administration of a stimulant (TNF-alpha, 10 ng/ml), as measured by a skin-epithelial, vascular/inflammation selected panel. In this example, the selected panel is created from constituents that are also found in other panels which have been here selected for purposes of best establishing an effect resulting from the stimulant.

Example 20

Use of a human liver selected panel for determining the metabolic properties of cryopreserved human hepatocytes .

Figure 34:
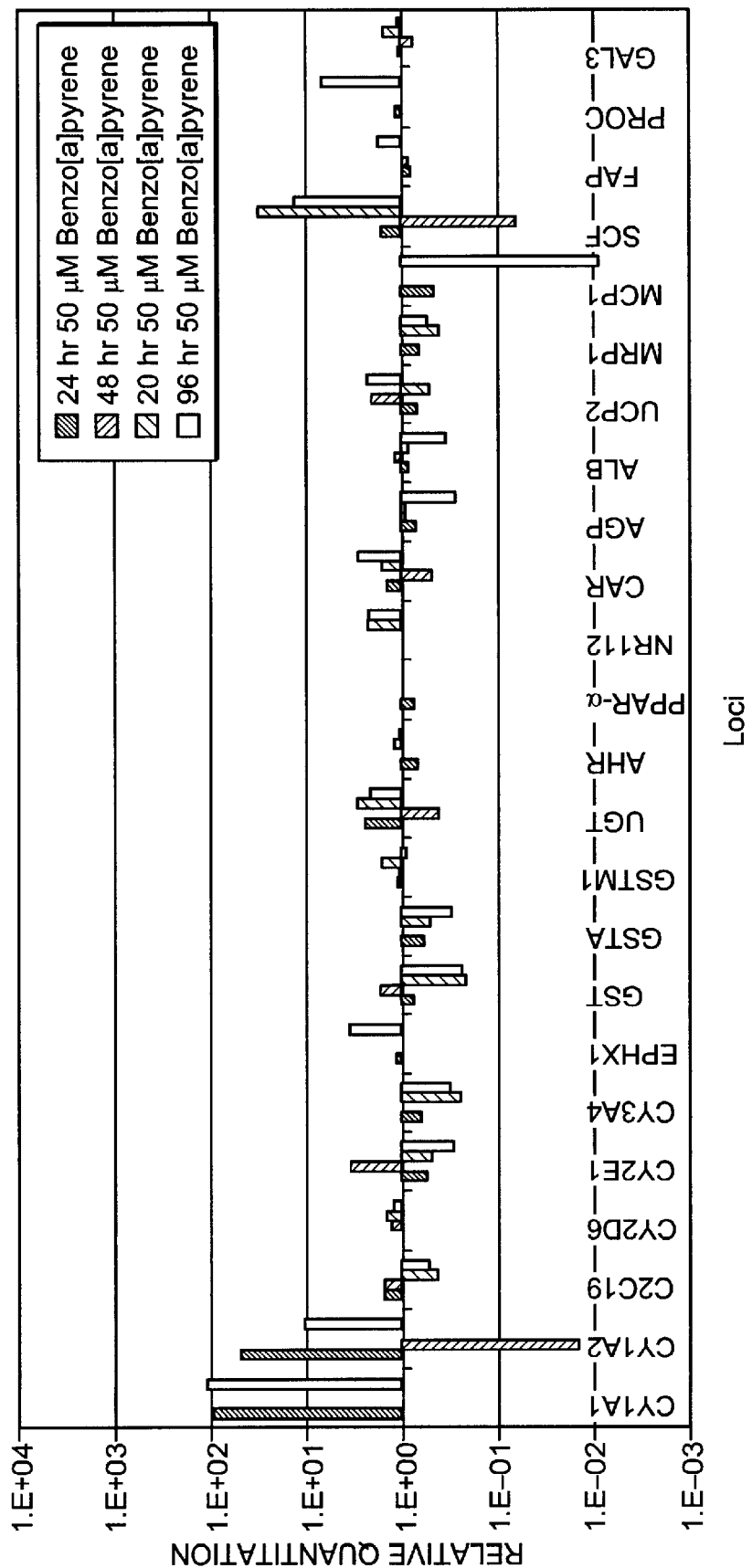
FIG. 34 illustrates the effect of administration of benzo[a]pyrene on cryo-preserved human hepatocytes over time as measured by the human liver selected panel. The control (baseline) are cells treated similarly but without the addition of benzo[a]pyrene.

Time/dose response experiments utilizing compounds with well-described toxicities and mechanisms of action are an early step in the biological validation of the selected panel. FIG. 34 shows the gene expression profile resulting from a timed study at constant dose of benzo(a)pyrene when administered to cryopreserved human hepatocytes.

Example 21

Response of human umbilical vein endothelial cells to TNF-α.

Figure 35:
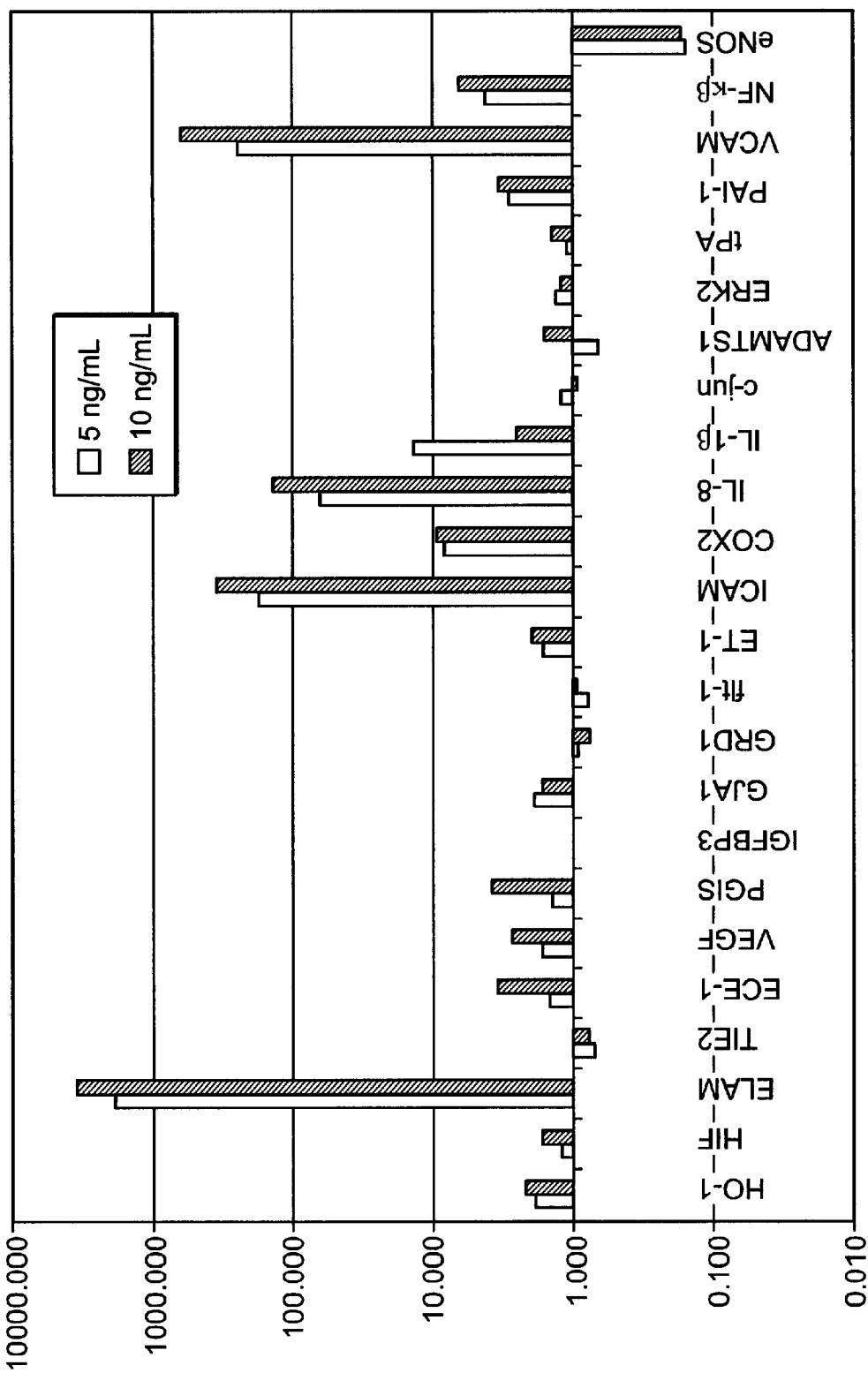
FIG. 35 demonstrates the effect of treating human umbilical vein endothelial cells in culture with TNF$\alpha$ for 24 hours. The control or baseline is established from cells handled similarly but without the addition of the stimulant.

FIG. 35 illustrates how endothelial cells respond to the inflammatory TNFα by the induction of expression of a number of gene loci, notably the adhesion molecules ELAM, ICAM, and VCAM. The cells were exposed for 24 hours. Both 5 ng/ml and 10 ng/ml are high doses of the immunostimulant TNFα and, as expected, no clear concentration response is observed at this dose level.

Example 22

This example is one illustration of the wide embodiments of the selected panels. In this example the effect of a compound in solution (NAC) is compared directly to the effect of an environmental stimulus (UVB) and the combined effect is read out as differential gene expression. FIG. 19 illustrates an similar effect of NAC only in blood obtained smokers and non-smokers. Dose and time experiments were conducted prior to this illustrated experiment.

Example 23

Gene expression profiles provide information on the effect of an environmental stimulus on cells.

This example is one illustration of the wide embodiments of the selected panels. In this example (see FIG. 36) the effect of a compound in solution (N-acetylcysteine) is compared directly to the effect of an environmental stimulus (UVB) and the combined effect is read out as differential gene expression. FIG. 19 illustrates an similar effect of NAC only in blood obtained smokers and non-smokers. Dose and time experiments were conducted prior to this illustrated experiment.

TABLE 1

Inflammation Selected Panel

| | |
|---|---|
| IL-1α | Interleukin-1 alpha |
| IL-1β | Interleukin-1 Beta |
| IL-2 | Interleukin-2 |
| IL-4 | Interleukin-4 |
| IL-6 | Interleukin-6 |
| IL-7 | Interleukin-7 |
| IL-8 | Interleukin-8 |
| IL-10 | Interleukin-10 |
| IL-12p40 | Interleukin-12p40 |
| IL-15 | Interleukin-15 |
| IL-18 | Interleukin-18 |
| GM-CSF | Granulocyte colony stimulating factor |
| IFNγ | Interferon gamma |
| TGFα | Tumor growth factor alpha |
| TNFα | Tumor necrosis factor alpha |
| TNFβ | Tumor necrosis factor beta |
| Cox 2 | Cyclooxygenase/prostaglandin-endoperoxide synthase 2 |
| ICE | Interleukin-1 converting enzyme |
| c-jun | MKK7, MAP2K7 |
| mmp9 | Matrix metalloproteinase |
| UPA | Urokinase plasminogen activator |
| HSP70 | Heat Shock Protein 70 kDa |
| CRE | cAMP Response Element |
| ICAM | Intercellular Adhesion Molecule |

TABLE 2

Cell Growth and Differentiation Selected Panel

| | |
|---|---|
| BIRC5 (Survivin) | Apoptosis inhibitor |
| NFKB1 | NF-kappaB |
| CDKN2A (P16) | Cell cycle inhibitor |
| TP53 (P53) | Tumor suppressor |
| TNFA | Tumor Necrosis Factor alpha |
| TERT | Telomerase Catalytic Subunit |
| BCL2 | Represses Apoptosis |
| BAX | Promotes Apoptosis |
| CASP1 (ICE) | Interleukin Converting Enzyme |
| GADD45A | Growth arrest protein |
| TNFRSF11A (RANK) | Receptor activator of NFkB |
| PDCD8 (AIF) | Apoptosis Inducing Factor |
| Apaf-1 | Apoptotic protease activating factor 1 |
| DFFB (DFF40) | Caspase activated DNAse |
| BAIAP3 (IAP1, BIRC3) | Inhibitor of apoptosis protein 1 (BAI-associated protein 3) |
| BIRC2 (IAP2) | Inhibitor of apoptosis protein 2 |
| Bik | BCL2 interacting killer |
| BCL2L1 (BCL-X) | BCL2-Like 1 |
| DAD1 | Defender against cell death 1 |
| MADD | MAP Kinase activating death domain |
| MAP3K14 | Mitogen-activated protein kinase kinase kinase 14 |
| PTEN | Protein tyrosine phosphatase |
| k-alpha-1 | Alpha tubulin (housekeeping, high abundance) |
| TOSO | Anti-fas induced apoptosis |
| cdk2 | Cyclin dependent kinase 2 |
| cdk4 | Cyclin dependent kinase 4 |
| CASP 3 | Apoptosis-related cysteine protease, 3 |
| CASP 9 | Apoptosis-related cysteine protease, 9 |
| RAD52 | DNA ds break repair |
| XRCC5 (Ku80) | X-ray repair complementing defective repair in Chinese hamster cells 5 |
| PNKP | Polynucleotide kinase 3' phosphatase |
| MRE11A | Meiotic recombination 11 homolog A |
| CCND1 (cyclin D1) | PRAD1: parathyroid adenomatosis 1 |
| CCND3 (cyclin D3) | Cyclin D3 |
| CCNE1 (cyclin E) | Cyclin E |
| CCNA2 (cyclin A) | Cyclin A |
| CCNB1 (cyclin B) | Cyclin B |
| CDKN2B (p15) | Cyclin-dependent kinase inhibitor 2B (p15, inhibits CDK4) |
| CDKN1A (p21) | Cyclin-dependent kinase inhibitor 1A (p21, Cip1) |
| RB1 | Retinoblastoma |
| BID | BH3 interacting domain death agonist |
| BAK1 | BCL2-antagonist/killer 1 |
| BAD | BCL2-antagonist of cell death |
| SMAC | Second mitochondria-derived activator of caspase |
| VDAC1 | Voltage-dependent anion channel 1 |
| CHEK1 | Checkpoint, S.pombe, homolog of, 1 |
| ABL1 | v-abl Abelson murine leukemia viral oncogene homolog 1 |
| TNFRSF12 | Tumor necrosis factor receptor superfamily, member 12 |
| TRADD | TNFRSF1A-associated via death domain |
| FADD | Fas (TNFRSF6)-associated via death domain |
| TRAF1 | TNFR associated factor 1 |
| TRAF2 | TNFR associated factor 2 |

TABLE 3

Human Liver Metabolism and Toxicity Selected Panel
(See FIG. 34)

| | |
|---|---|
| CYP1A2 | Polycyclic aromatic hydrocarbon (PAH) metabolism; induced by smoking Catalyzes formation of toxic APAP metabolite |
| CYP2A6 | Catalyzes oxidation in some pharmaceuticals, procarcinogens, and smoke constituents; upregulated in vitro after exposure to barbiturates or dex. |

TABLE 3-continued

Human Liver Metabolism and Toxicity Selected Panel
(See FIG. 34)

| | |
|---|---|
| CYP2E1 | Converts many small organic Compounds (i.e. EtOH, APAP, CC14) into reactive intermediatesInduced in alcoholics and in fatt phenotype. |
| CYP2D6 | Broad catalytic activities for over 30 therapeutic drugs. |
| CYP3A4 | Metabolism for a wide variety of drug types |
| UGT2B7 | UDP glycosyltransferase 2B7 |
| UGT2B15 | UDP glycosyltransferase 2B15 |
| EPHX1 | Microsomal epoxide hydrolase Multiple tissue-specific splicing variants |
| GSTA1 | Glutathione S-transferase alpha 1 |
| GSTA2 | Glutathione S-transferase alpha 2 |
| UCP-2 | Mitochondrial uncoupling protein 2 |
| TNF-α | Local inflammation Endothelial activation Released by PBMCs, Kupffer cells and activated tissue macrophages in the liver |
| TGF-β | Transforming growth factor beta 1 |
| iNOS | Inducible nitric oxide synthase; |
| SCF | Stem cell factor, released by activated hepatic stellate cells (HSC*); recruits mast cells (MC) to the liver |
| IFN-γ | Activation of macrophages |
| Galectin-3 | b-galactoside-binding lectin associated with cell growth, tumor transformation, and metastasis. |
| FAP | Fibroblast activation protein; membrane protease expressed at sites of tissue remodelling. |
| Procollagen C-proteinase (aka BMP1) | Extracellular matrix protein (bone morphogenetic protein 1) required for cartilage formation |
| Collagen I | Extracellular matrix (ECM) component |
| Collagen III | ECM component |
| Collagen IV | ECM component |
| Laminin | ECM component |
| Fibronectin | ECM component |

TABLE 4

Skin Response Selected Panel

| | |
|---|---|
| CRABP2 | Cellular retinoic acid-binding protein 2 |
| KRT14 | Keratin 14 |
| KRT5 | Keratin 5 |
| KRT16 | Keratin 16 |
| FGF7 | Fibroblast growth factor (KGF) Keratinocyte growth factor |
| FN1 | Fibronectin 1 |
| IVL | Involucrin |
| COL7A1 | Type VII collagen, alpha 1 |
| CTGF | Connective tissue growth factor |
| IL1α | Interleukin 1α |
| IL8 | Interleukin 8 |
| GRO1 | Melanoma growth stimulatory activity (MGSA) |
| PTGS2 | Prostaglandin-endoperoxide synthase 2 (COX2) Cyclooxygenase 2 |
| TNFα | Tumor necrosis factor alpha |
| TGFβ1 | Transforming growth factor beta 1 |
| PI3 | Proteinase inhibitor 3 (SKALP) Skin-derived antileukoproteinase |
| BSG | Basignin (EMMPRIN) Extracellular MMP inducer |
| MMP1 | Matrix metalloproteinase 1 (interstitial collagenase) |
| MMP2 | Matrix metalloproteinase 2 (72kD gelatinase) |
| MMP3 | Matrix Metalloproteinase 3 (Stromelysin 1) |
| TIMP1 | Tissue inhibitor of matrix metalloproteinase |
| HMOX1 | Heme oxygenase 1 |
| GADD45A | Growth arrest and DNA-damage-inducible alpha |
| PCNA | Proliferating cell nuclear antigen |
| DUSP1 | Dual specificity phosphatase (CL100) |

TABLE 4-continued

Skin Response Selected Panel

| | |
|---|---|
| MAPK8 | Mitogen activated protein kinase |
| TP53 | Tumor protein p53 (p53) |
| Bcl2 | B-cell CLL/lymphoma 2 |
| Bax | Bcl2-associated X protein |
| JUN | c-jun |
| FOS | c-fos |
| NR1I2 | Nuclear receptor subfamily 1, group I, member 2 (PAR2) Protease activated receptor 2 |
| S100A7 | S100 calcium-binding protein A7 (PSOR1) psoriasin 1 |
| TNSF6 | Tumor necrosis factor (ligand) superfamily, member 6 (FASL) Fas ligand |

TABLE 5

Prostate Selected Panel (See FIG. 30)

| | |
|---|---|
| PSA | Prostate Specific Antigen |
| DD3 | Prostate cancer antigen 3 |
| Survivin | Apoptosis Inhibitor 4 |
| PSMA | Prostate Specific Membrane Antigen Folate Hydrolase 1 |
| TERT | Telomerase Reverse Transcriptase Telomerase Catalytic Subunit |
| KLK2 | Human Kallikrein 2 |
| PDEF | Prostate-Derived Ets Factor |
| PSCA | Prostate Stem Cell Antigen |
| POV1 | Prostate Cancer Overexpressed Gene 1 |
| PART-1 | Prostate Androgen-Regulated Transcript 1 |
| MYC | c-myc |
| NRP1 | Neurophilin 1 |
| KAI1 | Human Metastasis Suppressor Gene |
| LGALS8 | Galectin 8 |
| p16 | Cyclin-Dependent Kinase 2A |
| GSTT1 | Glutathione-S-Transferase theta 1 |
| PAI1 | Plasminogen Activator Inhibitor 1 |
| bcl-2 | B-cell CLL/Lymphoma 2 |
| STAT3 | Transcriptional activator |
| IL-6 | Interleukin 6 |
| u-pa | Urokinase-Type Plasminogen Activator |
| KRT-5 | Keratin 5 |
| TGFβ | Transforming Growth Factor Beta |
| IL-8 | Interleukin 8 |
| VEGF | Vascular Endothelia Growth Factor |
| ACPP | Acid phosphatase, prostate |
| KRT-19 | Keratin 19 |
| CK-8 | Cytokeratin 8 |
| Maspin | Protease Inhibitor 5 |
| HMG-I/Y | Non-histone chromosomal protein |
| IGFR1 | Insulin Growth Factor Receptor 1 |
| HUPAP | Human Prostate-Associated Protease |
| P53 | Tumor suprressor |
| COX-2 | Cyclooxygenase 2 |
| E-CAD | e-cadherin |
| N-CAD | n-cadherin |
| CTNNA1 | α-1 catenin |
| PCANAP7 | Prostate cancer associated gene 7 |
| MRP1 | Multiple Drug Resistance Protein 1 |
| HSP-70 | Heat shock protein |
| TNF-A | Tumor Necrosis Factor |

TABLE 6

Vascular Selected Panel

| | |
|---|---|
| VEGF | Vascular Endothelial Growth Factor |
| NF kappa B | Nuclear Factor kappa B |
| TEK/TIE2 | Tyrosine kinase, endotheial |
| ERK2 | MAPK1: mitogen-activated protein kinase 1 |
| SELE | selectin E (endothelial adhesion molecule 1) |

TABLE 6-continued

Vascular Selected Panel

| | |
|---|---|
| Flt-1 | fms-related tyrosine kinase 1 (vascular endothelial growth factor/vascular perme-ability factor receptor) |
| PTX3 | pentaxin-related gene, rapidly induced by IL-1 beta |
| HMOX-1 | HMOX 1 = heme oxygenase (decycling) 1 |
| HIF-1 | Hypoxia-inducible factor 1, alpha subunit |
| GRD1 | Glutathione Reductase 1 |
| iNOS | Inducible nitric oxide synthase |
| ET-1 | Endothelin 1 |
| ECE-1 | endothelin converting enzyme 1 |
| PLAT | plasminogen activator, tissue |
| ADAMTS 1 | a disintegrin-like and metalloprotease (reprolysin type) with thrombospondin type 1 motif, 1 |
| PTGIS | prostaglandin I2 (prostacyclin) synthase |
| COX-2 | prostaglandin-endoperoxide synthase 2 (prostaglandin G/H synthase and cyclooxygenase) |
| VCAM | vascular cell adhesion molecule 1 |
| IL-8 | Interleukin 8 |
| Il-1 beta | Interleukin 1 beta |
| IGFBP3 | Insulin-like growth factor binding protein 3 |
| GJA1 | gap junction protein, alpha 1, 43kD |
| ICAM-1 | intercellular adhesion molecule 1 |

TABLE 7

Figure 31:
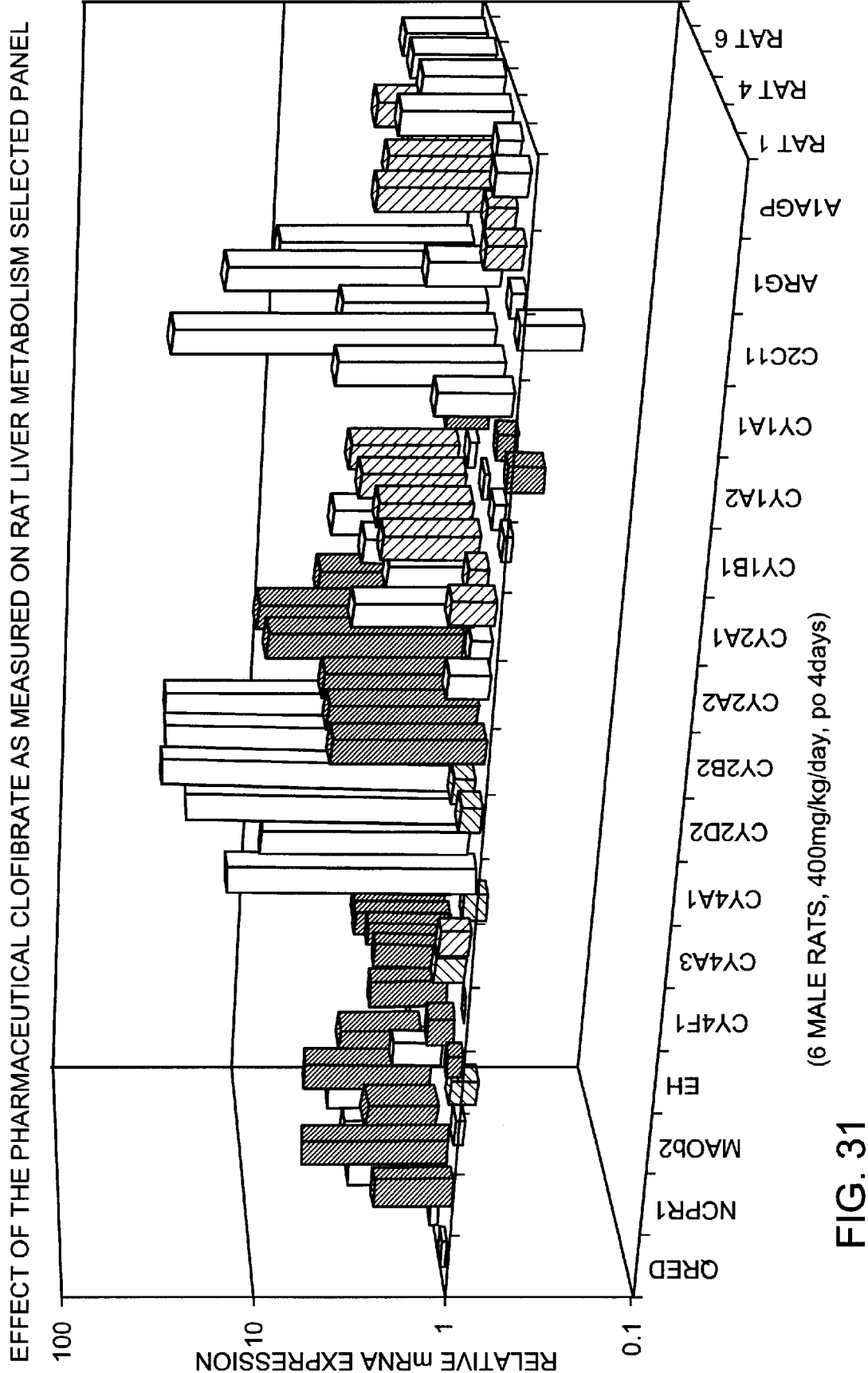
FIG. 31 illustrates the effect of the pharmaceutical agent, clofibrate, as measured on a rat liver metabolism selected panel. The profiles for six rats are provided as indicated on the z axis. The control (baseline) is a set of rats treated only with the carrier control.

Rat Liver Metabolism and Toxicity Panel
(See FIGS. 31 and 32)

| | |
|---|---|
| 1 | ALDH |
| 2 | aldose reductase |
| 3 | ARG |
| 4 | CYP1A1 |
| 5 | CYP1B1 |
| 6 | CYP2A2 |
| 7 | CYP2B2 |
| 8 | CYP2C11 |
| 9 | CYP2D2 |
| 10 | CYP2E1 |
| 11 | CYP2A1 |
| 12 | CYP3A1 |
| 13 | CYP1A2 |
| 14 | CYP4A1 |
| 15 | CYP4A3 |
| 16 | CYP4F1 |
| 17 | cytochrome P450 oxidoreductase |
| 18 | epoxide hydrolase |
| 19 | HD |
| 20 | MAO-B |
| 21 | quinone reductase |
| 22 | alpha-1-AGP |
| 23 | PPARalpha |
| 24 | GGT |

What is claimed is:

1. A method for determining a profile data set for a subject, based on a sample from the subject, the sample providing a source of RNAs, the method comprising:

using amplification for measuring the amount of RNA corresponding to at least four constituents from any one of Tables 1 through 7 and arriving at a measure of each constituent, where the profile data set comprises the measure of each constituent and wherein amplification is performed under measurement conditions (i) that are reproducible such that the coefficient of variation, on repeating the processes of using amplification and arriving at a measure, for the same sample and constituents, is less than approximately 3 percent and (ii) wherein efficiencies of amplification for all constituents differ by less than approximately ten percent.

2. A method according to claim 1, wherein efficiencies of amplification for all constituents differ by less than approximately 2 percent.

3. A method according to claim 1, wherein efficiencies of amplification for all constituents differ by less than approximately 1 percent.

4. A method according to according to any of claims 1–3, wherein the sample is of blood from the subject.

5. A method according to according to any of claims 1–3, wherein the sample is of a blood fraction from the subject.

6. A method according to according to any of claims 1–3, wherein the sample is of a body fluid from the subject.

7. A method according to according to any of claims 1–3, wherein the sample is a population of cells from the subject.

8. A method according to claim 7, wherein the population of cells is tissue.

9. A method according to claim 1, wherein the at least four constituents are selected from Table 1.

10. A method according to claim 1, wherein the at least four constituents are selected from Table 2.

11. A method according to claim 1, wherein the at least four constituents are selected from Table 3.

12. A method according to claim 1, wherein the at least four constituents are selected fiom Table 4.

13. A method according to claim 1, wherein the at least four constituents are selected from Table 5.

14. A method according to claim 1, wherein the at least four constituents are selected from Table 6.

15. A method according to claim 1, wherein the at least four constituents are selected from Table 7.

16. A method according to claim 1, further comprising:

storing the data set in a digital storage medium.

17. A method according to claim 16, wherein storing the data set includes storing it as a record in a database.

* * * * *

UNITED STATES PATENT AND TRADEMARK OFFICE
CERTIFICATE OF CORRECTION

PATENT NO.    : 6,692,916 B2
DATED         : February 17, 2004
INVENTOR(S)   : Michael P. Bevilacqua et al.

It is certified that error appears in the above-identified patent and that said Letters Patent is hereby corrected as shown below:

<u>Column 48,</u>
Lines 24, 26, 28 and 30 delete "according to" after "according to"

Signed and Sealed this

Twentieth Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,692,916 B2
DATED : February 17, 2004
INVENTOR(S) : Bevilacqua et al.

It is certified that error appears in the above-identified patent and that said Letters Patent is hereby corrected as shown below:

<u>Column 19,</u>
Lines 63-64, replace "(ii) The printer probe should amplify cDNA of less than 10 bases in length" with -- (ii) The printer probe should amplify cDNA of less than 110 bases in length --.

Signed and Sealed this

Twenty-seventh Day of December, 2005

JON W. DUDAS
*Director of the United States Patent and Trademark Office*